United States Patent [19]

Petersen

[11] Patent Number: 6,071,518
[45] Date of Patent: *Jun. 6, 2000

[54] GP900 GLYCOPROTEIN AND FRAGMENTS FOR TREATMENT AND DETECTION/DIAGNOSIS OF CRYPTOSPORIDIUM

[75] Inventor: Carolyn Petersen, Berkeley, Calif.

[73] Assignee: The Regents of The University of California, Oakland, Calif.

[*] Notice: This patent is subject to a terminal disclaimer.

[21] Appl. No.: 08/928,361

[22] Filed: Sep. 12, 1997

Related U.S. Application Data

[63] Continuation-in-part of application No. 08/700,651, Aug. 14, 1996, which is a continuation-in-part of application No. 08/415,751, Apr. 3, 1995, Pat. No. 5,643,772, which is a continuation of application No. 08/071,880, Jun. 1, 1993, abandoned, which is a continuation-in-part of application No. 07/891,301, May 29, 1992, abandoned.

[60] Provisional application No. 60/026,062, Sep. 13, 1996.

[51] Int. Cl.[7] .................... A61K 39/395; A61K 39/002; C12N 15/31; C07K 14/44

[52] U.S. Cl. .................. 424/139.1; 530/350; 536/23.4; 536/23.7; 424/191.1; 424/192.1; 424/269.1; 424/151.1; 424/172.1

[58] Field of Search ..................... 530/350, 822; 514/12; 424/269.1, 139.1, 151.1, 191.1, 191.2, 172.1; 536/23.7, 23.4

[56] References Cited

FOREIGN PATENT DOCUMENTS

93/24649  12/1993  WIPO ..................... C12Q 1/00

*Primary Examiner*—Mary E. Mosher
*Attorney, Agent, or Firm*—Hana Verny

[57] ABSTRACT

Peptides, polypeptides, glycoproteins, their functional mutants, variants, analogs, and fragments useful for treatment and detection/diagnosis of Cryptosporidium infections by competitive inhibition of the function of a Cryptosporidium protein/glycoprotein DNA and RNA encoding the Cryptosporidium protein/glycoprotein, mutants, variants and analogs and fragments thereof, and methods for production of recombinant or fusion proteins for use in treatment and detection/diagnosis.

22 Claims, 7 Drawing Sheets

6,071,518

GP900 GLYCOPROTEIN AND FRAGMENTS FOR TREATMENT AND DETECTION/DIAGNOSIS O a need to have available methods for reproducible expression of a recombinant, engineered or otherwise modified protein for competitive inhibition of infection. In addition there is a need to utilize synthetic molecules serving the same function as the protein competitive inhibitor. This approach requires that a specific Cryptosporidium protein/glycoprotein is cloned and identified as a potential candidate through its ability to competitively inhibit infection.

It is therefore a primary objective of this invention to provide a method for treatment of cryptosporidiosis involving recombinant, engineered or otherwise modified protein, or substitutes which have the same function as Cryptosporidium GP900 protein/glycoprotein in competitively inhibiting infection. Additionally such proteins or substitutes would be used for detection/diagnosis of cryptosporidiosis through competitive inhibition.

All patents, patent applications and publication cited herein are hereby incorporated by reference.

SUMMARY OF THE INVENTION

One aspect of the invention concerns a method for use of the GP900 molecule or a portion thereof, or its functional mutant, variant, analog or fragment as a competitive inhibitor of the function of the native glycoprotein GP900.

Another aspect of the invention is the use of protein/glycoprotein as a means to detect the presence of GP900 for diagnosis in a human or animal host or for detection of Cryptosporidium in the environment.

Still another aspect of this invention concerns a DNA and RNA encoding the Cryptosporidium protein/glycoprotein and fragments thereof for use in production of the protein/glycoprotein for development of agents used for treatment and diagnosis/detection.

Another aspect of this invention concerns an amino acid sequence of 1832 aa (SEQ ID NO: 5) of GP900, a >900 kD glycoprotein of sporozoites and merozoites, and its amino acid and size variants.

Another aspect of this invention concerns the DNA sequence of 5511 bp (SEQ ID NO: 2) nucleotides encoding GP900, and its nucleotide and size variants.

Another aspect is the DNA sequence of 7334 bp (SEQ ID NO: 1) nucleotides encoding the protein and its upstream (5') protein coding and regulatory elements and its 3' non-coding sequence.

Another aspect of this invention concerns the RNA sequence determined by the DNA sequence of GP900 and its nucleotide and size variants including the polyadenylation sequence.

Still yet another aspect of this invention concerns a group of GP900 recombinant or expressed proteins which are targets of polyclonal antibodies, which proteins inhibit Cryptosporidium infection, invasion, or adhesion.

Still another aspect of this invention concerns a method for treatment of $C.$ $parvum$ infection in a subject in need of such treatment, said method comprising administering to a subject infected with Cryptosporidium the peptide, polypeptide, glycoprotein, functional mutant, variant, analogue or fragment thereof formulated for delivery to the site of infection in amounts sufficient to competitively inhibit the Cryptosporidium at the site of infection.

Still yet another aspect of this invention is a method for treatment of Cryptosporidium infection comprising competitive inhibition of the function of GP900 resulting in the inhibition or prevention of infection of host cells by invasive forms of parasite.

Still yet another aspect of this invention is a method for prevention of Cryptosporidium infection of host cells resulting in cessation of the symptoms of infection, including but not limited to diarrhea.

Still yet another aspect of this invention concerns a method for diagnosing/detection of Cryptosporidium in a subject or in the environment by competitive inhibition, comprising steps:

(a) contacting a body specimen, fluid or tissue obtained from the subject or an environmental sample to be tested with the compounds of the invention; and (b) detecting the competitive inhibition of GP900 wherein the presence and the degree of receptor binding of GP900 of the invention indicates the presence of a Cryptosporidium organism in the subject or in the environment.

Still yet another aspect of this invention concerns a method for detecting anti-Cryptosporidium antibody in a subject, said method comprising steps:

(a) contacting a body specimen, fluid or tissue obtained from the subject with the compounds of the invention; and (b) detecting a formation of antibody-antigen complex, wherein the presence of the complex inhibits GP900-receptor binding and thereby indicates the presence of a Cryptosporidium antibody in the subject.

Still another aspect of this invention is a Cryptosporidium diagnostic or detection kit comprising protein or glycoprotein according to the invention and a means for detection of native GP900 protein or glycoprotein or an antibody-GP900 antigen complex utilizing the principle of competitive inhibition of the function of GP900.

DEFINITIONS

Figure 1:
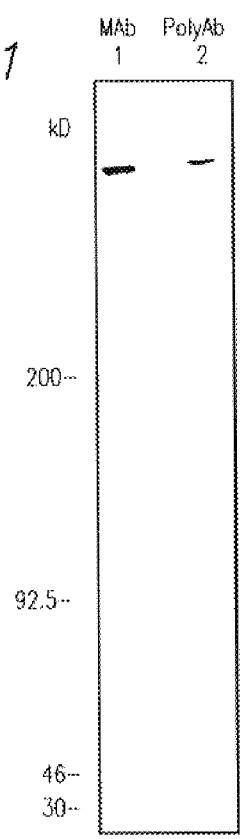
FIG. 1 is an immunoblot of *Cryptosporidium parvum* oocyst/sporozoite proteins showing detection of the >900 sporozoite protein with monoclonal and polyclonal antibodies to GP900.

As used herein:

"Treatment" means therapeutic use of any protein, peptide or glycoprotein to inhibit existing infection in a host.

"Detection" means establishing or providing evidence for the presence or prior presence of living or dead Cryptosporidium by detecting protein or glycoprotein function or competition of function in the host, in a host tissue specimens, or in environmental samples including water, soil, food, etc.

"Diagnosis" means establishment of the presence or prior presence of Cryptosporidium infection or disease by detecting protein or glycoprotein, protein or glycoprotein function or competition of function as a component of a diagnostic assay according to the invention. Diagnosis includes establishment of the presence of antibody by the same method.

"GP900" means a high molecular weight protein represented by 1832 amino acids and identified as SEQ ID NO: 5 of Mr greater than 900 kilodaltons (kD) which may have attached glycoprotein, said GP900 detected at the surface of sporozoites or merozoites. GP900 is the target of antibodies which inhibit infection, invasion or adhesion of Cryptosporidium. GP900 includes protein and carbohydrate moieties attached to protein including variants defined by differential glycolysation and conformational changes.

"Differential glycosylation" means glycoproteins which vary in the carbohydrate moieties attached to the protein backbone as a function of factors other than the sequence of the protein backbone.

"Conformational change" means change in the shape of the protein or the glycoprotein as a result of changes in the carbohydrate moieties bound to it and/or changes in the protein sequence.

The "structure" or "structural characteristics" of GP900 defines a protein, glycoprotein, DNA and RNA encoding the GP900 protein and includes all structural variations, mutations and fragments exhibiting the same function.

The "functionality" "functionally active", "functional" or "functional characteristics" of GP900 means and is defined by the interaction of antibodies to GP900 and to its described structural variants, such that the antibody inhibits infection, invasion or adhesion of Cryptosporidium through such interaction. These terms also mean the interaction of GP900 with host cells or receptors present on host cells such that GP900 prevents infection, invasion or adhesion of Cryptosporidium to the host cells.

"The gene" or "genes encoding GP900" means DNA encoding a portion or all of the GP900 protein and flanking regions.

"Sporozoites or merozoites" means any life stage which may invade host cells and any variant or mutant of said sporozoites or merozoites.

"Antibodies" means proteins which structurally interact with the target antigen and are produced when the antigen is introduced into an animal, such that they stimulate the immune system. The term also includes antibodies produced in vitro, such as antibodies produced by hybridoma cell cultures and chimeric proteins, as well as hybridoma cells and chimeric constructs introduced into the host to provide an in vivo antibody.

"Antibodies to GP900" means proteins which structurally interact with the target antigen GP900 and inhibit infection, invasion or adhesion of the sporozoites or merozoites to the host cell.

"Carbohydrate" or "carbohydrate moiety" means any N- or O-linked carbohydrate or portion thereof, which is covalently linked to the protein of GP900.

"Target of competitive inhibition" means a protein GP900 or carbohydrate moiety attached to protein or lipid moiety on the host cell (the receptor) which interacts with GP900 during invasion of the host cell by C. parvum. Target inhibition also means the interaction of GP900 and the receptor.

"GP900 antigen" means a protein with or without a carbohydrate attached thereto which defines the capacity of Cryptosporidium sporozoites and merozoites to infect host cells.

"GP900 DNA" means the sequences identified as SEQ ID NOs.: 1–4, which encode a portion or all of the GP900 protein (SEQ ID NOs. 5, 6, and 12–20) and any variant, 5' extension, mutation and fragment thereof, which corresponds to genes encoding the antigen. Variants include but are not limited to the partial sequence of GP900-NINC isolates, the full sequence of GP900 Iowa isolates and all the variants.

"GP900 RNA" means the RNA sequence corresponding to DNA sequences (SEQ ID NOs. 1–4) which encode the protein sequences of GP900 protein identified specifically as SEQ ID NOs: 5, 6 and 12–20) and any 5' extension, variant, mutation and fragment thereof.

"Prevention or prophylaxis" means treatment.

"Host" or "subject" means a human or animal host, including birds and cattle.

"Regulatory elements" means nucleotide sequences which control the expression of genes they regulate, typically by interaction with other macromolecular species such as proteins.

"Cryptosporidium species" or Cryptosporidium" means any organism belonging to the genus Cryptosporidium, such as, for example, *Cryptosporidium parvum* or *Cryptosporidium muris*, but also includes currently less well characterized other organisms such as, for example, Cyclospora and it is also meant to include apicomplexan parasites which invade the gastrointestinal tract, such as Eimeria. Cryptosporidium species comprise Apicomlexan parasites which primarily invade cells of the gastrointestinal tract and cause disease in a susceptible host.

"Competitive inhibition" means the capacity of a substance acting as a competitive inhibitor to mimic the activity or replace a native substance such that it can block or reverse the events initiated by the native substance.

"Analog" or "analogue" means a compound that resembles another in structure and/or in function.

DETAILED DESCRIPTION OF THE INVENTION

This invention is based on finding that certain peptides, polypeptides, glycoproteins, and their functional mutants, variants, analogs, and fragments are suitable for treatment and detection/diagnosis of C. parvum infection by competitive inhibition. The method for treatment according to the invention utilizes competitive inhibition of the function of a Cryptosporidium molecule comprised of a protein with or without carbohydrates attached thereto.

This invention also provides DNA and RNA encoding the Cryptosporidium GP900 molecule, mutants, variants and analogs and fragments thereof, and methods for production of recombinant or fusion proteins for use in treatment and detection/diagnosis using competitive inhibition.

The invention, therefore, primarily relates to methods for treatment, detection and diagnosis of cryptosporidiosis in human and animal subjects by way of providing therapeutic compounds which competitively inhibit the Cryptosporidium or compounds which detect its existence using a principle of competitive inhibition. Recombinantly produced GP900, peptides, polypeptides, glycoproteins, and their functional mutants, variants, analogs, and fragments are produced for treatment, diagnosis and detection of infections caused by any Cryptosporidium organisms or any organism belonging to Cryptosporidium species.

More specifically, the invention concerns identification of a Cryptosporidium protein/glycoprotein, comprised of a protein or polypeptide with or without a carbohydrate attached thereto, identification of DNA of the Cryptosporidium protein/glycoprotein gene, sequencing DNA encoding the molecule, and expressing portions of the locus encoding the Cryptosporidium protein/glycoprotein or their engineered analogues to prepare competitive inhibitor molecules for treatment/prophylaxis/detection/diagnosis of infection in humans and animals.

I. Cryptosporidium Protein/glycoprotein Antigens

Cryptosporidium organisms and particularly *Cryptosporidium parvum* are coccidian parasites of the gastrointestinal tract that cause a clinical syndrome of diarrhea for which there is currently no effective treatment. Infectivity of Cryptosporidium is mediated by a protein or polypeptide molecules of sporozoites or merozoites, the infective forms of Cryptosporidium.

During the development of this invention, it has been shown that a *Cryptosporidium parvum* expression library clone S34 encoded a portion of a protein larger than 900 kD, recognized by hyperimmune bovine colostrum (HBC), which has been designated GP900. (*Infect. Immun.*, 60:2343 (1992), 60:5132 (1992), and 61:4079 (1993)).

The GP900 protein was found to be highly abundant and easily visualized by Coomassie blue staining of proteins on SDS-polyacrylamide gels (SDS-PAGE) and is Triton X-100 soluble and N-glycosylated. The protein has been detected in micronemes of the invasive stages of Cryptosporidium by immunoelectronmicroscopy and has been shown to be accessible to surface radioiodination with $^{125}$I.

Monoclonal antibodies, which are specific for GP900, have been made according to Example 2. Three of six antibodies, namely 10C6, 7B3, and E6, made from a single fusion event in which the immunogen was an oocyst containing sporozoites, were specific to GP900, suggesting that GP900 is a highly immunogenic molecule of sporozoites. Three of eight antibodies, namely M2, M15 and M24 made from a second fusion event, in which the immunogen consisted of meronts, were also specific to GP900, suggesting that GP900 is a highly immunogenic molecule of merozoites.

Antibodies, for the purposes of this invention, are not used as therapeutic agents but only as a tool for identification of GP900 or other proteins, peptides, polypeptides or glycoproteins of interest and as a control component of a kit.

For the method for treatment of cryptosporidiosis by competitive inhibition, an antigen protein/glycoprotein, designated GP900 was identified and sequenced at the DNA level. Four GP900 DNA sequences were established. SEQ ID NO: 1 comprising 7334 bp is the sequenced GP900-Iowa gene locus comprised of open reading frame (ORF) and 3' and 5' flanking regions. SEQ ID NO: 2 comprising 5511 bp encodes the open reading frame of GP900 of the Iowa isolate. SEQ ID NO: 3 comprising 5318 bp is the sequenced GP900 NINC gene locus comprised of 3' flanking region. SEQ ID NO: 4 comprising 5163 bp encodes the available open reading frame of GP900 of the NINC isolate which is missing the 5' flanking region. The deduced protein sequences of encoded protein GP900-Iowa consisting of 1832 aa (SEQ ID NO: 5) and partial protein GP900-NINC consisting of 1721 aa (SEQ ID NO: 6) were established.

The DNA encoding Cryptosporidium antigen can be coupled to Cryptosporidium DNA encoding regulatory elements located downstream or upstream or on another chromosome in the Cryptosporidium genome. These operably coupled DNA segments are able to bind selectively and specifically to Cryptosporidium molecules, such as proteins.

Expressed portions of the GP900 loci are targets of polyclonal and monoclonal antibodies able to inhibit invasion/intracellular development in vitro and in vivo. In addition, expressed portions are able to directly inhibit invasion/intracellular development in vitro and in vivo. The expression, identification and isolation of these recombinant proteins allows production of recombinant proteins or analogs for a treatment modality based on inhibition of infection of the host with cryptosporidiosis and for a diagnosis/detection modality based on replacement of GP900 by competitive binding.

1. GP900 Protein, Glycoprotein, Recombinant Protein and DNA/RNA

A. Identification of Protein GP900 as Cryptosporidium Antigen

Cryptosporidium antigen identified as GP900 protein is a high molecular weight glycoprotein of a Mr greater than 900 kilodaltons (kD). The GP900 protein was detected in micronemes of developing merozoites and sporozoites. It is present on the surface of the sporozoites and is shed from the sporozoite surface in vivo in host cells. When deglycosylated, the GP900 core protein has a variable molecular weight of approximately 150–250 kD. The GP900 protein has been identified as a target of anti-GP900 antibodies which inhibit Cryptosporidium infection, invasion or adhesion.

GP900 proteins were identified and isolated from oocysts of the Iowa, AUCP-1 NINC isolates of *Cryptosporidium parvum*, as described in Example 1 and tested for their interaction with specific anti-GP900 antibodies. Proteins which were shown to be targets of GP900 antibodies were prepared according to Example 2, and visualized by enzyme-linked immunosorbent assay (ELISA), chemiluminimscense or with $^{125}$I labeled Protein A followed by autoradiography as described in Example 7.

Polyclonal antibodies against SDS solubilized GP900 and MAb 10C6, prepared according to Example 4, which were previously shown to detect GP900, were used for detection of molecular species which are immunoprecipitable with both mono and polyclonal antibodies. A Western blot probe of oocyst/sporozoite proteins is seen in FIG. 1. Immunoprecipitation of sporozoite surface labeled proteins with mono and polyclonal antibodies as seen in FIG. 2.

Figure 7:
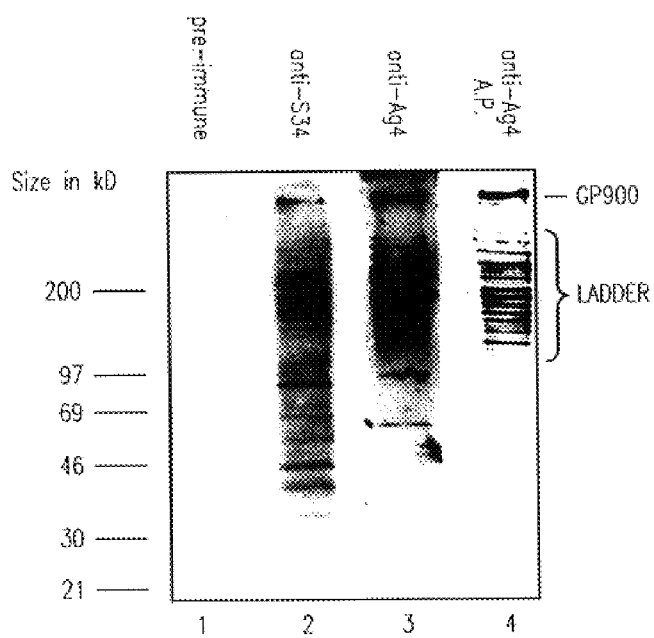
FIG. 7 shows an immunoblot using antibodies to recombinant GP900 proteins.

FIG. 1 shows an immunoblot of *Cryptosporidium parvum* oocyst/sporozoite proteins of the AUCP-1 isolate separated by SDS-PAGE. FIG. 7, Lane 1 shows the MAb 10C6 culture supernatant, Lane 2 shows the polyclonal anti-GP900 in 1:5000 dilution.

As seen in FIG. 1, a single molecular species, namely protein GP900, was identified at ~900 kD by both monoclonal and polyclonal antibodies. Cross-immunoprecipitation studies confirmed that the same protein of approximately 900 kD size, was seen by both antibodies. At prolonged periods of detection, a less prominent ladder of bands between the 200 and 92 kD markers was observed.

Figure 2:
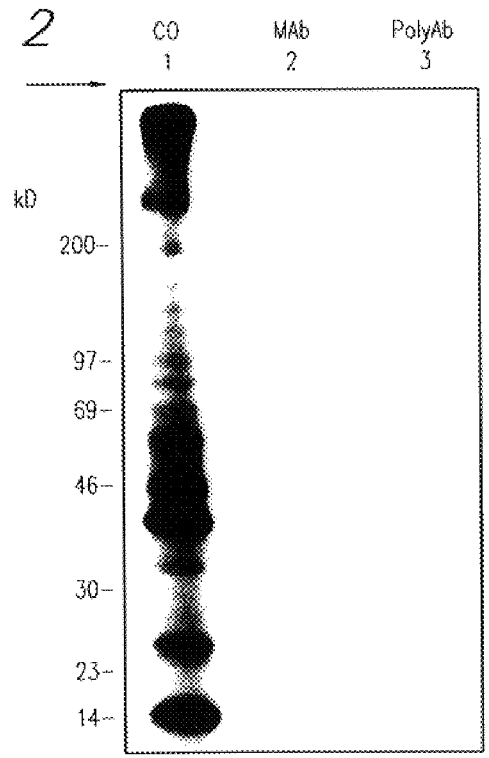
FIG. 2 shows the immunoprecipitation of $^{125}I$ surface label *Cryptosporidium parvum* sporozoite proteins using monoclonal and polyclonal antibodies to GP900.

FIG. 2 shows immunoprecipitation of $^{125}$I radiolabelled *Cryptosporidium parvum* sporozoite surface proteins of the AUCP-1 isolate separated by 5–15% SDS-PAGE. FIG. 2, lane 1 shows radiolabeled *Cryptosporidium parvum* sporozoite surface protein control ($10^7$ sporozoites/lane). Lane 2 shows radiolabeled *Cryptosporidium parvum* sporozoite surface proteins immunoprecipitated with polyclonal anti-GP900.

As seen in FIG. 2, lane 2, Immunoprecipitation of $^{125}$I labeled sporozoites with polyclonal anti-GP900 revealed that polyclonal anti-GP900 only detects one protein, GP900, at the surface of sporozoites. Polyclonal anti-GP900 antibody is thus an appropriate antibody for GP900 localization experiments and for detection of clones in a Cryptosporidium expression library.

Prominent sporozoite surface proteins of other Apicomplexan parasites, for example, the circumsporozoite protein of the Plasmodium species, which contains the binding ligand for adhesion of the malaria sporozoite to its host cell, the hepatocyte, are known to be shed from the surface of sporozoites in vivo.

In order to determine whether GP900 similarly was shed from the surface of Cryptosporidium sporozoites, living sporozoites were allowed to glide on poly-L-lysine coated slides as described in Example 3. Results are shown in FIG. 3.

FIG. 3 shows the indirect immunofluorescence detection of GP900 with MAb 7B3 after fixation of the sporozoites with formaldehyde. MAb 7B3 was used because it was previously shown to detect only GP900 on immunoblots of Cryptosporidium sporozoite proteins. FIG. 3 shows that GP900 is present around the living sporozoite and is shed from the posterior aspect of living sporozoites as the sporozoite locomotes.

In order to determine the subcellular localization of GP900, anti-GP900 mouse ascites were assayed on LR White embedded electronmicrographic sections of ileum from experimentally infected rats that contained all developmental stages of the parasite as described in Example 10. Results are seen in FIG. 4.

In FIG. 4, the micronemes of merozoites observed within a developing schizont appear as stacked plate-like radiolucent structures in which the gold particles of the second antibody, used to localize GP900 polyclonal antibodies, are concentrated. GP900 was also seen in sporozoites within oocysts (data not shown). The rhoptries and dense granules were not labeled. No surface labeling of sporozoites and merozoites was observed. No gold particles were detected in the parasitophorous vacuole or over the vacuolar wall. No antigen could be detected in host-cell cytoplasm.

In order to show that GP900 is a glycoprotein, N-linked carbohydrate was enzymatically removed from *Cryptosporidium parvum* oocyst/sporozoite proteins and the remaining protein was separated by SDS-PAGE and detected with MAb 10C6 on an immunoblot by the techniques described in *Infect. Immun.,* 60:5132 (1992) and in Example 7. Results are seen in FIG. 5.

FIG. 5 indicates that deglycosylation removes reactivity with MAb 10C6 (lane 1), a GP900 reactive MAb, and generates new reactivities (lane 2) which exhibit a ladder-like pattern between markers having apparent molecular weight 97 and 200. The estimated Mr of those molecular species in this figure are 150,000–180,000. This data is consistent with the removal of N-linked carbohydrate moieties from the GP900 protein backbone and with the appearance of the protein backbone alone or with incomplete removal of all N-linked carbohydrates or O-linked sugars. It is also consistent with potential size polymorphism in the GP900 core protein or combination of these events.

An anti-GP900 polyclonal antibody, affinity purified from oocyst/sporozoite antibodies on the protein expressed by a gt11 clone S34 using S34 recombinant eluted antibody (S34 REA), also detected a Mr greater than 900,000 protein in intact sporozoites and a ladder of proteins with the smallest at about Mr 150,000 after N-deglycosylation. Cross immunoprecipitation experiments showed that these three reagents, S34 REA, and anti-GP900 polyclonal and monoclonal MAb 10C6 antibodies, detected the Mr >900,000 protein indicating that the S34 clone encodes a portion of the core protein which when glycosylated corresponds to the GP900 protein (*Infect. Immun.,* 60:5132 (1992)).

B. GP900 Gene Cloning/Sequencing and Genomic Southern Analysis

The GP900 gene of *Cryptosporidium parvum* was isolated from a naturally infected neonatal calf (NINC) isolate. DNA from the calf isolate was used to prepare a gtll expression library containing overlapping clones which described a partial open reading frame for GP900 which is 5163 bp. The sequence of this open reading frame was determined in the following way.

Clone S34 was previously determined to encode a portion of a much larger protein, GP900, using S34 REA. A second GP900 clone, designated Ag4, reacted with polyclonal anti-GP900 and a MAb to GP900 but the Ag4 and S34 insert DNAs did not cross-hybridize with one another. Upon sequencing, the clones were found to contain distinctly different sequences with no overlap. The DNA inserts were used to double screen the genomic library to determine if a clone encoding both could be identified indicating that Ag4 and S34 were colinear portions of the same gene. Clone DB8, which hybridized to both S34 and Ag4, contained a single open reading frame containing both the S34 and the Ag4 sequences. PCR amplification products generated from the 5' and 3' terminal sequences of DB8 were used to identify additional clones at the 5' and 3' ends of the locus. When added to the DB8 sequence, the sequence generated from these clones comprised the open reading frame which is still open at the 5' end and a 3' flanking noncoding region.

The complete coding sequence of the Iowa isolate GP900 gene, which shows high homology to the NINC gene, was also cloned and sequenced. The sequence was established by PCR using sequencing primers from the NINC sequence and template DNA of the Iowa isolate with subsequent cloning of overlapping sequences in pFusTrx or Bluescript for sequencing. At least two independent clones were sequenced in both directions to identify and correct PCR errors. The 5' region was sequenced from a 2.2 kb BamH1 fragment cloned into Bluescript.

The GP900 reading frame was verified by the in-frame expression of S34 and Ag 4 as β-galactosidase fusion proteins and domains 1- and 3 as thioredoxin fusion proteins. All four fusion proteins elicited antibodies to GP900 when used to immunize animals (data not shown). The FastA and blastp programs of GenBank were used to perform homology searches of the Swiss Protein database and showed homology of GP900 to mucin-like proteins.

Genomic Southern analysis (FIG. 6), as described in Example 8, was undertaken to determine if GP900 was encoded by a single gene and if so whether this gene was polymorphic in the isolates for which DNA was available, namely the Iowa and AUCP-1 isolates. DB8 DNA from NINC isolate was used as a probe. The sequence of DB8 contains no EcoRI (lane 1), Bgl II (lane 2) or Hinf III (lane 3) sites but contains many (10) Hinf I sites. Lane 4 shows Iowa isolate, lane 5 shows AUCP-1. Results are seen in FIG. 6.

Figure 6:
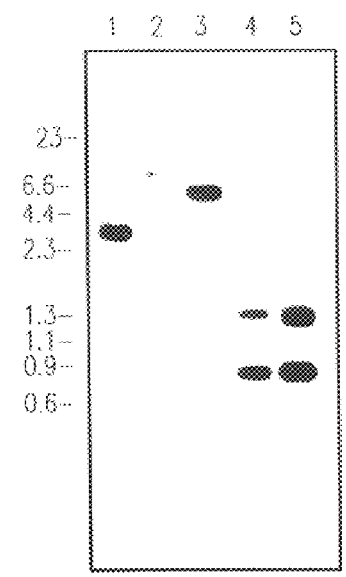
FIG. 6 is the genomic Southern analysis of the GP900 gene fragment.

FIG. 6 shows that the DB8 probe of the NINC Cryptosporidium isolate hybridizes to a single DNA fragment in EcoRI, Bgl II and Hind III digests of the Iowa strand, indicating that GP900 is encoded by a single prominent gene. The larger restriction fragment of lanes 4 and 5 are approximately 1150 bp and include parts of domains 1 and 2. The smaller fragment contains 2 comigrating fragments of approximately 740 and 800 bp. These fragments encompass the two polythreonine regions of the DBA probe. No difference pattern was seen in between the Iowa and DBA isolates. These data indicate that gross GP900 gene rearrangements have not occurred in the three different isolates studied. This observation is further confirmed by the fact that both the Iowa and AUCP isolates produce a large 900 kD protein which reacts with the polyclonal antibodies to GP900 initially prepared against the AUCP-1 isolate.

C. Structure of the GP900 Gene and its Encoded Protein

Sequences identified as SEQ ID NOs: 1–4 are nucleotide sequences of the GP900 gene or gene fragment of Iowa or NINC isolates. The sequence identified as SEQ ID NOs: 5 and 6 are the corresponding proteins.

Figure 12:
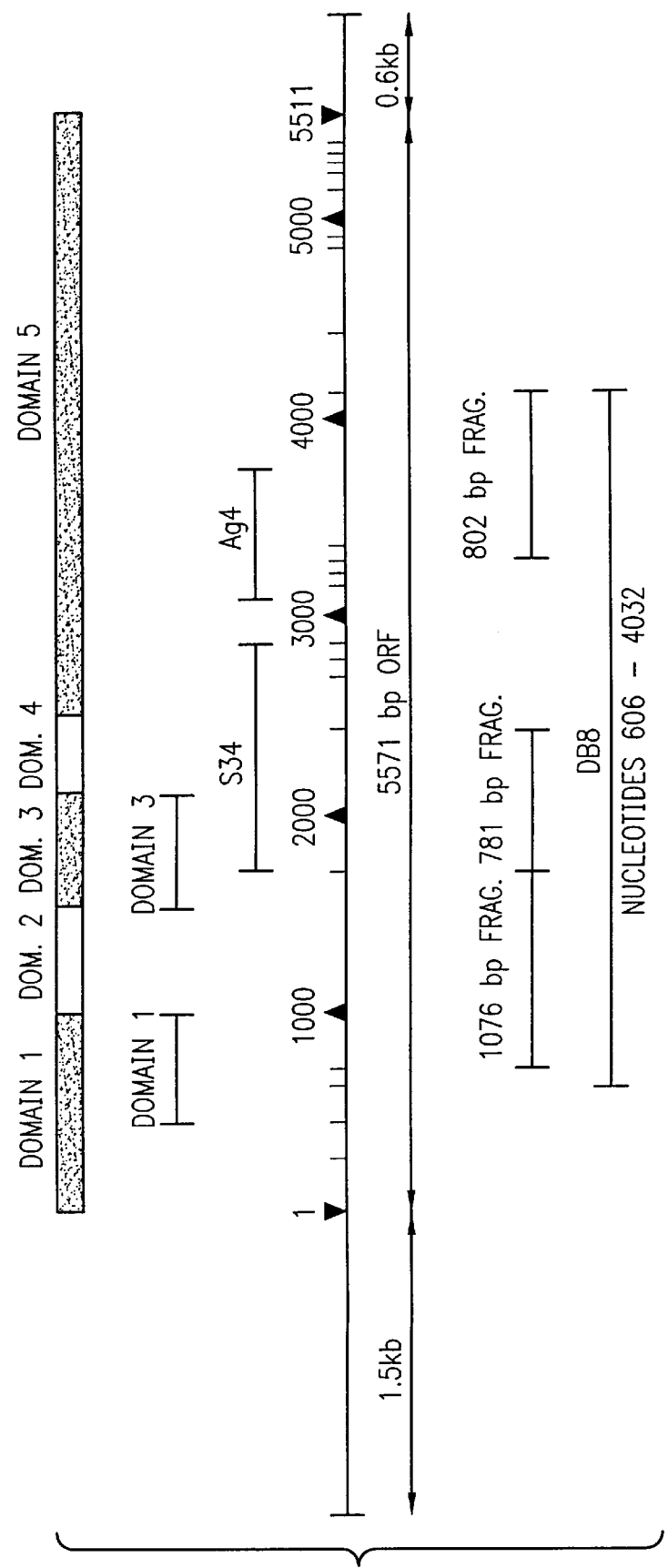
FIG. 12 is the domain structure of GP900 indicating domains 1–5.

GP900 ORF encodes a multidomain protein based on predicted structural differences as seen in FIG. 12.

The predicted sequence GP900 open reading frame of Iowa isolate contains 5 structurally distinct domains two of which are polythreonines NINC isolate also containing 5 domains (SEQ ID Nos: 26–30)(SEQ ID NOs: 7–11 and FIG. 12).

Domains 1 (SEQ ID NO: 7) and 3 (SEQ ID NO: 9) of the protein SEQ ID NO: 5 are cysteine rich domains, where domains 2 (SEQ ID NO: 8) and 4 (SEQ ID NO: 10) are mucin-like domains containing large numbers of threonines.

Domain 1 (SEQ ID NO: 7) contains 5 cysteine residues in the Iowa isolate. Domain 3 has 7 cysteines in the Iowa isolate (SEQ ID NO: 9) but only 6 cysteines in the NINC isolate (SEQ ID NO: 6). Neither domain 1 or domain 3 is highly homologous to any known sequence in GenBank or Swiss Protein Bank.

Domain 2 (SEQ ID NO: 8) and domain 4 (SEQ ID NO: 10) are composed largely of threonine residues. Both domains also contain repeats of the sequence lysine-lysine-proline or lysine-proline. Variants of domain 2 (SEQ ID NOs: 6 and 12–20) consisting of two NINC isolates variants and eight Iowa isolates variants indicate that size and sequence variants are frequent in this domain. When the deduced protein sequence was analyzed by searches of the GenBank and Swiss Protein Bank, the greatest similarities were found between the threonine-rich regions of GP900 and other glycoproteins with either proven or putative O-linked glycosylation including a variety of gastrointestinal mucins.

Domain 5 (SEQ ID NO: 11) is composed of a degenerate 8-mer repeat and contains a putative membrane spanning region and a cytoplasmic domain.

Five domains of the NINC protein (SEQ ID NO: 6) have sequences identified as SEQ ID NO: 26–30. Domain 1 (SEQ ID NO: 26) contains the first 191 amino acids of the N-terminal, Domain 2 (SEQ ID NO: 27) contains 216 amino acids. Domain 3 (SEQ ID NO: 28) contains 159 amino acids. Domain 4 (SEQ ID NO: 29) contains 112 amino acids. Domain 5 (SEQ ID NO: 30) contains 1043 amino acids of the 3' end.

Figure 5:
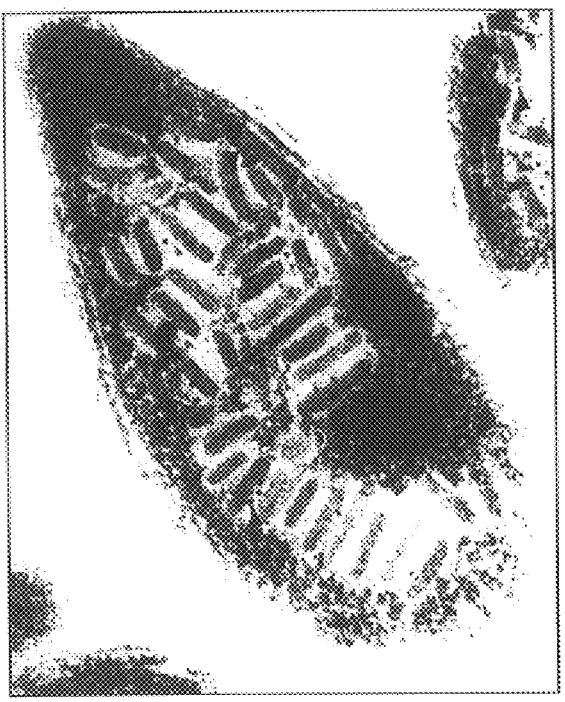
FIG. 5 is the immunoblot of *Cryptosporidium parvum* N-deglycosylated sporozoite/oocyst proteins using monoclonal antibodies to GP900.

GP900 is both N- and O-glycosylated. GP900 has been shown to be susceptible to treatment with N-glycosidase F (N-glycanase) which cleaves high mannose and complex structures as seen in FIG. 5.

The presence of abundant cysteines on a surface protein of Cryptosporidium which is functionally homologous to the circumsporozoite protein of malaria strongly suggests that these cysteines participate in binding phenomena and may comprise new binding motifs. Numerous apicomplexan parasite proteins, such as Plasmodium, CSP, Duffy binding protein, EBA and PFEMPI have binding domains which contain cysteine rich regions. N- or O-linked carbohydrate moieties may also participate in binding to adjacent cells.

D. Expression of GP900 Recombinant Proteins

Recombinant GP900 protein useful in the method of treatment by competitive inhibition was expressed using methods described in Example 16.

Briefly, the S34 insert was subcloned into the glutathione-S transferase vector, expressed as a soluble protein and purified according to supplier's instructions.

Domain 3 (amino acids 520–678) and domain 1 (amino acids 164–303) corresponding to the terminal 139 amino acids of domain 1 which appeared to be a DNA duplication of domain 3 were expressed as thioredoxin fusion proteins in the vector pTrusFux according to supplier's protocols (Invitrogen). Sense and anti-sense PCR amplification oligonucleotides, which allowed the amplification from Iowa genomic Cryptosporidium DNA of domain 1 or domain 3 with Kpn 1 and Xba I sequences at the 5' and 3' ends respectively, were synthesized. The sense oligonucleotides were:
5'-CAGGTACCCATGAATTGGCCGGTAAGTATC-3' (SEQ ID NO: 21) for domain 1 and 5'-CAGGTACCCTCTGAAACTGAGAGTGTAATT-3' for domain 3 (SEQ ID NO: 22). The antisense oligonucleotides were: 5'-CCTCAGATTAGTGTTTCACTCCAACACA-3' for domain 1 (SEQ ID NO: 23) and 5'-CCTCTAGATTATACGAAATCAGCTGAAGT-3' for domain 3 (SEQ ID NO: 24). Amplified fragments were digested with Kpn I and Xba I, purified and introduced in a directional manner into the polylinker region of pTrxFus. Ligation products were transformed into G1724 E. coli and ampicillin resistant colonies were screened by hybridization of colony replicas with $^{32}$P-labeled domain 1 and domain 3. Purified colonies were grown in 1 ml aliquots for analysis. The identity of foreign DNA was verified by sequence analysis. Growth conditions were varied with respect to time and the bacteria lysed for evaluation of soluble and insoluble proteins. Domain 1 and domain 3 were wholly soluble. Yields were maximal at 3 hours of bacterial growth. Domains 1 and 3 were purified by heat treatment and their purity and concentration determined on Coomassie stained gels. Concentration was also determined using the Bradford reagent and UV detection at 595 nm.

E. Production and Assay of GP900 Antibodies

In order to prepare reagents for specific portions of GP900 to assay their effects on sporozoite adhesion, invasion and intracellular development in vitro and infection in vivo, polyclonal antibodies were made to purified wild type β-galactosidase, and thioredoxin; Ag4-β-galactosidase and S34-β-galactosidase fusion proteins; and domain 1 thioredoxin, and domain 3 thioredoxin fusion proteins according to Examples 5 and 6.

In order to further define the antigen and S34 antibodies by removing the reactivity to β-galactosidase, affinity purified antibodies to the Ag4 and S34 portions of their fusion proteins were prepared according to Example 5. These various antibody preparations were used to probe an immunoblot of proteins from *Cryptosporidium parvum* oocysts/sporozoites as described in Example 7. Results are shown in FIG. 7.

FIG. 7 is an immunoblot of proteins obtained from *Cryptosporidium parvum* oocysts or sporozoites. Marker size in kD is indicated. Lane 1 contains oocyst/sporozoite proteins probed with pre-immune rabbit serum. Lanes 2–4 are probed with the serum of rabbit immunized with recombinant S34 and Ag4 antigen. Lane 2 is probed with anti-S34 antibody. Lane 3 is probed with the anti-Ag4 antibody. Lane 4 is probed with the anti-Ag4 affinity purified (A.P.) antibody.

FIG. 7, lane 1, shows that the pre-immune serum from the rabbit which received the S34 antigen is mildly reactive to two proteins of *Cryptosporidium parvum*. After immunization with the S34 antigen (lanes 2–4), the antisera react with a whole variety of proteins including GP900, a ladder of proteins ranging in size from 100 to 250 kD, and several different proteins of lower molecular weight. Since the S34 sequence carries the poly-threonine repeats, it would seem that the antibody which recognizes these repeats will also recognize other proteins with this repeated motif and that the multiple bands represent such cross reactions. However, the results point toward another interpretation. The polyclonal antibody directed against Ag4, which does not carry poly-threonine repeats, and the affinity purified Ag4 antibody, recognize GP900 as well as the ladder of proteins between 150–250 kD, suggesting that the ladder of proteins represents the core proteins of GP900, not cross-reacting proteins. The multiple bands appear to reflect glycolysation and/or protein variants of GP900.

Figure 8:
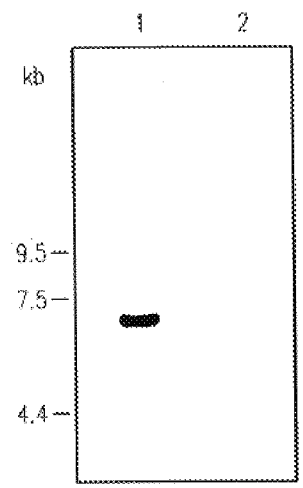
FIG. 8 is a northern blot of GP900.

Northern blot analysis of GP900 from in vitro culture of isolate organisms using $^{32}$P-labeled domain 3 as a hybridization probe revealed a message of 6.8 kb as shown in FIG. 8 and described in Example 8.B.

E. In vitro and In Vivo Assessment of Activity of Anti-GP900 and Anti-Recombinant GP900 Antibodies Since some antigens localized in the apical complex and extruded from it have been found to be adhesion molecules and the targets of inhibitory antibodies for other Apicomplexan parasites and to be suitable vaccine targets (*Cell*, 70:1021 (1992); *J. Immunol.*, 149:548 (1992)), antibodies to fusion proteins of four expression clones were prepared from the GP900 locus, domain 1-(amino acids 164–303), domain 3 (amino acids 520–678), S34 (amino acids 598–964) and Ag4 (amino acids 1030–1226) incorporated within SEQ ID NO: 5.

Immunoglobulin from unimmunized rabbits and rabbits immunized with domain 1 thioredoxin and domain 3 thioredoxin was affinity purified on protein A. Antibodies to S34 were more highly purified on a recombinant S34 affinity column and only antibodies to S34 were present in the final preparation.

Figure 9:
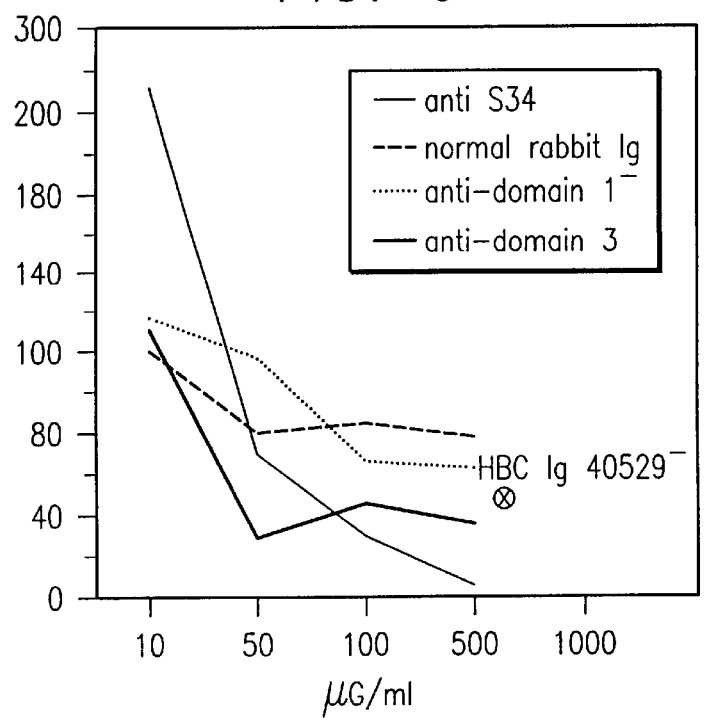
FIG. 9 is a graphical illustration of the dose-dependent inhibition of sporozoite invasion/intracellular development in MDCK cells in vitro by affinity purified anti-S34 antibody, normal anti-rabbit Ig and anti-domain 1 and anti-domain 3 antibodies.

FIG. 9 graphically summarizes the effects of affinity purified antibodies assayed for inhibition of Iowa isolate *C. parvm* in the MDCK cell invasion and assay (Infect. Immuopment assay (*Infect. Immunol.*, 61:4079 (1993)). The values were normalized to 10 µg/ml of unimmunized rabbit antibody. Antibody preparation is described in Examples 2, 5 and 6 and the adhesion inhibition assay is described in Example 14. The positive control of inhibition was HBC Ig 40529 at a 1:40 dilution (800 µg/ml Ig). This antibody was previously shown to confer protection against parasite invasion in vitro and in whole animal infection models (*Infect. Immun.*, 61:4079 (1993)). Results were graphed as a function of % invasion normalized to 10 µg/ml normal rabbit antibodies.

Affinity purified anti-S34 inhibited invasion in a dose dependent manner over the concentration range tested (10 to 500 µg/ml) with an $IC_{50}$ of about 75 µg/ml. Invasion was inhibited by 93% relative to control. Relative to the unimmunized rabbit antibody, anti-S34 enhanced invasion at low concentrations. However, MAbs to different epitopes within the cysteine-rich domain of the gal/galNAc lectin of *Entamoeba histolytica* inhibit or enhance adhesion of *Entamoeba histolytica* (*Infect. Immunol.*, 61:1772 (1993)). S34 may contain epitopes which elicit both enhancing and inhibiting antibodies and the sum effect may be different at different concentrations of antibody.

At the highest concentration of antibody, 500 µg/ml, unimmunized rabbit control antibody inhibited invasion by 20% compared to the 10 µg/ml immunized rabbit control antibody control. Antibody against domain 1 inhibited invasion by 30%.

Taken together, the observations that antibody to determinants in the S34 and domain 3 recombinant proteins significantly inhibited invasion suggested that these parts of overlapping fragments of the protein might contain functionally important portions of GP900 involved in invasion.

In order to determine whether the native or recombinant antibodies raised against Cryptosporidium antigen GP900 or a fraction thereof are able to inhibit Cryptosporidium infection in vivo, the anti-S34-β-galactosidase antibodies were tested in a neonatal mice model as described in Example 16. Results are seen in FIG. 10.

Figure 10:
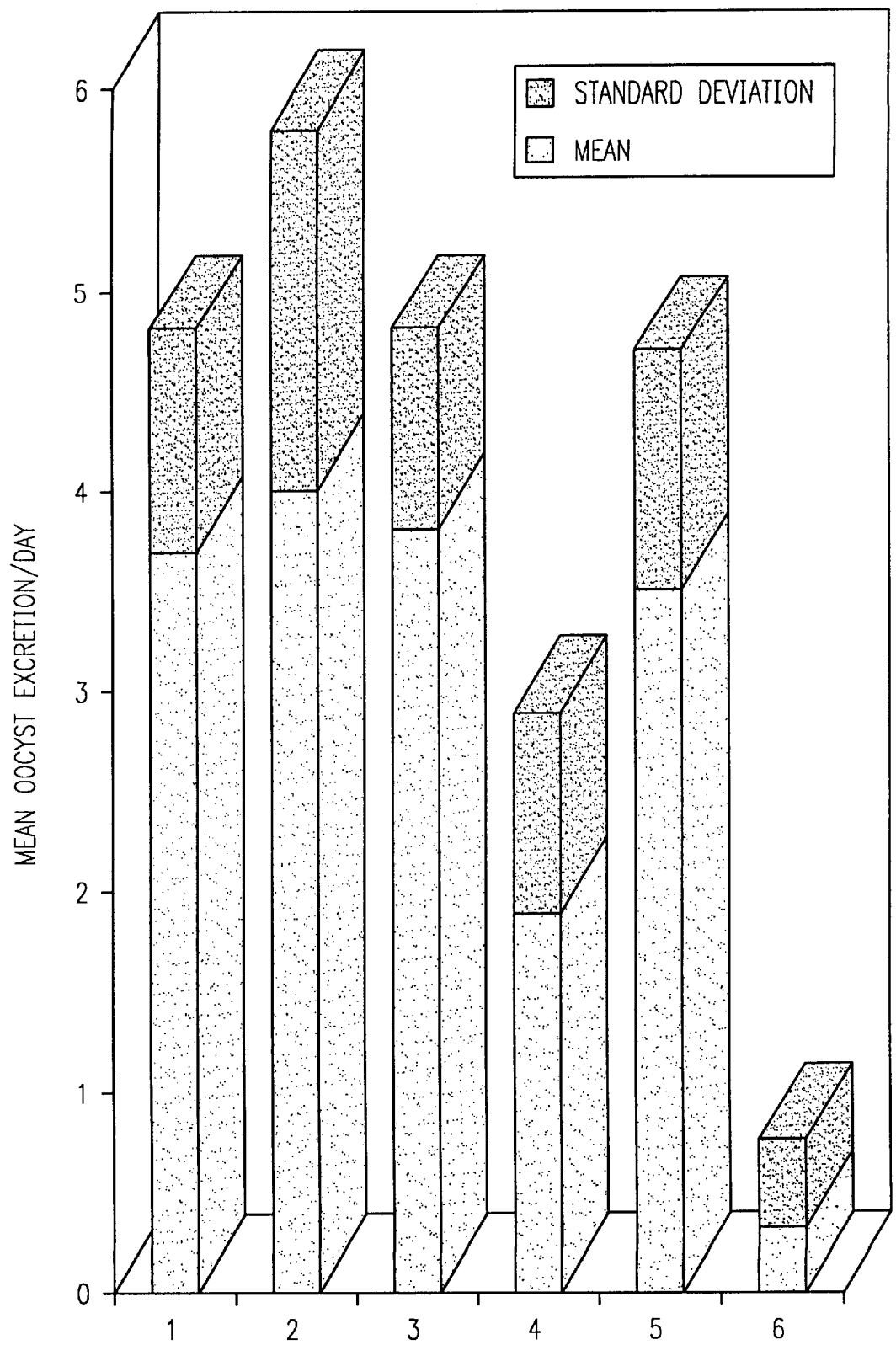
FIG. 10 is a graphical illustration of the inhibition of parasite burden in vivo in neonatal mice challenged with Cryptosporidium and treated with oral anti-recombinant GP900 antibodies.

FIG. 10 is a graph representing the amount of excretion of Cryptosporidium oocysts per day in mice treated with phosphate buffered saline (bar 1); anti-β-galactosidase (bar 2); anti-Ag4β-galactosidase (bar 3); anti-S34-β-galactosidase (bar 4); 1:5 HBC Ig 40529 (bar 5); and paromomycin (bar 6).

As seen in FIG. 10, anti-S34 (bar 4) reduced the oocysts shed by about 50% relative to control PBS (bar 1) and anti-β-galactosidase antibody (bar 2). Although crude antisera was used, antibody to S34-β-galactosidase inhibited shedding by about 50% relative to the control(s) (bar 1 and bar 2) treated with PBS and anti-β-galactosidase antibody. The inhibition was superior to the inhibition conferred by a 1:5 dilution of HBC Ig 40529 (bar 5), the positive control antibody which had previously been shown to prevent cryptosporidial disease in calves challenged with Cryptosporidium (*Infect. Immun.*, 61:4079–4084 (1993)).

From the results obtained in these experiments, it is clear that clone S34 encodes a Cryptosporidium antigen and that the antibodies specifically raised against this antigen are able to inhibit Cryptosporidium infection in vivo.

In order to determine whether GP900, like the circumsporozoite protein of malaria, is an adhesion glycoprotein mediating the attachment of the sporozoite to a cell of gastrointestinal origin, a paraformaldehyde fixed Caco-2 cell adhesion assay was used to assess antibodies to β-galactosidase, Ag4-β-galactosidase and S34-β-galactosidase, as described in Example 14. In this assay, the same magnitude of inhibition of adhesion of Cryptosporidium sporozoites to Caco-2 cells (mean O.D. 50% of control in ELISA) with a 1:50 dilution of anti S34-β-galactosidase was conferred as was observed in the in vitro invasion and intracellular development assay in living MDCK cells by a 1:40 dilution of the same antibody.

In addition, these results were comparable to those seen when a 1:100 dilution of anti-Cryptosporidium murine ascites (48% inhibition) a polyclonal rabbit anti-Cryptosporidium antiserum (inhibition 51%) were previously assayed in this system (data not shown). Similarly to the in vivo model, in this in vitro model, the anti-Ag4-β-galactosidase also did not inhibit invasion and intracellular development. However, anti-S34 inhibited invasion/intracellular development in living MDCK cells in vitro, adhesion in killed Caco-2 cells in vitro and infection in vivo in mice. These results show that a biological function is inhibited by anti-S34 antibodies in the in vitro and in vivo systems and that that function is adhesion. Additionally, these results show that antibodies to recombinant GP900 correlate significantly with the inhibitory activity of HBC Ig 40529 and anti-Cryptosporidium antibodies from mouse and rabbit sources.

Thus antibodies against the recombinant S34 protein are able to significantly inhibit Cryptosporidium infection in vitro and in vivo indicating the usefulness of the anti-S34 antibody for both anti-Cryptosporidium prophylaxis and therapy of a human or animal host.

F. Purification of GP900

GP900 proteins were purified as described in Example 17.

G. Inhibition of Invasion In Vitro by GP900 Proteins

Sporozoite invasion is competitively inhibited by native GP900 and recombinant domain 3.

Purified native GP900 of Cryptosporidium has recently been found to bind to Caco-2A cells in a saturable, dose dependent manner in an assay designed to assess attachment of sporozoites to host cells (Abstracts, *Natural Cooperative Drug Discovery Groups for the Treatment of Opportunistic Infections Meetings*, 1996 and 1997, Bethesda, Md.).

Purified native GP900, recombinant proteins (domains 1- and 3, S34) and a domain 2 synthetic peptide were assayed to determine if inhibition by antibodies to S34 and domain 3 reflected inhibition of a ligand which was involved in sporozoite attachment/invasion. Domains 1- and 3 were expressed in soluble form as thioredoxin fusion proteins in pTruxFus (Invitrogen), a prokaryotic expression vector chosen for its capacity to allow expression of biologically active receptors/ligands due to correct folding of cysteine rich proteins (*Endocrinology*, 138:588 (1997)). Native GP900 and recombinant domains 1 and 3 were purified and assayed for their capacity to inhibit invasion/intracellular development in vitro as a percentage of the invasion control, RPMI. Results are seen in FIG. 11.

Figure 11:
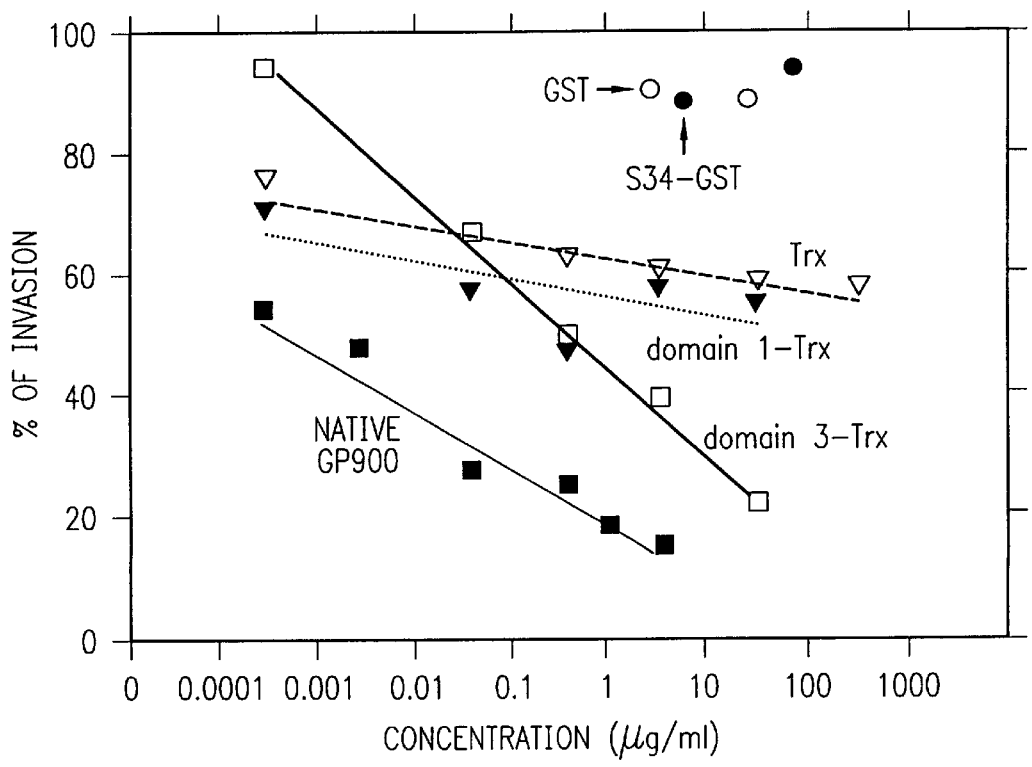
FIG. 11 is the graphical illustration of the inhibition of sporozoite invasion/intracellular development in vitro by native GP900 and recombinant proteins representing portions of GP900.

FIG. 11 shows that affinity purified native GP900 very significantly inhibits invasion/intracellular development with an $IC_{50}$ of approximately 2.5 ng/ml. The $IC_{50}$ of domain 3 thioredoxin is 330 ng/ml. Thioredoxin alone and domain 1 thioredoxin had nearly equivalent inhibitory activity and did not reach an $IC_{50}$ level at the highest concentrations assayed (33 and 330 μg/ml, respectively). Purified S34-GST and GST have no effect on invasion (FIG. 11), even though S34-GST at concentrations of 100 nM and 1 μM completely blocked the inhibitory activity of anti-S34 antibody. These studies suggest that the S34GST fusion protein although binding S34 antibodies which inhibit invasion is either not expressed in correct form for inhibitory activity itself or does not contain determinants which are critical for inhibition. The domain 2 repeat peptide TTTTTTTKKPTTTTT (SEQ ID:NO 25)(Table 1) did not block invasion/intracellular development in vitro. Taken together, these data indicate that the inhibitory activity of GP900 is partially expressed by the domain 3 fusion protein. The fusion protein inhibits invasion at a nanomolar level which is 3 logs higher than the inhibitory concentration of the native protein (picomolar), but is still low by pharmacologic standards.

G. GP900 Proteins, Variants and Oligonucleotide Sequences

Twenty-four sequences identified as SEQ ID NO: 1–24 are disclosed in this invention. These sequences were prepared according to methods described in Examples 11 and 16.

SEQ ID NO: 1 is the 7334 bp DNA sequence of the Iowa isolate comprised of the open reading frame and 3' and 5' flanking regions.

SEQ ID NO: 2 is the 5511 bp DNA sequence of the GP900 NINC Iowa isolate and is comprised of the ORF.

SEQ ID NO: 3 is the 5318 bp partial DNA sequence GP900 NINC isolate comprised of the partial ORF and 3' flanking region.

SEQ ID NO: 4 is a 5163 bp DNA sequence of GP900 NINC isolate and is comprised of the partial ORF.

SEQ ID NO: 5 is the deduced 1832 aa sequence of GP900 of the Iowa isolate.

SEQ ID NO:6 is the deduced 1721 partial amino acid sequence GP900 of the NINC isolate.

SEQ ID NO:7 is an amino acid sequence of domain 1 of GP900 of the Iowa isolate consisting of 303 amino acids.

SEQ ID NO: 8 is an amino acid sequence of domain 2 of GP900 of the Iowa isolate consisting of 216 amino acids.

SEQ ID NO: 9 is an amino acid sequence of domain 3 of GP900 of the Iowa isolate consisting of 159 amino acids.

SEQ ID NO: 10 is an amino acid sequence of domain 4 of GP900 of the Iowa isolate consisting of 112 amino acids.

SEQ ID NO: 11 is an amino acid sequence of domain 5 of GP 900 of the IOWA isolate consisting of 1042 amino acids.

Sequences 12–19 are size and sequence variants comprising domain 2 of Iowa isolate.

SEQ ID NO: 12 is an Iowa isolate variant sequence comprising domain 2 (95 aa domain 2 and conserved flanking amino acids), consisting of 128 amino acids.

SEQ ID NO: 13 is an Iowa isolate variant sequence comprising domain 2 (97 aa domain 2 and conserved flanking amino acids), consisting of 130 amino acids.

SEQ ID NO: 14 is an Iowa isolate variant sequence comprising domain 2 (97 aa domain 2 and conserved flanking amino acids), consisting of 130 amino acids.

SEQ ID NO: 15 is an Iowa isolate variant sequence comprising domain 2 (105 aa domain 2 and conserved flanking amino acids), consisting of 138 amino acids.

SEQ ID NO: 16 is an Iowa isolate variant sequence comprising domain 2 (91 aa domain 2 and conserved flanking amino acids), consisting of 124 amino acids.

SEQ ID NO: 17 is an Iowa isolate variant sequence comprising domain 2 (142 aa domain 2 and conserved flanking amino acids), consisting of 175 amino acids.

SEQ ID NO: 18 is an Iowa isolate variant sequence comprising domain 2 (117 aa domain 2 and conserved flanking amino acids), consisting of 150 amino acids.

SEQ ID NO: 19 is an Iowa isolate variant sequence comprising domain 2 (58 aa domain 2 and conserved flanking amino acids), consisting of 91 amino acids.

SEQ ID NO: 20 is a NINC isolate variant sequence comprising domain 2, consisting of 249 amino acids.

SEQ ID NO: 21 is a sense oligo for domain 1 (216 aa domain 3 and conserved flanking amino acids), consisting of 30 bp.

SEQ ID NO: 22 is a sense oligo for domain 3 consisting of 30 bp.

SEQ ID NO: 23 is an antisense for domain 1, consisting of 28 bp.

SEQ ID NO: 24 is an antisense oligo for domain 3 consisting of 29 bp.

SEQ ID NO: 25 is the domain 2 repeat peptide shown in Table 1.

SEQ ID NO: 26 is an amino acid sequence of domain 1 of GP900 NINC isolate consisting of 191 amino acids.

SEQ ID NO: 27 is amino acid sequence of domain 2 of GP900 NINC isolate consisting of 216 amino acids.

SEQ ID NO: 28 is an amino acid sequence of domain 3 of GP900 NINC isolate consisting of 159 amino acids.

SEQ ID NO: 29 is an amino acid sequence of domain 4 of GP900 NINC isolate consisting of 112 amino acids.

SEQ ID NO: 30 is an amino acid sequence of domain 5 of GP900 NINC isolate consisting of 1043 acids.

H. Other Variants and Mutants

Table 1 comprises an alignment of domain 2 protein variants. These consist of 8 variants (SEQ ID NOs: 12–19) of the Iowa sequence (SEQ ID NO: 5) and 1 variant (SEQ ID NO: 10) of the NINC sequence.

As seen in Table 1, domain 2 polymorphins of the GP900 contains variable numbers of threonine lysine and proline amino acids. Those are encoded by extensive trinucleotide repeats of the DNA end Sequence (SEQ ID NO: 6). Similar trinucleotide repeat regions occur and have been characterized in the genes responsible for a number of inheritable genetic diseases of man including fragile X syndrome. Insertions and deletions in these trinucleotide repeat regions are reflected in the translated protein which is functionally different. In addition, decreased amount of protein translation has been shown to occur if the repeats are extensive. DNA insertion and deletion are thought to be related to impaired function of DNA repair enzymes and polymerases in regions of perfect repeats. Domain 2 variants reported have from 91 to 216 amino acids in length. However, even longer variants are predicted by PCR of domain 2, including a large number of variants with a domain 2 size of 1.1 kb. These data suggest that domain 2 DNA is a "hot spot" for DNA recombination/mutation.

A method of producing amplified mutants and variants is described in Example 20. Specific variants or mutants Iowa isolate compared to NINC isolate domain 2 of the SEQ ID NO: 5 are shown in Table 1.

TABLE 1

Conservatively Modifed Mutants and Variants of SEQ ID NO: 5

| | | | | | | |
|---|---|---|---|---|---|---|
| Var 2 | MGSKVYIPYT | KCVGVKH..T | TTTTTTTTTT | TTTTTTTTTT | T........T | SEQ ID NO: 12 |
| Var 3 | MGSKVYIPYT | KCVGVKHTTT | TTTTTTTTTT | TTTTTTTTTT | T........T | SEQ ID NO: 13 |
| Var 12 | MGSKVYIPYT | KCVGVKHTTT | TTTTTTTTTT | TTTTTTTTTT | T........T | SEQ ID NO: 14 |
| Var 1 | MGSKVYIPYT | KCVGVKHTTT | TTTTTTTTTT | TTTTTTTTTT | TTTTTTTTTT | SEQ ID NO: 15 |
| Var 4 | MGSKVYIPYT | KCVGVKHTTT | TTTTTTTTTT | TTTTTTTTTT | T......... | SEQ ID NO: 16 |
| Var 11 | MGSKVYIPYT | KCVGVKHTTT | TTTTTTTTTT | TTTTTTTTTT | TTTTTTTTTT | SEQ ID NO: 17 |
| Var 9 | MGSKVYIPYT | KCVGVKHTTT | TTTTTTTTTT | TTTTTTTTTT | TTTTTTTTTT | SEQ ID NO: 18 |
| Var 10 | MGSKVYIPYT | KCVGVKH... | .......... | .......... | .......... | SEQ ID NO: 19 |
| NINC | MGSKVYIPYT | KCVGVKHTTT | TTTTTTTTTT | TTTTTTTTTT | TTTTTTTTTT | SEQ ID NO: 20 |
| Var 2 | .......... | .......... | .......... | .......TTT | T......... | |
| Var 3 | .......... | .......... | .......... | .......TTT | T......... | |
| Var 12 | .......... | .......... | .......... | .......TTT | T......... | |
| Var 1 | .......... | .......... | .......... | .......TTT | T......... | |
| Var 4 | .......... | .......... | .......... | .......... | .......... | |
| Var 11 | TTTTTTTTTT | TTTTTTTTTT | TTTTTTTTTT | TTTTKKPTTT | T......... | |
| Var 9 | TTTTTTTTTT | AT........ | .......... | .......TTT | T......... | |
| Var 10 | .......... | .......... | .......... | .......... | .......... | |
| NINC | TTTTTTTTTT | TTTTTTTTTT | TTTTTTTTTT | TTTTTTTTTT | TTTTTTTTTT | |
| Var 2 | .......... | .......... | .......... | .......... | .......... | |
| Var 3 | .......... | .......... | .......... | .......... | .......... | |
| Var 12 | .......... | .......... | .......... | .......... | .......... | |
| Var 1 | .......... | .......... | .......... | .......... | .......... | |
| Var 4 | .......... | .......... | .......... | .......... | .......... | |
| Var 11 | .......... | .......... | .......... | .......... | .......... | |
| Var 9 | .......... | .......... | .......... | .......... | .......... | |
| Var 10 | .......... | .......... | .......... | .......... | .......... | |
| NINC | TTTTTTTTTT | TTTTTTTTTT | TTTTTTTTTT | TTTTTTTTTT | TTTTTTTTTT | |
| Var 2 | .......... | .....TTTTT | TTTTTTTTTT | TTTTTTTTTT | TTTTTTTTTT | |
| Var 3 | .......... | .....TTTTT | TTTTTTTTTT | TTTTTTTTTT | TTTTTTTTTT | |
| Var 12 | .......... | .....KPTTT | TTTTTTTTTT | TTTTTTTTTT | TTTTTTTTTT | |
| Var 1 | .......... | .....TTTTT | TTTTTTTTTT | TTTTTTTTTT | TTTTTTTTTT | |
| Var 4 | .......... | ......TTTT | TTTTTTTTTT | TTTTTTTTTT | TTTTTTTTTT | |
| Var 11 | .......... | .....TTTTT | TTTTTTTTTT | TTTTTTTTTT | TTTTTTTTTT | |
| Var 9 | .......... | .....TTTTT | TTTTTTTTTT | TTTTTTTTTT | TTTTTTTTTT | |
| Var 10 | .......... | .......... | ..TTTTTTTT | TTTTTTTTTT | TTTTTTTTTT | |
| NINC | TTTTTTTTTT | TTKKPTTTTT | TTTTTTTTTT | TTTTTTTTTT | TTTTTTTTTT | |
| Var 2 | TTTKKPTTTT | TTTTTTTTKK | PTTTTTATTT | TTTSETESVI | KPDEWCWLE | |
| Var 3 | TTTKKPTTTT | TTTTTTTTKK | PTTTTTATTT | TTTSETESVI | KPDEWCWLE | |
| Var 12 | TTTKKPTTTT | TTTTTTTTKK | PTTTTTATTT | TTTSETESVI | KPDEWCWLE | |
| Var 1 | TTTKKPTTTT | TTTTTTTTKK | PTTTTTATTT | TTTSETESVI | KPDEWCWLE | |
| Var 4 | TTTKEPTTTT | TTTTTTTTKK | PTTTTTATTT | TTTSETESVI | KPDEWCWLE | |
| Var 11 | TTTKKPTTTT | TTTTTTTTKK | PTTTTTATTT | TTTSETESVI | KPDEWCWLE | |
| Var 9 | TTTKKPTTTT | TTTTTTTTKK | PTTTTTATTT | TTTSETESVI | KPDEWCWLE | |
| Var 10 | TTT...TTTT | TTTTTTTTKK | PTTTTTATTT | TTTSETESVI | KPDEWCWLE | |
| NINC | TTTTKPTTTT | TTTTTTTTKK | PTTTTTATTT | TTTSETESVI | KPDEWCWLE | | wherein
F = phe
L = leu
S = ser
Y = tyr
Z = OCH or AMB
C = cys
Z = OPA
W = trp

TABLE 1-continued Conservatively Modifed Mutants and Variants of SEQ ID NO: 5

```
R = arg
g = gly
E = glu
a = asp
A = ala
V = val
M = met
I = ile
T = thr
P = pro
H = his
Q = gln
N = asn
K = lys
```

The NINC sequence seen in the Table 1, corresponds to amino acids 192–392 of the SEQ ID NO: 6. Iowa variant domain 2 sequences (SEQ ID NOs. 12–19) as seen in Table 1 correspond to amino acids 309–524 of SEQ ID NO: 5. Mutations or variations of the GP900 protein thus occur between isolates and within a given isolate.

II. Treatment

Therapy and Prophylaxis

The therapy of cryptosporidiosis in humans and animals is conducted by administration of the recombinant GP900 protein or analogue of the invention to patients with cryptosporidiosis to effectively reduce their symptomatology.

A method for therapeutic treatment, retardation, or inhibition of Cryptosporidium infection comprises administering to a subject in need of such treatment an amount of a recombinant GP900 protein, or an engineered analogue thereof, prepared according to the invention, effective to inhibit the existing clinically apparent Cryptosporidium infection.

A method of prophylaxis of Cryptosporidium infection comprises administering to a subject in need of such treatment an amount of a recombinant protein, or an engineered analogue thereof, prepared according to the invention, effective to provide protection against the invasion of Cryptosporidium and establishment of clinical infection.

Treatment of Cryptosporidiosis in AIDS Patients and Other Immunocompromised Subjects In AIDS patients *Cryptosporidium parvum* may cause a devastating disease for which there is no treatment. Understanding of the organism and the pathophysiology of the disease it produces, and development of treatment, are very important steps in the treatment of Cryptosporidium infection.

Currently, no pharmaceuticals are available for the prevention or treatment of cryptosporidiosis. Over 95 drugs have been tested in vitro or in vivo, but, none of these drugs has been shown to be effective. One of the therapeutic approaches for treatment of chronic cryptosporidiosis according to the invention is the use of recombinant protein or engineered analogues of the protein antigen of the invention which may be given orally to humans to provide a therapeutic benefit.

As the number of AIDS patients increases, the number of cryptosporidiosis cases will also rise resulting in a critical need for effective therapy and prophylaxis. The current invention provides an effective treatment and prophylaxis against the cryptosporidiosis infection.

Recombinant domain 1 and domain 3 proteins of the invention were produced as described in Example 16. Open reading frame (ORF) sequence(s) is engineered for in frame expression as a thioredoxin fusion protein in the Invitrogen vector pTrxFus, or any other suitable vector. The Invitrogen pTrxFus vector is used to create fusions to the C terminus of *E. coli* thioredoxin. There is a multiple cloning site which allows in frame fusion of foreign protein with thioredoxin. Between the thioredoxin and the foreign protein there is an enterokinase cleavage site. Enterokinase treatment permits the release of thioredoxin from the protein. pTrxFus DNA is digested with for example KpNI and XbaI and the intervening fragment is removed for example, by gel purification.

Domain 1 and domain 3 primers and sense and antisense for domain 1 and domain 3 (SEQ ID NOs. 21–24) were used to amplify the Iowa Cryptosporidium DNA. The sense primers have a KpN1 site and the antisense primers have an XbaI site engineered into the 5' end of the oligonucleotides. These enzymes are used to digest the amplified DNA so that it could be inserted directionally and in frame into the KpnI/XbaI restriction digested pTrxFus. Then, the vector, such as pTrxFus, containing the sequence relevant portion of the protein, is used to transform competent *E. coli* cells. Ampicillin resistant transformants are then analyzed for plasmid DNA by restriction with KpNI-XbaI and by sequence for the presence, orientation and reading frame of the gene or gene fragment. Clones containing the gene or gene fragment are induced for expression of the relevant fusion protein, such as, for example, domain 3-thioredoxin a 33kD protein. Conditions for optimal production of soluble protein in *E. coli* were assessed. Domain 1 and 3 were wholly soluble as the pellet fraction showed no fusion protein.

Fusion protein may be purified by osmotic shock or heat treatment of cell lysates to produce highly purified fusion protein. The fusion protein is advantageously cleaved with enterokinase at a cleavage site comprising 4 asparagine and 1 lysine sequence.

Production of a GP900 protein or protein fragments is accomplished in multiple procaryotic or eukaryotic cells, including baculovirus, insect cells, yeast and mammalian cells. GP900 protein or protein fragments are purified by any suitable method known in the art, as described in Examples, and for example by incorporation of histidine and purification by nickel chromatography, and heat treatment of thioredoxin fusion protein with subsequent harvesting of soluble protein.

Formulations suitable for the administration of polypeptides such as those described herein are known in the art. Typically, other components stimulatory of immune response may be added as well as fillers, coloring, and the like.

III. Diagnosis/Detection

An important part of this invention is a method of diagnosing Cryptosporidium infection or detection of Cryptosporidium in the tissue samples or in the environment. The detection method for environmental samples comprises contacting such a sample with the invention for purposes of detecting Cryptosporidium.

The diagnostic method comprises contacting a body fluid or tissue with the invention for purposes of detecting the presence of Cryptosporidium.

Examples of body specimens are stools and other liquid or solid body output or tissue samples obtained from a subject. Examples of body fluids are blood, serum, saliva, urine, and the like. Methods for the preparation of the body substance and the body fluid are standard in the art and are described, for example in *Manual of Clinical Microbiology*, Chapter 8, "Collection, Handling and Processing of Specimens", 4th edition, Eds, Lennette, E. H., Balows, A., Hausler, W. J. and Shadorny, A. J., American Society for Microbiology, (1986)), and examples of environmental samples include water, soil and foods grown in the environment.

Qualitative and Quantitative Detection of Cryptosporidium Formulations and Kits

For qualitative and quantitative determination of the presence of the Cryptosporidium infection and environmental contamination, a kit for the diagnosis/detection of Cryptosporidium is used. The kit comprises the peptide, polypeptide, glycoprotein, functional mutant, variant, analogue or fragment thereof and a means for detecting the competitive replacement of native GP900 with the invention.

Figure 3:
FIG. 3 shows the MAb 7B3 indirect immunofluorescence detection of GP900 present on the surface and shed from the surface of a motile sporozoite.
Figure 4:
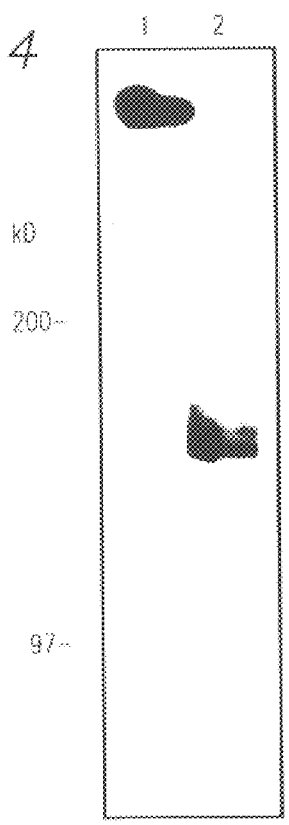
FIG. 4 depicts the immunoelectronmicrographic localization of GP900.

The kit is utilized for the detection of GP900 an antibody to GP900 produced in a subject that is afflicted with cryptosporidiosis and GP900 present in environmental samples. The detection method utilizes the principle of displacement of native antigen by the labeled peptide, polypeptide, glycoprotein of the invention as is described in the teaching of radioimmunoassay. Complexing is detected by staining, radiography, immunoprecipitation or by any other means used in the art and suitable for these purposes.

The kit is utilized for the detection of endogenous antibodies/antigens/DNA/RNA produced by a subject that is afflicted with cryptosporidiosis and Cryptosporidium antigens/DNA/RNA present in the environmental samples. Even at the early stages where the parasite is commencing invasion of a subject's cells, some amount of the Cryptosporidium antigen or the specific antibody detectable in serum. The kit detects either the antigen with the polyclonal antibodies or the presence of the anti-Cryptosporidium antibody with the antigen. The complexing immunoreaction is detected by staining, radiography, immunoprecipitation or by any other means used in the art and suitable for these purposes. In addition to the above, the kits may also comprise a control compounds, anti-antibodies, protein A/G, and the like, suitable for conducting the different assays referred to above.

Utility

The current invention provides an effective treatment and prophylaxis against the cryptosporidiosis infection and means of detection of the parasite and diagnosis of infection.

The current invention provides means for suitable detection or diagnosis of *Cryptosporidium parvum* species and isolates and cryptosporidiosis or, for a therapeutic use of recombinant or otherwise modified or engineered variants, analogues or fragments of GP900 produced according to the invention.

The following examples describe procedures used to prepare the compounds of the invention and the proof of concept for competitive inhibition. They are illustrative only and any modification using methods known in the art is intended to be included. The following examples are not to be considered in any way limiting.

EXAMPLE 1

*Cryptosporidium parvum* Parasites

This example illustrates the protocol used for isolation of *Cryptosporidium parvum* parasites.

Oocysts of the Iowa, NINC and AUCP-1 isolates of *Cryptosporidium parvum* were passaged through neonatal calves at the Animal Resources Services, University of California, Davis or obtained from a commercial source (Pat Mason) and the oocysts were purified and encysted. The detailed protocol is described in *Infect. Immun.,* 61:4079 (1993). Oocysts containing sporozoites were solubilized, resolved by SDS-PAGE and subjected to immunoblotting, according to *Infect. Immun.,* 60:5132 (1992).

EXAMPLE 2

Preparation of Murine Anti-Sporozoite Monoclonal Antibodies

This example describes the procedure used for preparation of murine anti-sporozoite monoclonal antibodies.

Polyclonal Antibodies 10 week-old female BALB/c mice were immunized four times intraperitoneally with approximately $5\times10^5$ sonicated $10^5$ *Cryptosporidium parvum* oocysts. The polyclonal antibody fraction of the ascites which was shown to react with the *Cryptosporidium parvum* sporozoite surface, the oocyst surface, and/or with internal antigens of the oocysts, was assessed by an IFA as described in *Infect. Immun.,* 60:5132 (1992).

Monoclonal Antibodies

For monoclonal antibody production, mice treated as above were immunized intravenously with the supernatant from sonicated *Cryptosporidium parvum* oocysts three days before fusion as described in *J. Immunol.,* 123:1548 (1979) and *J. Parasitol.,* 68:1029 (1982). Hybridoma supernatants were used as the source of antibodies.

Six sporozoite monoclonal antibodies were obtained. The 10C6, 7B3 and E6 monoclonal antibodies were determined to react with GP900. The supernatants of the corresponding hybridoma cultures were used for immunofluorescence assay (IFA) studies and Western blots.

Using the same protocol, infected MDCK cells were used to immunize mice and 3 MAbs to GP900, namely M2, M10, M24 were produced.

EXAMPLE 3

Detection of Trails of GP900 Deposited on Poly-L-lysine

In order to determine whether GP900 was shed by the Cryptosporidium sporozoite in the absence of a specific antibody, living sporozoites were allowed to glide on poly-L-lysine coated microscopic slides. Slides were fixed in formalin and GP900 detected by incubation with MAb 7B3 followed by fluorescein labeled anti-mouse second antibody Results are seen in FIG. 3. MAb 7B3 had previously (data not shown) been shown to detect only one protein, GP900, in sporozoites.

In FIG. 3, the sporozoites were shown to be surrounded by GP900 which was shed posteriorly as the sporozoites glided on the poly-L-lysine coated slides. This reaction occurred in the absence of specific antibody which was added only for detection purposes after fixation of the sporozoites and is analogous to the circumsporozoite deposition and localization of the protein of malaria which contains the binding ligand for binding to the hepatocyte adhesion receptor prior to invasion of the hepatocyte.

EXAMPLE 4

Production of Polyclonal Anti-GP900

This example describes the procedure used for preparation of anti-GP900 polyclonal antibodies.

The Triton X-100 (1%) soluble fraction of $2 \times 10^8$ oocysts was immunoprecipitated with MAb10C6. A >900 kD MW species was identified in gels stained with Coomassie blue in water and excised. Frozen gel containing $2 \times 10^7$ oocyst/sporozoites was pulverized and emulsified in 150 µl PI of PBS and 150 µl complete Freund's adjuvant (CFA) for intraperitoneal (IP) immunization of mice.

Subsequently, the mice were immunized (IP) three times with the same antigen dissolved in incomplete Freunds adjuvant (ICFA) at approximately 2 week intervals. The anti-GP900 antibody at a dilution of 1:5000 recognized GP900 on Western blots.

EXAMPLE 5

Production of Polyclonal Antibody Against Ag4 and S34 Fusion Proteins

This example describes the procedure used for preparation of the anti-Ag4 and anti-S34 fusion protein polyclonal antibodies.

Lysogens were produced from the Ag4 and S34 gt11 clones. Cell lysates and purified protein were made using a protocol and reagents obtained from Promega. Purified fusion protein were emulsified in CFA and injected into rabbits. These injections continued at two week intervals with the substitution of ICFA. Rabbits were sacrificed at the end of 3 months and the antibody was assayed by Western analysis to verify that the antibody recognized a protein >900 kD.

The β-galactosidase and Ag4-β-galactosidase fusion proteins were purified essentially as described by Promega except that the buffering system used was phosphate buffered saline (PBS) pH 7.4. The purified fusion proteins were then coupled to CNBR sepharose using standard techniques. The antibodies to Ag4-β-galactosidase were depleted by passaging serum over a CNBR sepharose column coupled to β-galactosidase alone. The flow through fraction was applied to a CNBR sepharose column coupled to the purified Ag4 fusion protein. Antibodies directed against the Ag4 portion of the fusion protein were eluted in 0.1 M glycine at a pH of 2.4 and immediately neutralized in 200 µl of 2M Tris, pH 7.4. All affinity purified antibodies reacted with the fusion protein and the respective Cryptosporidium protein but not other E. coli proteins.

S34 was subcloned in GST and coupled to a column CNBR sepharose. Antibodies to S34-β-galactosidase were passed over this column. Antibodies directed against the S34 portion of the fusion protein were eluted in 1M Na thiocyanate and desalted and concentrated.

EXAMPLE 6

Production and Affinity Purification of Polyclonal Antibody Against Domain 1- and Domain 3 Fusion Proteins and Control Antibody This example describes production and purification of antibodies against domains 1- and 3 fusion proteins.

Purified domain 1- and domain 3 thioredoxin were prepared as described in Example 16. Two to three µg of fusion protein after purification were emulsified in CFA or ICFA and and injected at two week intervals. Rabbits were sacrificed at 3 months and the antibodies were assayed by immunoblot analysis to verify that they recognized GP900.

Polyclonal rabbit antisera from an unimmunized rabbit was evaluated for reactivity against Cryptosporidium antigens at a 1:1000 dilution on immunoblot and found to be free of reactivity. One ml of polyclonal rabbit antisera, anti-domain 1- or anti-domain 3 antisera was diluted with an equal volume of 100 mM Tris (pH 8.0) and passed through a 1 ml protein A bead column 2 times. After washing with 100 mM and 10 mM Tris (pH 8.0), the column was eluted with 100 mM glycine (pH 3.0) in a stepwise fraction. Aliquots of 500 µl were collected into 50 µl of 1.0 M Tris, pH 6.0. Antibody concentration was determined by absorbance at 280 nm and integrity of the Ig was verified by SDS-PAGE. Positive control antibody, HBC Ig 40529 has been previously described in *Infect. Immunol.*, 61:(10); 4079 (1993).

EXAMPLE 7

Western Analysis

This example describes the Western analysis method used to identify the molecular targets of antibodies.

Oocysts ($10^6$ lane) were solubilized in denaturing sample buffer containing 5% βME (β-mercaptoethanol), resolved by SDS-PAGE and subjected to immunoblotting according to *Infect. Immunol.*, 60:532 (1992). Proteins were visualized after incubation with primary antibody with $^{125}$I anti-rabbit or anti-mouse IgG conjugated with horseradish peroxidase or alkaline phosphatase followed by calorimetric or chemiluminescent development.

EXAMPLE 8

Southern Hybridization and Northern Blot Analysis

This example describes the Southern hybridization method used for testing described in FIG. 6 and northern blot analysis of GP900 used for testing described in FIGS. 7 and 8.

A. Southern Hybridization

DNA was purified from $1 \times 10^9$ Cryptosporidium parvum oocysts as described in Example 1. DNA was digested with the restriction enzymes according to procedures provided by the manufacturer Promega. Digested DNAs were subjected to electrophoresis in 0.8% agarose gels in 1×TAE or 0.5× TBE. The gel was blotted to a nylon membrane (Hybond N+, Amersham) per manufacturer's instructions. The probe was labeled with $^{32}$P-ATP and hybridized to the membrane by methods known in the art. Results are seen in FIG. 6 where Lanes 1–4 show Iowa isolate DNA and Lane 5 shows AUCP isolate DNA. Lane 1, EcoRI digest; Lane 2, Bgl II digest; Lane 3, Hinf III digest; Lanes 4 and 5, Hinf I digest.

B. Northern Blot Analysis mRNA was purified from MDCK cells, or MDCK cells infected with sporozoites at a ratio of 1 oocyst/1 MDCK cell, harvested at 24 and 48 hours using guanidinium thiocyanate and oligo-dT cellulose isolation (Ambion mRNA purification kit, Albion, Inc., Austin, Tex.). Ten µg of poly-A RNA was separated on a formamide gel, transferred and hybridized as described for Southern hybridization. The Northern blot was probed with $^{32}$P-αdATP labeled domain 3 DNA and washed under stringent conditions.

EXAMPLE 9

Surface Radioiodination and Immunoprecipitation of Cryptosporidium Sporozoite Proteins This example describes the methods used for surface radio-iodination and immunoprecipitation of Cryptosporidium sporozoite proteins.

Oocysts were bleached, encysted and separated from sporozoites prior to iodination of the sporozoite surface and immunoprecipitation of surface proteins as previously described in *Infect. Immun.* (1993).

A membrane pellet was prepared by centrifuging $1.1 \times 10^7$ sporozoites per ml NETT (0.15 M NaCl, 5 mM EDTA, 0.5 M Tris, 0.5% Triton X-100, pH 7.4) at 100,000×g for 1 hour at 40° C. An aliquot of membrane proteins in 2% SDS 5% p-sample buffer was prepared for total sporozoite surface protein analysis. Aliquots of membrane proteins extracted in 2% SDS were diluted with 9 volumes NETT plus 1% high quality bovine serum albumin (BSA) obtained from Sigma; 1 volume 1% Triton X-100; proteinase inhibitors and either MAb 10C6 or anti-GP900 were added for overnight incubation. Protein A Sepharose 4B beads were added to immobilize the immunoprecipitated proteins. Parasite proteins were solubilized in 2% SDS sample buffer containing β-mercaptoethanol. Samples were boiled 5 minutes and separated by 5–15% gradient SDS-PAGE.

EXAMPLE 10

Immunoelectronmicroscopic Localization of GP900 in *Cryptosporidium parvum*-Infected Rat Intestinal Tissue This example describes the immunoelectronmicroscopic methods used for localization of GP900 antigen in *Cryptosporidium parvum* infected rat intestinal tissue.

Small pieces of terminal ileum were obtained from an immunosuppressed rat experimentally infected with a lamb isolate of the parasite. Tissue samples were fixed with 2% formaldehyde-0.1% glutaraldehyde in PBS for 2 hours at room temperature. They were washed in PBS, dehydrated in ethanol at −20° C., and embedded in LR White obtained from London Resin Co. After polymerization at 37° C. for 5 days, thin sections were cut with a diamond knife and collected on nickel grids coated with formvar. They were floated for 30 minutes on 2.5% nonfat dry milk in PBS (PBSM) and then transferred to anti-GP900 mouse ascites obtained as described in Example 2 and diluted 1:20 in PBSM for 1 hour at room temperature. After the grids were washed in PBS, they were floated on rabbit anti-mouse immunoglobulin serum obtained from Tago, diluted 1:200 in PBSM, for 1 hour at room temperature, and then transferred for 1 hour to 8 nm protein A-coated beads diluted 1:10 in PBSM.

Thin sections were stained with 3% uranyl acetate in water and observed with a Hitachi H600 electron microscope (EM) FIG. 5. EM photographs were also obtained using undiluted MAb IRM hybridoma culture medium and a 1:25 dilution of protein A coated gold beads. Control sections were incubated with unrelated monoclonal and polyclonal antibodies.

EXAMPLE 11

Cloning and Sequencing of a GP900 Locus

This example illustrates the procedure used for cloning and sequencing of a GP900 locus.

The purification and initial characterization of the S34 clone and the description of the restriction fragment genomic expression library of the NINC isolate from which it was isolated have been described in (*Infect. Immunol.*, 60:2343 (1992)). The Ag4 clone was isolated from the same library as an expression clone which reacted with polyclonal anti-GP900 antibody. The inserts of the S34 and Ag4 clones were subcloned into BlueScript obtained from Stratagene and sequenced in both directions using Sequenase Version 2.0 DNA Sequencing Kit (UBC) or cycle sequencing (New England Biolabs).

DB8, a 3154 bp insert, which contained the sequences of both S34 and Ag4 was identified by a double of screen of the library using these DNA inserts. PCR amplification products generated from the ends of DB8 and subsequent clones were used to screen the library to identify new clones which extend the sequence of the NINC isolate GP900 3' and 5'.

The Iowa sequence was established. The complete encoding sequence of the Iowa isolate GP900 gene, which shows high homology to the NINC gene, was also cloned and sequenced. The sequence was established by PCR using sequencing primers form the NINC sequence and template DNA of the Iowa isolate with subsequent cloning of overlapping sequences in pFusTrx or Bluescript for sequencing. At least 2 independent clones were sequenced in both directions to identify and correct PCR errors. The 5' region was sequenced from a 2.2 kb BamH1 fragment cloned into Bluescript.

The GP900 reading frame was verified by the inframe expression of S34 and Ag 4 as β-galactosidase fusion proteins and domains 1 and 3 as thioredoxin fusion proteins. All 4 fusion proteins elicited antibodies to GP900 when used to immunize animals (Data not shown). The FastA and blastp programs of GenBank were used to perform homology searches of the Swiss Protein database and showed homology of GP900 to mucin-like proteins.

EXAMPLE 12

In vitro Inhibition of Sporozoite Invasion and Intracellular Development

This example describes the methods used for determination of in vitro inhibition of sporozoite invasion/intracellular development.

Oocysts were used to inoculate confluent Madin Darby Canine Kidney (MDCK) cell monolayers for in vitro inhibition assays of sporozoite invasion and intracellular development as previously described in (*Inf. Immun.*, 61:4079 (1993)) with the following modifications. Chamber slide wells obtained as tissue culture chamber slides from Nunc Inc., Napersville, Ill., containing $10^5$ MDCK cells were overlaid with 400 1 RPMI medium containing $1.5 \times 10^5$ oocysts and antibody or colostrum samples to be tested for inhibitory capacity. Each experimental data point was an average of the number of parasite nuclei counted per 200–300 cell nuclei from each of three independently infected chamber wells. Antisera and controls were used after complement inactivation at 55° C. for five minutes.

Controls included hyperimmune bovine colostrum 40529 Ig (HBC Ig) raised against Cryptosporidium oocysts and sporozoites and SHAM-HBC raised against a herd vaccine at ImmuCell Corp, Portland, Me.

EXAMPLE 13

Dose Response Relationship of Affinity Purified Anti-S34 Antibody and Inhibition of Invasion and Intracellular Development In vitro This example describes the method used for determination of the dose-response relationship of polyclonal antibodies in vitro with regard to inhibition of sporozoite invasion and intracellular development.

Affinity purified anti-S34 antibody as described in Example 5 was used to determine the dependence of inhibition of invasion/intracellular development on the quantity of antibody added to the in vitro MDCK assay system as described in Example 12. The antibody, at concentrations of 10, 50, 100 and 500 µg/ml in RPMI, was incubated with encysted oocysts on MDCK cell monolayers for two hours. The wells were washed out and refilled with RPMI.

Control wells contained equal amounts of oocysts and RPMI alone, S34-GST at 100 nM, anti-oocyst/sporozoite antibody at a 1:40 dilution and HBC Ig 40529 at a 1:40 dilution. As described in FIG. 9 invasion/intracellular development was reduced to less than 7% of control in the presence of 500 µg/ml affinity purified anti S34.

EXAMPLE 14

Inhibition of Adhesion by Anti-S34-β-Galactosidase Antibody in the Caco-2 Adhesion Assay In vitro This example describes the method used for determination in vitro of the mechanism by which the polyclonal antibody prevents inhibition of sporozoite invasion and intracellular development.

Caco-2 cells were grown in monolayers and fixed with paraformaldehyde. Sporozoites were isolated, incubated with 1:50 dilutions of anti-β-galactosidase, anti-S-34-β-galactosidase, anti-Ag4-β-galactosidase and HBC Ig 40529 prepared as described in Example 15. Adhesion was determined using an ELISA assay which had previously been validated by correlation with results determined by electronmicrographic assessment of adhesion/inhibition of adhesion.

Anti-S34-β-galactosidase and HBC Ig 40529, the positive control antibody, exhibited an optical density (O.D.) which was 50% of the negative control antibody, anti-β-galactosidase. Anti-Ag4 did not have significant inhibitory activity relative to the control antibody.

EXAMPLE 15

Inhibition of Cryptosporidium Invasion and Intracellular Development in MDCK cells with MAb 10C6

This example describes studies performed to detect inhibition of Cryptosporidium invasion and intracellular development in vitro using monoclonal antibodies.

Cryptosporidium oocysts of the AUCP-1 isolate were encysted and three sporozoite monoclonal antibodies, MAb 10C6, 7B3 and E6, were prepared as described in Example 2. To assess the effect of specific antibodies on sporozoite invasion, MAb 10C6, a monoclonal antibody detecting GP900, was incubated with viable sporozoites for 30 minutes prior to addition to monolayers of MDCK cells.

Sporozoite invasion and intracellular development in MDCK cells was scored at 16 hours after fixation of MDCK cells in formalin and staining with Giemsa. Both invasion and intracellular development were found to be inhibited by >95% compared to the control antibody. Sequential observation of viable, unfixed Cryptosporidium sporozoites by differential phase contrast microscopy after addition of MAb 10C6 revealed initial reactivity of the MAb with the surface followed by shedding of the sporozoite surface coat and production of a tail-like precipitate. At 30 minutes, shedding was complete or sporozoites were immobile and clumped.

EXAMPLE 16

Purification of Recombinant GP900 Proteins

This example describes the purification procedure for GP900 proteins.

Iowa oocysts ($5\times10^8$) were excysted at 37° C. for two hours and pelleted at 4,000×g for 10 minutes at 4° C. The supernatant was aspirated and proteinase inhibitors were added to it to a concentration of pefabloc (AEBSF) 1 nM, leupeptin 20 µM, iodoacetamide 10 mM, PMSf 2 mM. The supernatant was concentrated by ultrafiltration to 350 µl (14.2×) (Centricon 10, Amicon). Silver stained SDS-PAGE gel of 10 and 20 µl aliquots revealed equal amounts of 47 kD, 120 kD and >900 kD proteins. The >900 kD protein was purified by ultrafiltration and (Centricon 100) and the concentration determined by silver stain and comparison to transferrin standards.

EXAMPLE 17

In vivo Inhibition of Cryptosporidium Infection in Mice Challenged with Cryptosporidium Oocysts with Anti-S34-β-Galactosidase and anti-antigen for β-Galactosidase Polyclonal Antibodies This example describes the method used for determination of the in vivo inhibition of Cryptosporidium infection of mice challenged with Cryptosporidium oocysts and treated with specific anti-S34-β-galactosidase and anti-antigen 4-β-galactosidase (FIG. 10) polyclonal antibodies.

Anti-β-galactosidase, anti-S34-β-galactosidase, anti-Ag4-β-galactosidase and HBC Ig 40529 were tested for inhibitory activity in a neonatal mouse model of Cryptosporidium infection using GCH-1 obtained from an NIH repository.

Three experiments were performed and the data pooled. In each experiment 5 neonatal mice per group were infected with Cryptosporidium and were fed either 20 µl control PBS, 20 µl of the 3 rabbit antibodies or 20 µl of a 1:5 dilution of HBC Ig 40529 twice a day. A positive pharmacological control substance, 500 mg/kg/d of paromomycin, in dosage approximately 15× the dosage given to human AIDS patients for cryptosporidiosis, was given to mice in 2 experiments. Infection was scored as the mean number of oocysts shed per day during a 5 day collection period.

Anti-GST antibody (1 rabbit) and anti-GST-S34 antibodies (2 rabbits) were made as described in Example 5, except that the fusion protein was glutathione-S-transferase in the pGEX vector. A challenge protection experiment was researched in which antibodies were assayed in vivo in groups of 7 CDI neonatal mice challenged with $10^4$ oocysts on day 6. Oocyst output was scored in Sheather's solution and is expressed as $10^5$/ml. Antisera were diluted 1:2 in 50 mM NaHCO3. FIG. 10 is a graph representing the amount of excretion of Cryptosporidium oocysts per day in mice treated with phosphate buffered saline (bar 1); anti-β-galactosidase (bar 2); anti-Ag4-β-galactosidase (bar 3); anti-S34-β-galactosidase (bar 4); 1:5 HBC Ig 40529 (bar 5); and paromomycin (bar 6). As seen in FIG. 10, anti-S34 (bar 4) reduced the oocysts shed by about 50% relative to control PBS (bar 1) and anti-β-galactosidase antibody (bar 2).

EXAMPLE 18

Polymorphisms in GP900

This example illustrates the method used to prepare mutant or variant products.

Genomic DNA from the Iowa and several other strains was subjected to PCR amplification using primers which were situated outside of domain 2, in the distal region of domain 1 and the proximal region of domain 3. Three prominent bands of different sizes were observed when the PCR products were visualized by ethidium staining of a gel in all of these strains. As a control for TAC polymerase, DB8 DNA was also amplified by the polymerase chain reaction. Only a 700 bp amplification product from DB8 was detected indicating that the multiple bands were a product of amplification of sequences present in the genomic DNA, and were not an artifact of the PCR process.

Two of the amplification product bands were cloned into sequencing vectors and 4 clones from each of the products were sequenced to determine their relationship to the NINC domain 2 sequence (Table 1). All 8 sequences had an open reading frame indicating that they were portions of DNA which could be the blueprint for a GP900 protein. All 8 sequences appeared to have in-frame (multiples of 3) DNA deletions with respect to the NINC sequence. All 8 coded for a domain 2 which had conservation of the threonine rich regions, but all 8 differed from each other. The DNA data indicate that mutation in domain 8 is common. The conservation of threonines and the in-frame nature of all 8 clones indicate that there are selection pressures acting at the level of the protein (presumably production of a functional protein which will allow for invasion and propagation) which determine which genotypic variants are maintained in a strain. Results show that there are mutants of GP900 which are maintained in an isolate's gene pool, presumably as variant alleles at a single locus in haploid stages of the organism.

EXAMPLE 19

Preparation of Recombinant Domain 1 and Domain 3

This example describes the preparation of recombinant S34, Ag4, domains 1- and 3.

The oligonucleotide primers were synthesized at the Biomedical Research Center, University of California, San Francisco. A sense oligonucleotide (SEQ ID NOs: 21 and 22) are comprised of a KpnI restriction enzyme recognition site at the 5' end followed by coding sequence for the 5' end of the domain 1 sequence. The sense oligonucleotide for domain 3 is comprised of a KpnI restriction site at the 5' end followed by coding sequence for the 5' end of the domain 3 sequence. The anti-sense oligonucleotide for domain 1 is comprised of an Xbal sequence at the 5' end followed by the antisense coding sequence of the 3' end of the domain 1 sequence. The antisense oglionucleotide for domain 3 is comprised of an Xbal sequence of the 5' end followed by the anti-sense coding sequence of the 3' end of the domain 1 sequence. When used as a pair of PCR amplification oligonucleotides, these oligonucleotides allowed the amplification from genomic Cryptosporidium DNA of the entire domain 1 and domain 3 sequences with Kpn 1 and Xba I sequences at the 5' and 3' ends respectively.

The oglionucleotide sequences were designed so that after Kpnl and Xba I digestion of the amplification product, the resultant fragment could be introduced in a directional manner into pTrxFus which was cut with Kpnl/XbaI. Amplified and restricted DNA was visualized on a 0.8% agarose-1XTAE gel using ethidium bromide. The amplified and endonuclease restricted band was excised from the gel and purified using a glass bead technique (Gene-Clean).

pTrxFus was also digested with the enzymes KpnI and Xba I, enzymes uniquely present in the sequence in the poly linker, and the small intervening sequence was removed by gel purification as noted above. pTrxFus and domain 1 or domain 3 DNA, prepared in this manner, at 1:1 and 1:5 molar ratios were ligated overnight at 14° C. in the presence of ligation buffer and T4 DNA ligase at a concentration of 50–250 ng insert DNA/ 10 $\mu$l.

G1724 chemically competent cells were made as described by Invitrogen. Three to five $\mu$l of ligation mixes and control mixes were introduced into separate tubes of competent cells and the tubes were incubated on ice for 30 minutes. Tubes were incubated in a 42° C. heating block for 90 seconds and placed on ice for 2 minutes. Eight hundred $\mu$l of room temperature of enriched tryptone containing broth medium was added to each tube and the tube was incubated with shaking at 30° C. for 60 minutes. Twenty-five and 100 $\mu$l of each transformation mix was plated on RMG-Ampicillin transformation plates and the plates were incubated at 30° C. overnight.

Nitrocellulose membrane replicas of colonies were prepared from the transformation plates, the adherent cells lysed in alkaline solution and the DNA fixed to the membranes. Nitrocellulose membranes were hybridized with domain 1 and DNA 3 and positive colonies were purified. DNA was extracted from the relevant bacteria and the identity of the foreign DNA verified by restriction analysis and sequence analysis.

Purified colonies were grown in 1 $\mu$l aliquots for analysis. Growth conditions were varied with respect to time (2, 3, 4 hours) and the bacteria lysed for evaluation of soluble and insoluble proteins.

What is claimed is:

1. A fragment of the GP900 protein of *Cryptosporidium parvum*, wherein the fragment comprises domain 1, 2, 3, 4, or 5.

2. The fragment of claim 1, wherein the GP900 protein consists of SEQ ID NO:5 or SEQ ID NO:6.

3. The fragment of claim 2, wherein the fragment comprises a sequence selected from the group consisting of SEQ ID NO: 7, SEQ ID NO: 8, SEQ ID NO: 9, SEQ ID NO: 10, SEQ ID NO: 11, SEQ ID NO: 26, SEQ ID NO: 27, SEQ ID NO: 28, SEQ ID NO: 29 and SEQ ID NO: 30.

4. The fragment of claim 6, wherein the fragment comprises a sequence selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 and SEQ ID NO: 20.

5. A fragment of the GP900 protein of *Cryptosporidium parvum*, wherein the fragment competitively inhibits sporozoite or merozoite attachment or invasion in cultured cells, or inhibits specific binding of GP900 to cultured cells.

6. The fragment of claim 5, which comprises domain 3 of the GP900 protein.

7. The fragment of claim 6, comprising a sequence selected from the group consisting of SEQ ID NO: 22 and SEQ ID NO: 24.

8. The fragment of claim 6, which comprises domains 1, 2, and 3 of GP900.

9. The fragment of claim 5, which is a fragment of SEQ ID NO: 5.

10. The fragment of claim 5, which is a fragment of SEQ ID NO: 6.

11. The fragment of claim 5 which comprises SEQ ID NO: 7, SEQ ID NO: 8, SEQ ID NO: 9, SEQ ID NO: 10, SEQ ID NO: 11, SEQ ID NO: 26, SEQ ID NO: 27, SEQ ID NO: 28, SEQ ID NO: 29 and SEQ ID NO: 30.

12. A fusion protein comprising the fragment of any of claims 5–11, wherein the fusion protein inhibits sporozoite or merozoite attachment or invasion in cultured cells, or inhibits specific binding of GP900 to cultured cells.

13. A fragment of the GP900 protein of *Cryptosporidium parvum* wherein the fragment is capable of inducing the production of antibodies which ameliorate parasite infection when said antibodies are administered orally.

14. A fusion protein comprising the fragment of claim 13, wherein the fusion protein is caoable of inducing the production of antibodies which ameliorate parasite infection when said antibodies are administered orally.

15. A DNA comprising a sequence encoding the protein fragment of any of claims 1–11 or 13.

16. The DNA of claim 15, selected from the group consisting of SEQ ID NO: 1, SEQ ID NO: 2, SEQ ID NO: 3 and SEQ ID NO: 4.

17. An isolated or purified DNA encoding SEQ ID NO: 5 or SEQ ID NO: 6.

18. The DNA of claim 17 comprising SEQ ID NO: 1 or SEQ ID NO: 2.

19. A DNA comprising a sequence encoding the fusion protein of claim 12.

20. A DNA comprising a sequence encoding the fusion protein of claim 14.

21. A method for producing antibodies capable of inhibiting or ameliorating parasite attachment/invasion, comprising administering to a suitable host a purified GP900 protein of *Cryptosporidium parvum*, or the fragment of any of claims 5-11.

22. A method of treatment or prophylaxis of Cryptosporidium infections by competitive inhibition comprising steps:

a) preparing antibodies capable of inhibiting or ameliorating parasite attachment or invasion, using a purified GP900 protein of *Cryptosporidium parvum* or the fragment of any of claims 5-11; and b) administering said antibodies to a subject in need of such treatment or prophylaxis, wherein said antibodies competitively inhibit binding of a GP900 ligand protein or attachment or invasion of cells with Cryptosporidium.

* * * * *

SEQUENCE LISTING

```
(1) GENERAL INFORMATION:

(iii) NUMBER OF SEQUENCES: 30

(2) INFORMATION FOR SEQ ID NO:1:

(i) SEQUENCE CHARACTERISTICS:
          (A) LENGTH: 7334 base pairs
          (B) TYPE: nucleic acid
          (C) STRANDEDNESS: double
          (D) TOPOLOGY: linear
```

(ii) MOLECULE TYPE: DNA (genomic)

(xi) SEQUENCE DESCRIPTION: SEQ ID NO:1:

```
GATCCTGCAA TGTGGCAAAT GGTTACAACT ATAGCAGCAA TTTGTAGTAC TGCATGCCAG      60
AATGGTGGTA GAAGTAGTAG ACATTGCTGT AGAAAACATC ATTCTAGAAA GCATAAAAAA     120
GAAGCAGAAT TAAAAGATAC TAATAGCAAT AGCAGTAACA AGGAATCGAG CGACCTTAGT     180
GAAGCTCAAA TAGACCAAAC TCCCAAAGAA AGTTCCAACG ACAAGAACAA AAAATCAGGC     240
GAAAGGAAGT CAAACCAAAA TGATAATACT GTTAGTGGAA CTAAGTGGCA TGGAATAGAA     300
AAAAAAATTG CTACAATTAG AGGATTGAGA GACCTAGAAA GCACTGATTC GAACCTTGAT     360
GATGACGATG AATTAGCTGC ATCTAATACA TTGCCACAAG GAATAGGACA TCCAAGATAC     420
TCTGATATGG TCGAATTTCC GAGCGAAATT TCAGCATTTA ATGGTAATTC AAGGAATAGA     480
AGATATTTAG CAAAACAGGG AGTCTGTTAT GGAGCAAAGT TTTCAAAGAG CCCATTTGTA     540
GGTGGACTTT CTGCAGCAAG GAGAAGACCA TATAGTTGTC TCACCGAAAT GGCTGCCTAT     600
TTTTCTAACA TTGAGCCTCA AGACCAAAAT GACGTTATTG TTATGCTTCT AGCATGCAGA     660
AAGCTTGAAA ACAAATAGA GGAGCAACAG ACTGTAATGC AACTTTTAGA ACATGACCTA     720
AAAGAAGCGC AGTCTTTATT GAGGTTTCCC CCAGAATGGA GGTCTCTTAA TAATGAAGAA     780
ATATTGGGAC ATTCTCCACT TCCTACTGGA CAAATTCCAT CAACCAACGA TCCTCCATAC     840
GTCTCAAACC ATCCCAATAT TGAACCACCT TGGGTTAACA AAAGACCTAA GGATGGACTA     900
CCTTCAAGGG CACCTACAAA ATTATAGATT ATCAAGCTTT TCATAGTAGG TTCGAAAAAA     960
CATATACTTT AGTTCAATTT AATAGTTAAT CTCTTGCATT TCGTAATTAA ACATAATATC    1020
TATTCTCTTA GAGAGATACA ATTATTCATA TTATTTATTT TATTTCTATT AAACTCTATC    1080
GAACACAAAA ATATAAGACA TGTAAGAACC GCAACACTTA GATCTATACC ACATCCCCCC    1140
CCAAAAACTG CACTAGCCGG TAATCGAAAC CGGGCCGACG CAATGGGAAC GCGTCATCCT    1200
ACCACTAGAC TACTAGTGCT AACTGTCTCT CACCTGTCTA AATTAATTAA TTAATTAATT    1260
AAGGCGGCAA AAGCCAATCA CGCAATAATA ACGTTTTTGC CATTTCCCGC CTAAATGTGT    1320
GAGGTGATTT CTTATGTAAA AAATGACGTA TCTTTCAAGT CTAGCCCGTA TTGCACCCTA    1380
ATACATGCAA AGGATAATTA TACGTTGCTG TACGCGAGTG TATACTCTGT GAATAAAAAG    1440
TACATACATT AGAAAATCCT GGATAGAACA GAGAAGCATA TTGTGCATTT TGAATGCACT    1500
TGTGATAACT CTTGTTGGCA AGTAGTTTTT TTGTAATATA TTAACGCTAC ATCATAAGTT    1560
TCAGCTTAGG AAGTTCTTTT GCACAGGGTT TGAGCTAGCC TACTCTAGTG ATAAACAAAG    1620
GGTGGCTTGC TATTGACAAT TATCAGAGCC AAAAATTATA AATTCTAGGT GAAGTCAAAA    1680
ATCATGGTGA ACATTAAAGT GAGCTCATCG GCAATAGCCC TTGTGGCTGT TATTATGAAC    1740
CCACTTTTTT CACTTGCATT TAAATCGAGT AACCGATTAG AGATGAGAAT TGAATCATCT    1800
GGTGCAGTTT CAAATGAAAA ATTTGTAATC CCATCTCTCC CTTCAGATTT AGACCCAACA    1860
ACTTTCTTGC TTATTGATTC TACTGGCAAG AAATTCAGTC CATATACTGG TAAACATGCT    1920
GATGCATCAA CAACATCTAG TGCTTACAGT GCACCATTTG AGTTGGATGT TAGCGGAGTT    1980
CCAATCGAAC CAAATACAAG AAGAATGGTT GACCCAGTTT CTTTAATGCT TTTTGATAAT    2040
AGCACTGGCG TAATGTACGA TCCAAACACG AATTCTATTT TGGAAGGTTC AATTGCAGGT    2100
ATTAGAAGCG AATCTTGCAT TGTATCTGAA CTGAACTTTA CATCTACTAC TGGATTTACA    2160
ACGGACACAT CAATGAATTG GCCGGTAAGT ATCACAAGTG GTGAACTGAA GGATCCAAAC    2220
AAACAAGCTA CTATTTCTGG TTCAAGATCT TGTGGATGGA ACAAGGTTA TAGCATTGAT    2280
```

```
TCATCCACCG GGTTTAGAGT TGATTCTATC ACTGGTCTCC CAACTGATCC ATACCCTAAT    2340

TGTCCATTCA ACCCTGTCAC TGGAAATTTA GTCAGTAGGT CCACTGGTAA AACTATTCCA    2400

AACACTTATG CAGGTGTTTA TCGTTCTAAT GAGACTAAGA CCACTGAGCC TAGTGCAAAC    2460

ACCAACTTCT TGTTGGTAGA TCCTAAGATT AATGCTCCTT GTAATTCTGA GAACTCTTTT    2520

GAACAAGTCC AAATATTTGA TATGGGCAGT AAGGTATACA TTCCATACAC TAAATGTGTT    2580

GGAGTGAAAC ACACAACAAC AACAACAACA ACTACTACTA CTACTACTAC GACAACAACA    2640

ACAACAACGA CAACAACAAC AACTACTACA ACTACTACCA CTACTACTAC GACAACAACA    2700

ACTACTACTA CGACAACAAC AACAACAACT ACTACTACTA CTACAACCAC AACAACTACA    2760

ACCACGACAA CTACAACCAC AACCACAACT ACCAAGAAAC CAACAACAAC AACAACAACA    2820

ACAACTACTA CTACTACAAC AACAACAACA ACAACTACTA CTACTACTAC TACTACTACT    2880

ACTACTACTA CTACTACTAC CACAACAACC ACAACCACAA CCACAACTAC CAAGAAACCA    2940

ACAACAACAA CAACAACAAC AACAACAACT ACTACTACAA CCACGACAAC AACAACCACG    3000

ACAACCACAA CCACAACTAC AACTACCAAG AAACCAACAA CTACTACTAC TACTACCACA    3060

ACAACAACAA CTACTACTAC TACCACAACA ACAACAACTA CTACTACTAC TACAACCACA    3120

ACCACAACCA CAACCGCAAC CACAACTACC AAGAAACCAA CAACAACAAC AACAACTACT    3180

ACTACTACTA CAACCAAGAA ACCAACAACA ACTACCACTG CCACAACAAC AACTACTACT    3240

TCTGAAACTG AGAGTGTAAT TAAACCTGAT GAATGGTGTT GGTTGGAAAA GAATGGCGAA    3300

TGTGAGGCAA AAGGAGCAAC TTATGTTGGT GTTATCGGAA AGATGGACG TATTGAAAAT    3360

GGAATGGCAT TTACAATGAT TCCAAATGAT GACACGCATG TCCGTTTCAG ATTTAAGGTT    3420

AAAGATGTAG GAACACTAT TTCAGTAAGA TGCGGAAAAG GTGCAGGTAA ACTCGAGTTC    3480

CCAGATAGAA GTTTGGATTT CACAATTCCT CCAGTAGCTG GCCATAACAG CTGTTCAATA    3540

ATAGTTGGTG TGAGCGGCGG TGGAAAAATT CACGTAAGCC CATACGGTTC TAAGGATGTC    3600

TCTCTAATAA GTGCTCCAAT ACAACCTTGT GAGTTATTCA ATGAAGTTTA TTGCGACACT    3660

TGTACTGCGA AGTATGGTGC AATTCACTCT GGATATCAAA CTTCAGCTGA TTTCGTAACA    3720

ACGACTACCG CAAAACCAAC AACTACTACA ACTGGAGCCC CAGGACAACC AACAACTACT    3780

ACAACTGGAA GTCCAAGCAA ACCAACTACT ACTACCACTA CTAAGGCAAC AACAACCACA    3840

ACAATTCTTA ATCCAATCAT TACAACAACA ACTCAAAAAC CAACAACAAC AACAACAACA    3900

AAGGTTCCAG GTAAGCCACC AATAGCCACA ACAACAACAA CATTAAAGCC AATAGTTACA    3960

ACAACAACAA CAAAAGCAAC AACAACAACA ACAACAACAG TGCCAACGAC AACTACTACT    4020

ACCAAGAGAG ACGAAATGAC AACAACAACG ACACCATTAC CTGATATCGG TGACATTGAA    4080

ATTACACCAA TCCCAATTGA AAAGATGTTG GATAAGTACA CAAGAATGAT TTATGACTAT    4140

AACAGTGGTT TATTATTAGA CTCTAATGAT GAACCAATTC CAGGTTCTCA AGCAGGACAA    4200

ATAGCTGATA CAAGCAATTT ATTCCCAGTT CAAACTCACA AGAGTACTGG TTTACCAATT    4260

GATCCAATGG TTGGTCTTCC ATTTGATCCA AAATCAGGTA ATTTAGTACA TCCATATACC    4320

AATCAAACAA TGTCTGGTTT ATCGGTATCA TATCTTGCTG CTAAGAATTT GACAGTTGAT    4380

ACTGATGAAA CCTACGGTTT ACCAATTGAT ACACTCACTG GTTACCCATT GGATCCAGTC    4440

AGTTTGATTC CGTTCAATCC AGAAACTGGT GAATTGTTTG ATCCAATATC AGATGAGATA    4500

ATGAATGGAA CAATTGCAGG TATTGTTTCA GGAATTTCTG CAAGTGAGTC ATTATTATCT    4560

CAGAAATCAG CTCCAATCGA CCCAGCAACA AATATGGTTG TTGGAGAATT TGGTGGATTG    4620
```

-continued

```
TTGAACCCAG CAACAGGAGT GATGATTCCA GGTTCTTTAG GTCCATCAGA GCAAACTCCA    4680

TTCTCCCCTG AGATTGAAGA TGGTGGTATT ATTCCTCCAG AAGTAGCAGC AGCAAATGCT    4740

GATAAATTCA AGTTATCTAT TCCTCCAAGC GTACCAGAAT CAATTCCAGA AAAGGATCAG    4800

AAGATTGATT CTATTTCTGA ATTGATGTAT GATATTGAGT CAGGTAGACT TATTGGTCAA    4860

GTATCAAAGA GACCAATCCC AGGTTCAATT GCTGGTGACT TGAACCCAAT AATGAAGACA    4920

CCAACACAAA CTGACAGTGT AACTGGTAAA CCAATCGATC CAACCACAGG TCTGCCTTTC    4980

AATCCACCAA CTGGTCATTT GATTAACCCA ACAAATAATA ATACCATGGA TTCTTCATTT    5040

GCTGGTGCAT ACAAATATGC AGTTTCAAAT GGTATTAAGA CTGATAATGT TTATGGTTTA    5100

CCAGTTGATG AAATAACAGG TTTACCAAAG GATCCAGTGT CAGATATTCC ATTTAACTCA    5160

ACTACAGGTG AATTAGTTGA TCCATCAACA GGAAAGCCAA TTAACAATTA TACTGCTGGT    5220

ATTGTTAGTG GAAAACGTGG CTTACCACCT ATTGAAGATG AAAATGGTAA TTTGTTTGAT    5280

CCATCAACTA AATTGCCAAT AGATGGTAAT AACCAATTAG TTAACCCAGA AACCAACAGC    5340

ACTGTTTCAG GATCAACTTC AGGTAGTACA AAACCAAAAC CAGGAATTCC AGTCAATGGT    5400

GGAGGTGTTG TACCTGATGA AGAAGCTAAA GATCAAGCCG ATAAGGGTAA GGATGGATTA    5460

ATTGTTCCAC CAACTAATTC TATCAATAAA GATCCAGTAA CAAATACTCA GTACAGTAAT    5520

ACTACTGGTA ACATTATTAA CCCAGAAACA GGAAAAGTTA TTCCAGGTTC ACTTCCAGGC    5580

TCTCTCAACT ATCCATCATT CAATACTCCA CAACAAACTG ATGAGATTAC AGGAAAGCCA    5640

GTTGATACTG TTACTGGTTT GCCATATGAT CCATCTACAG GTGAAATTAT CGATCCTGCA    5700

ACTAAATTAC CAATTCCAGG ATCAGTTGCA GGTGATGAAA TCCTCACTGA AGTATTGAAC    5760

ATTACAACAG ATGAAGTAAC AGGTTTGCCG ATTGATCTTG AAACTGGTCT TCCAAGAGAT    5820

CCAGTATCAG GACTCCCACA ACTTCCAAAT GGTACCTTGG TTGATCCATC AAATAAAAAA    5880

CCAATTCCAG GTTCACATTC CGGATTTATT AATGGTACAT CTGGAGAACA ATCACATGAG    5940

AAAGATCCAA GTACTGGTAA GCCACTTGAT CCAAATACAG GTTTGCCATT CGATGAAGAT    6000

TCTGGTAGTT TAATTAACCC AGAGACTGGA GATAAACTTC AAGGATCACA TTCTGGTACA    6060

TTTATGCCAG TACCAGGTAA ACCACAAGGT GAAAATGGAG GTATCATGAC ACCTGAGCAG    6120

ATATTGGAAG CATTAAATAA ATTGCCAACA AGTAATGAAG TAAATATTTC ACCAAGACCA    6180

AGTTCAGATG CTGTTCCAGA TAGACCAACA AATACTTGGT GGAATAAGAT TTCTGGTCAA    6240

ACCTTCCAGG TTGATGGAAA GAAGACTATT CCAGGTTCTG CAGCTTCAGT AATTCACACT    6300

GCTCTTGGAA CACCAACTCA AACTGATCCA ACAACAGGAC TTCCATCTGA TCCATCAACA    6360

GGTTTACCAT TCATTCCAGG ATTTAACGTG CTTGTAGATC CTCAGACTGG AGAGCAAATC    6420

AAGGGTTCTG TTCCTTATGT TTCATTGTAC GTTAAGGAAA AGAATATTGT AACAGAAGCT    6480

GCTTATGGTC TACCAGTTGA TCCAAAGACT GGTTTCCCAA TTGATCCAAT TAGTTACCTC    6540

CCGTTTGCTA AGAATGGCGA ACTAATTGAT CCTATCTCTG GTAAATATTT CAGTGGTTCA    6600

ATTGCTGGAT TCATTTCTGG TAAAGCTGGT TCACAATCTA AATCATCTGA TGAATCAGGT    6660

AATCCAATTG ATCCATCAAC AAATATGCCT TACGATCCAA AAACAGGCAA ATTAATTGAT    6720

CCAGAATCTG GCATTGCTAT TGATAATTCT GTTTCAGGTG TGTTTGCAAC TGTACCTGGT    6780

ACTGCTGCAC CGAAAAAGGG TGGTGTCATT CCGGAGTCAG TTGCAGCTGA GGCAGCAAAG    6840

AAATACTTTG CAGCCAATGT TGAGGGAGAG GGAGAAGGAG AAGAAGTTCC ACCACCGCCA    6900

GAATCATCTA GTAACATTGC AATCCAAGCT GCTGGTGGTG CTTCTGCTGC TGTAGGTCTC    6960

GTAGCTGCTG TTGGTGCATG GTATGCAAGC AGAAACAGAC AGGAAGGAGA AGATGATGAT    7020
```

```
AACTATCAGA TGGATTTGAA GCAGAATATG AAGAAGAAGA GGAAGAAGAG GGTGATGAAG      7080

CAGCAAATGA AACTGTTGTT ACAATTGAGC GTGATTCATC ATTCTGGAAC GAATCTTAAA      7140

CGTAGAAAAG ATTTTTCCAA TTCAAAAAAA TTTCGAATAT GAAAATTAAT GATTTCCTAA      7200

TATCAAATAT TACTACATTT CTACATTTCC TATTGAAATA TACGATTTAC TAACATATTG      7260

CTAATTAATA AATGATTAAT AATGACAAAA TTCAACGATA TGATGAATCT ATCAAAGCGT      7320

TTCAAATGGA GAAA                                                       7334

(2) INFORMATION FOR SEQ ID NO:2:

(i) SEQUENCE CHARACTERISTICS:
        (A) LENGTH: 5511 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

GTGAAGTCAA AAATCATGGT GAACATTAAA GTGAGCTCAT CGGCAATAGC CCTTGTGGCT        60

GTTATTATGA ACCCACTTTT TTCACTTGCA TTTAAATCGA GTAACCGATT AGAGATGAGA       120

ATTGAATCAT CTGGTGCAGT TTCAAATGAA AAATTTGTAA TCCCATCTCT CCCTTCAGAT       180

TTAGACCCAA CAACTTTCTT GCTTATTGAT TCTACTGGCA AGAAATTCAG TCCATATACT       240

GGTAAACATG CTGATGCATC AACAACATCT AGTGCTTACA GTGCACCATT TGAGTTGGAT       300

GTTAGCGGAG TTCCAATCGA ACCAAATACA AGAAGAATGG TTGACCCAGT TTCTTTAATG       360

CTTTTTGATA ATAGCACTGG CGTAATGTAC GATCCAAACA CGAATTCTAT TTTGGAAGGT       420

TCAATTGCAG GTATTAGAAG CGAATCTTGC ATTGTATCTG AACTGAACTT TACATCTACT       480

ACTGGATTTA CAACGGACAC ATCAATGAAT TGGCCGGTAA GTATCACAAG TGGTGAACTG       540

AAGGATCCAA ACAAACAAGC TACTATTTCT GGTTCAAGAT CTTGTGGATG GAAACAAGGT       600

TATAGCATTG ATTCATCCAC CGGGTTTAGA GTTGATTCTA TCACTGGTCT CCCAACTGAT       660

CCATACCCTA ATTGTCCATT CAACCCTGTC ACTGGAAATT TAGTCAGTAG GTCCACTGGT       720

AAAACTATTC CAAACACTTA TGCAGGTGTT TATCGTTCTA ATGAGACTAA GACCACTGAG       780

CCTAGTGCAA ACACCAACTT CTTGTTGGTA GATCCTAAGA TTAATGCTCC TTGTAATTCT       840

GAGAACTCTT TGAACAAGT CCAAATATTT GATATGGGCA GTAAGGTATA CATTCCATAC       900

ACTAAATGTG TTGGAGTGAA ACACACAACA ACAACAACAA CAACTACTAC TACTACTACT       960

ACGACAACAA CAACAACAAC GACAACAACA ACAACTACTA CAACTACTAC CACTACTACT      1020

ACGACAACAA CAACTACTAC TACGACAACA ACAACAACAA CTACTACTAC TACTACAACC      1080

ACAACAACTA CAACCACGAC AACTACAACC ACAACCACAA CTACCAAGAA ACCAACAACA      1140

ACAACAACAA CAACAACTAC TACTACACA ACAACAACAA CAACAACTAC TACTACTACT       1200

ACTACTACTA CTACTACTAC TACTACTACT ACCACAACAA CCACAACCAC AACCACAACT      1260

ACCAAGAAAC CAACAACAAC AACAACAACA ACAACAACAA CTACTACTAC AACCACGACA      1320

ACAACAACCA CGACACCAC AACCACAACT ACAACTACCA AGAAACCAAC AACTACTACT       1380

ACTACTACCA CAACAACAAC AACTACTACT ACTACCACAA CAACAACAAC TACTACTACT      1440

ACTACAACCA CAACCACAAC CACAACCGCA ACCACAACTA CCAAGAAACC AACAACAACA      1500

ACAACAACTA CTACTACTAC TACAACCAAG AAACCAACAA CAACTACCAC TGCCACAACA      1560

ACAACTACTA CTTCTGAAAC TGAGAGTGTA ATTAAACCTG ATGAATGGTG TTGGTTGGAA      1620
```

-continued

```
AAGAATGGCG AATGTGAGGC AAAAGGAGCA ACTTATGTTG GTGTTATCGG AAAAGATGGA    1680

CGTATTGAAA ATGGAATGGC ATTTACAATG ATTCCAAATG ATGACACGCA TGTCCGTTTC    1740

AGATTTAAGG TTAAAGATGT AGGGAACACT ATTTCAGTAA GATGCGGAAA AGGTGCAGGT    1800

AAACTCGAGT TCCCAGATAG AAGTTTGGAT TTCACAATTC CTCCAGTAGC TGGCCATAAC    1860

AGCTGTTCAA TAATAGTTGG TGTGAGCGGC GGTGGAAAAA TTCACGTAAG CCCATACGGT    1920

TCTAAGGATG TCTCTCTAAT AAGTGCTCCA ATACAACCTT GTGAGTTATT CAATGAAGTT    1980

TATTGCGACA CTTGTACTGC GAAGTATGGT GCAATTCACT CTGGATATCA AACTTCAGCT    2040

GATTTCGTAA CAACGACTAC CGCAAAACCA ACAACTACTA CAACTGGAGC CCCAGGACAA    2100

CCAACAACTA CTACAACTGG AAGTCCAAGC AAACCAACTA CTACTACCAC TACTAAGGCA    2160

ACAACAACCA CAACAATTCT TAATCCAATC ATTACAACAA CAACTCAAAA ACCAACAACA    2220

ACAACAACAA CAAAGGTTCC AGGTAAGCCA CCAATAGCCA CAACAACAAC AACATTAAAG    2280

CCAATAGTTA CAACAACAAC AACAAAAGCA ACAACAACAA CAACAACAAC AGTGCCAACG    2340

ACAACTACTA CTACCAAGAG AGACGAAATG ACAACAACAA CGACACCATT ACCTGATATC    2400

GGTGACATTG AAATTACACC AATCCCAATT GAAAAGATGT TGGATAAGTA CACAAGAATG    2460

ATTTATGACT ATAACAGTGG TTTATTATTA GACTCTAATG ATGAACCAAT TCCAGGTTCT    2520

CAAGCAGGAC AAATAGCTGA TACAAGCAAT TTATTCCCAG TTCAAACTCA CAAGAGTACT    2580

GGTTTACCAA TTGATCCAAT GGTTGGTCTT CCATTTGATC CAAAATCAGG TAATTTAGTA    2640

CATCCATATA CCAATCAAAC AATGTCTGGT TTATCGGTAT CATATCTTGC TGCTAAGAAT    2700

TTGACAGTTG ATACTGATGA AACCTACGGT TTACCAATTG ATACACTCAC TGGTTACCCA    2760

TTGGATCCAG TCAGTTTGAT TCCGTTCAAT CCAGAAACTG GTGAATTGTT TGATCCAATA    2820

TCAGATGAGA TAATGAATGG AACAATTGCA GGTATTGTTT CAGGAATTTC TGCAAGTGAG    2880

TCATTATTAT CTCAGAAATC AGCTCCAATC GACCCAGCAA CAAATATGGT TGTTGGAGAA    2940

TTTGGTGGAT TGTTGAACCC AGCAACAGGA GTGATGATTC CAGGTTCTTT AGGTCCATCA    3000

GAGCAAACTC CATTCTCCCC TGAGATTGAA GATGGTGGTA TTATTCCTCC AGAAGTAGCA    3060

GCAGCAAATG CTGATAAATT CAAGTTATCT ATTCCTCCAA GCGTACCAGA ATCAATTCCA    3120

GAAAAGGATC AGAAGATTGA TTCTATTTCT GAATTGATGT ATGATATTGA GTCAGGTAGA    3180

CTTATTGGTC AAGTATCAAA GAGACCAATC CCAGGTTCAA TTGCTGGTGA CTTGAACCCA    3240

ATAATGAAGA CACCAACACA AACTGACAGT GTAACTGGTA AACCAATCGA TCCAACCACA    3300

GGTCTGCCTT TCAATCCACC AACTGGTCAT TTGATTAACC CAACAAATAA TAATACCATG    3360

GATTCTTCAT TTGCTGGTGC ATACAAATAT GCAGTTTCAA ATGGTATTAA GACTGATAAT    3420

GTTTATGGTT TACCAGTTGA TGAAATAACA GGTTTACCAA AGGATCCAGT GTCAGATATT    3480

CCATTTAACT CAACTACAGG TGAATTAGTT GATCCATCAA CAGGAAAGCC AATTAACAAT    3540

TATACTGCTG GTATTGTTAG TGGAAAACGT GGCTTACCAC CTATTGAAGA TGAAAATGGT    3600

AATTTGTTTG ATCCATCAAC TAAATTGCCA ATAGATGGTA ATAACCAATT AGTTAACCCA    3660

GAAACCAACA GCACTGTTTC AGGATCAACT TCAGGTAGTA CAAAACCAAA ACCAGGAATT    3720

CCAGTCAATG GTGGAGGTGT TGTACCTGAT GAAGAAGCTA AGATCAAGC CGATAAGGGT    3780

AAGGATGGAT TAATTGTTCC ACCAACTAAT TCTATCAATA AAGATCCAGT AACAAATACT    3840

CAGTACAGTA ATACTACTGG TAACATTATT AACCCAGAAA CAGGAAAAGT TATTCCAGGT    3900

TCACTTCCAG GCTCTCTCAA CTATCCATCA TTCAATACTC CACAACAAAC TGATGAGATT    3960
```

```
ACAGGAAAGC CAGTTGATAC TGTTACTGGT TTGCCATATG ATCCATCTAC AGGTGAAATT    4020

ATCGATCCTG CAACTAAATT ACCAATTCCA GGATCAGTTG CAGGTGATGA AATCCTCACT    4080

GAAGTATTGA ACATTACAAC AGATGAAGTA ACAGGTTTGC CGATTGATCT TGAAACTGGT    4140

CTTCCAAGAG ATCCAGTATC AGGACTCCCA CAACTTCCAA ATGGTACCTT GGTTGATCCA    4200

TCAAATAAAA AACCAATTCC AGGTTCACAT TCCGGATTTA TTAATGGTAC ATCTGGAGAA    4260

CAATCACATG AGAAAGATCC AAGTACTGGT AAGCCACTTG ATCCAAATAC AGGTTTGCCA    4320

TTCGATGAAG ATTCTGGTAG TTTAATTAAC CCAGAGACTG GAGATAAACT TCAAGGATCA    4380

CATTCTGGTA CATTTATGCC AGTACCAGGT AAACCACAAG GTGAAAATGG AGGTATCATG    4440

ACACCTGAGC AGATATTGGA AGCATTAAAT AAATTGCCAA CAAGTAATGA AGTAAATATT    4500

TCACCAAGAC CAAGTTCAGA TGCTGTTCCA GATAGACCAA CAAATACTTG GTGGAATAAG    4560

ATTTCTGGTC AAACCTTCCA GGTTGATGGA AAGAAGACTA TTCCAGGTTC TGCAGCTTCA    4620

GTAATTCACA CTGCTCTTGG AACACCAACT CAAACTGATC CAACAACAGG ACTTCCATCT    4680

GATCCATCAA CAGGTTTACC ATTCATTCCA GGATTTAACG TGCTTGTAGA TCCTCAGACT    4740

GGAGAGCAAA TCAAGGGTTC TGTTCCTTAT GTTTCATTGT ACGTTAAGGA AAAGAATATT    4800

GTAACAGAAG CTGCTTATGG TCTACCAGTT GATCCAAAGA CTGGTTTCCC AATTGATCCA    4860

ATTAGTTACC TCCCGTTTGC TAAGAATGGC GAACTAATTG ATCCTATCTC TGGTAAATAT    4920

TTCAGTGGTT CAATTGCTGG ATTCATTTCT GGTAAAGCTG GTTCACAATC TAAATCATCT    4980

GATGAATCAG GTAATCCAAT TGATCCATCA ACAAATATGC CTTACGATCC AAAAACAGGC    5040

AAATTAATTG ATCCAGAATC TGGCATTGCT ATTGATAATT CTGTTTCAGG TGTGTTTGCA    5100

ACTGTACCTG GTACTGCTGC ACCGAAAAAG GGTGGTGTCA TTCCGGAGTC AGTTGCAGCT    5160

GAGGCAGCAA AGAAATACTT TGCAGCCAAT GTTGAGGGAG AGGGAGAAGG AGAAGAAGTT    5220

CCACCACCGC CAGAATCATC TAGTAACATT GCAATCCAAG CTGCTGGTGG TGCTTCTGCT    5280

GCTGTAGGTC TCGTAGCTGC TGTTGGTGCA TGGTATGCAA GCAGAAACAG ACAGGAAGGA    5340

GAAGATGATG ATGACTATCA GATGGATTTG AAGCAGAATA TGAAGAAGAA GAGGAAGAAG    5400

AGGGTGATGA AGCAGCAAAT GAAACTGTTG TTACAATTGA GCGTGATTCA TCATTCTGGA    5460

ACGAATCTTA AACGTAGAAA AGATTTTTCC AATTCAAAAA AATTTCGAAT A            5511
```

(2) INFORMATION FOR SEQ ID NO:3:

(i) SEQUENCE CHARACTERISTICS:
        (A) LENGTH: 5318 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

```
ATTTTGGAAG GTTCAATTGC AGGTATTAGA AGCGAATCTT GCATTGTATC TGAACTGAAC      60

TTTACATCTA CTACTGGATT TACAACGGAC ACATCAATGA ATTGGCCGGT AAGTATCACA     120

AGTGGTGAAC TGAAGGATCC AAACAAACAA GCTACTATTT CTGGTTCAAG ATCTTGTGGA     180

TGGAAACAAG GTTATAGCAT TGATTCATCC ACCGGGTTTA GAGTTGATTC TATCACTGGT     240

CTCCCAACTG ATCCATACTC TAATTGTCCA TTCAACCCTG TCACTGGAAA TTTAGTCAGT     300

AGGTCCACTG GTAAAACTAT TCCAAACACT TATGCAGGTG TTTATCGTTC TAATGAGACT     360

AAGACCACTG AGCCTAGTGC AAACACTTAT GCAGGTGTTT ATCGTTCTAA TGAGACTAAG     420
```

-continued

```
ACCACTGAGC CTAGTGCAAA CACCAACTTC TTGTTGGTAG ATCCTAAGAT TAATGCTCCT      480

TGTAATTCTG AGAACTCTTT TGAACAAGGT CAAATATTTG ATATGGGCAG TAAGGTATAC      540

ATTCCATACA CTAAATGTGT TGGAGTGAAA CACACAACAA CAACAACAAC AACTACTACT      600

ACTACTACTA CGACAACAAC AACAACAACG ACAACAACAA CAACTACTAC AACTACTACC      660

ACTACTACTA CGACAACAAC AACAACAACA ACAACAACAA CAACAACAAC AACAACAACA      720

ACAACAACAA CAACGACTAC TACTACTACT ACTACTACTA CTACTACTAC TACTACTACA      780

ACCACAACAA CTACAACCAC AACTACAACC ACAACAACTA CAACCACAAC AACAACAACC      840

ACAACAACTA CAACCACAAC TACAACCACA ACAACTACAA CCACAACAAC CACAACCACA      900

ACCACAACTA CCAAGAAACC AACAACAACA ACTACAACAA CAACAACAAC AACAACAACT      960

ACTACTACAA CCACCACAAC AACAACAACA ACAACAACTA CAACTACCAA GAAACCAACA     1020

ACTACTACTA CTACTACCAC AACAACAACA ACTACTACTA CTACCACAAC AACAACAACT     1080

ACTACTACTA CTACAACAAC AACAACAACA ACAACAACAA CAACAACTAC CACGAAACCA     1140

ACAACAACAA CAACAACTAC TACTACTACT ACAACCAAGA AACCAACAAC AACTACCACT     1200

GCCACAACAA CAACTACTAC TTCTGAAACT GAGAGTGTAA TTAAACCTGA TGAATGGTGT     1260

TGGTTGGAAA AGAATGGCGA ATGTGAGGCA AAAGGAGCAA CTTATGTTGG TGTTATCGGA     1320

AAAGATGGAC GTATTGAAAA TGGAATGGCA TTTACAATGA TTCCAAATGA TGACACGCAT     1380

GTCCGCTTCA GATTTAAGGT TAAAGATGTA GGGAACACTA TTTCAGTAAG ATGCAGAAAA     1440

GGTGCAGGTA AACTCGAGTT CCCAGATAGA AGTTTGGATT TCACAATTCC TCCAGTAGCT     1500

GGCCATAACA GCTGTTCAAT AATAGTTGGT GTGAGCGGCG ATGGAAAAAT TCACGTAAGC     1560

CCATACGGTT CTAAGGATGT CTCTCTAATA AGTGCTCCAA TACAACCTTC TGAGTTATTC     1620

AATGAAGTTT ATTGCGACAC TTGTACTGCG AAGTATGGTG CAATTCACTC TGGATATCAA     1680

ACTTCAGCTG ATTTCGTAAC AACGACTACC GCAAAACCAA CAACTACTAC AACTGGAGCC     1740

CCAGGACAAC CAACAACTAC TACAACTGGA AGTCCAAGCA AACCAACTAC TACTACCACT     1800

ACTAAGGCAA CAACAACCAC AACAACTCTT AATCCAATCA TTACAACAAC AACTCAAAAA     1860

CCAACAACAA CAACAACAAC AAAGGTTCCA GGTAAGCCAC CAATAGCCAC AACAACAACA     1920

ACATTAAAGC CAATAGTTAC AACAACAACA ACAAAGCAAC AACAACAAC AACAACAACA      1980

GTGCCAACGA CAACTACTAC TACCAAGAGA GACGAAATGA CAACAACAAC GACACCATTA     2040

CCTGATATCG GTGACATTGA AATTACACCA ATCCCAATTG AAAAGATGTT GGATAAGTAC     2100

ACAAGAATGA TTTATGACTA TAACAGTGGT TTATTATTAG ACTCTAATGA TGAACCAATT     2160

CCAGGTTCTC AAGCAGGACA AATAGCTGAT ACAAGCAATT TATTCCCAGT TCAAACTCAC     2220

AAGAGTACTG GTTACCAAT TGATCCAATG GTTGGTCTTC CATTTGATCC AAAATCAGGT     2280

AATTTAGTAC ATCCATATAC CAATCAAACA ATGTCTGGTT TATCGGTATC ATATCTTGCT     2340

GCTAAGAATT TGACAGTTGA TACTGATGAA ACCTACGGTT TACCAATTGA TACACTCACT     2400

GGTTACCCAT TGGATCCAGT CAGTTTGATT CCGTTCAATC CAGAAACTGG TGAATTGTTT     2460

GATCCAATAT CAGATGAGAT AATGAATGGA ACAATTGCAG GTATTGTTTC AGGAATTTCT     2520

GCAAGTGAGT CATTATTATC TCAGAAATCA GCTCTAATCG ACCCAGCAAC AAATATGGTT     2580

GTTGGAGAAT TTGGTGGATT GTTGAACCCA GCAACAGGAG TGATGATTCC AGGTTTTTTA     2640

GGTCCATCAG AGCAAACTCA ATTCTCCCCT GAGATTGAAG ATGGTGGTAT TATTCCTCCA     2700

GAAGTAGCAG CAGCAAATGC TGATAAATTC AAGTTATCTA TTCCTCCAAG CGTACCAGAA     2760

TCAATTCCAG AAAAGGATCA GAAGATTGAT TCTATTTCTG AATTGATGTA TGATATTGAG     2820
```

```
TCAGGTAGAC TTATTGGTCA AGTATCAAAG AGACCAATCC CAGGTTCAAT TGCTGGTGAC    2880

TTGAACCCAA TAATGAAGAC ACCAACACAA ACTGACAGTG TAACTGGTAA ACCAATCGAT    2940

CCAACCACAG GTCTGCCTTT CAATCCACCA ACTGGTCATT TGATTAACCC AACAAATAAT    3000

AATACCATGG ATTCTTCATT TGCTGGTGCA TACAAATATG CAGTTTCAAA TGGTATTAAG    3060

ACTGATAATG TTTATGGTTT ACCAGTTGGT GAAATAACAG GTTTACCAAA GGATCCAGGC    3120

TCAGATATTC CATTTAACTC AACTACAGGT GAATTAGTTG ATCCATCAAC AGGAAAGCCA    3180

ATTAACAATT CTACTGCTGG TATTGTTAGT GGAAAACCTG GCTTACCACC TATTGAAGAT    3240

GAAAATGGTA ATTTGTTTGA TCCATCAACT AACTTGCCAA TAGATGGTAA TAACCAATTA    3300

GTTAACCCAG AAACCAACAG CACTGTCTCA GGATCAACTT CAGGTACTAC AAAACCAAAA    3360

CCAGGAATTC CAGTCAATGG TGGAGGTGTT GTACCTGATG AAGAAGCTAA AGATCAAGCC    3420

GATAAGGGTA AGGATGGATT AATTGTTCCA CCAACTAATT CTATCAATAA AGATCCAGTA    3480

ACAAATACTC AGTACAGTAA TACTACTGGT AACATTATTA ACCCAGAAAC AGGAAAAGTT    3540

ATTCCAGGTT CACTTCCAGG CTCTCTCAAC TATCCATCAT TCAATACTCC ACAACAAACT    3600

GATGAGATTA CAGGAAAGCC AGTTGATACT GTTACTGGTT TGCCATATGA TCCATCTACA    3660

GGTGAAATTA TCGATCCTGC AACTAAATTA CCAATTCCAG GATCAGTTGC AGGTGATGAA    3720

ATCCTCACTG AAGTATTGAA CATTACAACA GATGAAGTAA CAGGTTTGCC AATTGATCTT    3780

GAAACTGGTC TTCCAAGAGA TCCAGTATCA GGACTCCCAC AACTTCCAAA TGGTACCTTG    3840

GTTGATCCAT CAAATAAAAA ACCAATTCCA GGTTCACATT CCGGATTTAT TAATGGTACA    3900

TCTGGAGAAC AATCACATGA GAAAGATCCA AGTACTGGTA AGCCACTTGA TCCAAATACA    3960

GGTTTGCACC CATTCGATGA AGATTCAGGT AGTTTAATTA ACCCAGAGAC TGGAGATAAA    4020

CTTCAAGGAT CACATTCTGG TACATTTATG CCAGTACCAG GTAAACCACA AGGTGAAAAT    4080

GGAGGTATCA TGACACCTGA GCAGATATTG GAAGCATTAA ATAAATTGCC AACAAGTAAT    4140

GAAGTAAATA TTTCACCAAG ACCAAGTTCA GATGCTGTTC CAGATAGACC AACAAATACT    4200

TGGTGGAATA AGATTTCTGG TCAAACCTAC CAGGTTGATG GAAAGAAGAC TATTCCAGGT    4260

TCTGCAGCTT CAGTAATTCA CACTGCTCTT GGAACACCAA CTCAAACTGA TCCAACAACA    4320

GGACTTCCAT CTGATCCATC AACAGGTTTA CCATTCATTC CAGGATTTAA CGTGCTTGTA    4380

GATCCTCAGA CTGGAGAGCA AATCAAGGGT TCTGTTCCTT ATGTTTCATT GTACGTTAAG    4440

GAAAAGAATA TTGTAACAGA AGCTGCTTAT GGTCTACCAG TTGATCCAAA GACTGGTTTC    4500

CCAATTGATC CAATTAGTTA CCTCCCGTTT GCTAAGAATG GCGAACTAAT TGATCCTATC    4560

TCTGGTAAAT ATTTCAGTGG TTCAATTGCT GGATTCATTT CTGGTAAAGC TGGTTCACAA    4620

TCTAAATCAT CTGATGAATC AGGTAATCCA ATTGATCCAT CAACAAATAT GCCTTACGAT    4680

CCAAAAGGCG GCAAATTAAT TGATCCAGAA TCTGGCATTG CTATTGATAA TTCTGTTTCA    4740

GGTGTGTTTG CAACTGTACC TGGTACTGCT GCACCGAAAA AGGGTGGTGT CATTCCGGAG    4800

TCAGTTGCAG CTGAGGCAGC AAAGAAATAC TTTCAGCCA ATGTTGAGGG AGAGGGAGAA    4860

GGAGAAGAAG TTCCACCACC GCCAGAATCA TCTAGTAACA TTGCAATCCA AGCTGCTGGT    4920

GGTGCTTCTG CTGCTGTAGG TCTCGTAGCT GCTGTTGGTG CATGGTATGC AAGCAGAAAC    4980

AGACAGGAAG GAGAAGATGA TGATGACTAT CAGATGGATT TGAAGCAGAA TATGAAGAAG    5040

AAGAGGAAGA AGAGGGTGAT GAAGCAGCAA ATGAAACTGT TGTTACAATT GAGCGTGATT    5100

CATCATTCTG GAACGAATCT TAAACGTAGA AAAGATTTTT CCAATTCAAA AAAATTTCGA    5160
```

```
ATATGAAAAT TAATGATTTC CTAATATCAA ATATTACTAC ATTTCTACAT TTCCTATTGA       5220

AATATACGAT TTACTAACAT ATTGCTAATT AATAAATGAT TAATAATGAC AAAATTCAAC       5280

GATATGATGA ATCTATCAAA GCGTTTCAAA TGGAGAAA                                5318

(2) INFORMATION FOR SEQ ID NO:4:

(i) SEQUENCE CHARACTERISTICS:
        (A) LENGTH: 5163 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

ATTTTGGAAG GTTCAATTGC AGGTATTAGA AGCGAATCTT GCATTGTATC TGAACTGAAC         60

TTTACATCTA CTACTGGATT TACAACGGAC ACATCAATGA ATTGGCCGGT AAGTATCACA        120

AGTGGTGAAC TGAAGGATCC AAACAAACAA GCTACTATTT CTGGTTCAAG ATCTTGTGGA        180

TGGAAACAAG GTTATAGCAT TGATTCATCC ACCGGGTTTA GAGTTGATTC TATCACTGGT        240

CTCCCAACTG ATCCATACTC TAATTGTCCA TTCAACCCTG TCACTGGAAA TTTAGTCAGT        300

AGGTCCACTG GTAAAACTAT TCCAAACACT TATGCAGGTG TTTATCGTTC TAATGAGACT        360

AAGACCACTG AGCCTAGTGC AAACACTTAT GCAGGTGTTT ATCGTTCTAA TGAGACTAAG        420

ACCACTGAGC CTAGTGCAAA CACCAACTTC TTGTTGGTAG ATCCTAAGAT TAATGCTCCT        480

TGTAATTCTG AGAACTCTTT TGAACAAGGT CAAATATTTG ATATGGGCAG TAAGGTATAC        540

ATTCCATACA CTAAATGTGT TGGAGTGAAA CACACAACAA CAACAACAAC AACTACTACT        600

ACTACTACTA CGACAACAAC AACAACAACG ACAACAACAA CAACTACTAC AACTACTACC        660

ACTACTACTA CGACAACAAC AACAACAACA ACAACAACAA CAACAACAAC AACAACAACA        720

ACAACAACAA CAACGACTAC TACTACTACT ACTACTACTA CTACTACTAC TACTACTACA        780

ACCACAACAA CTACAACCAC AACTACAACC ACAACAACTA CAACCACAAC AACAACAACC        840

ACAACAACTA CAACCACAAC TACAACCACA CAACTACAAC CACAACAACC ACAACCACA         900

ACCACAACTA CCAAGAAACC AACAACAACA ACTACAACAA CAACAACAAC AACAACAACT        960

ACTACTACAA CCACCACAAC AACAACAACA ACAACAACTA CAACTACCAA GAAACCAACA       1020

ACTACTACTA CTACTACCAC AACAACAACA ACTACTACTA CTACCACAAC AACAACAACT       1080

ACTACTACTA CTACAACAAC AACAACAACA ACAACAACAA CAACAACTAC CACGAAACCA       1140

ACAACAACAA CAACAACTAC TACTACTACT ACAACCAAGA AACCAACAAC AACTACCACT       1200

GCCACAACAA CAACTACTAC TTCTGAAACT GAGAGTGTAA TTAAACCTGA TGAATGGTGT       1260

TGGTTGGAAA AGAATGGCGA ATGTGAGGCA AAAGGAGCAA CTTATGTTGG TGTTATCGGA       1320

AAAGATGGAC GTATTGAAAA TGGAATGGCA TTTACAATGA TTCCAAATGA TGACACGCAT       1380

GTCCGCTTCA GATTTAAGGT TAAAGATGTA GGGAACACTA TTTCAGTAAG ATGCAGAAAA       1440

GGTGCAGGTA AACTCGAGTT CCCAGATAGA AGTTTGGATT TCACAATTCC TCCAGTAGCT       1500

GGCCATAACA GCTGTTCAAT AATAGTTGGT GTGAGCGGCG ATGGAAAAAT TCACGTAAGC       1560

CCATACGGTT CTAAGGATGT CTCTCTAATA AGTGCTCCAA TACAACCTTC TGAGTTATTC       1620

AATGAAGTTT ATTGCGACAC TTGTACTGCG AAGTATGGTG CAATTCACTC TGGATATCAA       1680

ACTTCAGCTG ATTTCGTAAC AACGACTACC GCAAAACCAA CAACTACTAC AACTGGAGCC       1740

CCAGGACAAC CAACAACTAC TACAACTGGA AGTCCAAGCA AACCAACTAC TACTACCACT       1800
```

```
ACTAAGGCAA CAACAACCAC AACAACTCTT AATCCAATCA TTACAACAAC AACTCAAAAA    1860

CCAACAACAA CAACAACAAC AAAGGTTCCA GGTAAGCCAC CAATAGCCAC AACAACAACA    1920

ACATTAAAGC CAATAGTTAC AACAACAACA ACAAAAGCAA CAACAACAAC AACAACAACA    1980

GTGCCAACGA CAACTACTAC TACCAAGAGA GACGAAATGA CAACAACAAC GACACCATTA    2040

CCTGATATCG GTGACATTGA AATTACACCA ATCCCAATTG AAAAGATGTT GGATAAGTAC    2100

ACAAGAATGA TTTATGACTA TAACAGTGGT TTATTATTAG ACTCTAATGA TGAACCAATT    2160

CCAGGTTCTC AAGCAGGACA AATAGCTGAT ACAAGCAATT TATTCCCAGT TCAAACTCAC    2220

AAGAGTACTG GTTTACCAAT TGATCCAATG GTTGGTCTTC CATTTGATCC AAAATCAGGT    2280

AATTTAGTAC ATCCATATAC CAATCAAACA ATGTCTGGTT TATCGGTATC ATATCTTGCT    2340

GCTAAGAATT TGACAGTTGA TACTGATGAA ACCTACGGTT TACCAATTGA TACACTCACT    2400

GGTTACCCAT TGGATCCAGT CAGTTTGATT CCGTTCAATC CAGAAACTGG TGAATTGTTT    2460

GATCCAATAT CAGATGAGAT AATGAATGGA ACAATTGCAG GTATTGTTTC AGGAATTTCT    2520

GCAAGTGAGT CATTATTATC TCAGAAATCA GCTCTAATCG ACCCAGCAAC AAATATGGTT    2580

GTTGGAGAAT TTGGTGGATT GTTGAACCCA GCAACAGGAG TGATGATTCC AGGTTTTTTA    2640

GGTCCATCAG AGCAAAACTCA ATTCTCCCCT GAGATTGAAG ATGGTGGTAT TATTCCTCCA    2700

GAAGTAGCAG CAGCAAATGC TGATAAATTC AAGTTATCTA TTCCTCCAAG CGTACCAGAA    2760

TCAATTCCAG AAAAGGATCA GAAGATTGAT TCTATTTCTG AATTGATGTA TGATATTGAG    2820

TCAGGTAGAC TTATTGGTCA AGTATCAAAG AGACCAATCC CAGGTTCAAT TGCTGGTGAC    2880

TTGAACCCAA TAATGAAGAC ACCAACACAA ACTGACAGTG TAACTGGTAA ACCAATCGAT    2940

CCAACCACAG GTCTGCCTTT CAATCCACCA ACTGGTCATT TGATTAACCC AACAAATAAT    3000

AATACCATGG ATTCTTCATT TGCTGGTGCA TACAAATATG CAGTTTCAAA TGGTATTAAG    3060

ACTGATAATG TTTATGGTTT ACCAGTTGGT GAAATAACAG GTTTACCAAA GGATCCAGGC    3120

TCAGATATTC CATTTAACTC AACTACAGGT GAATTAGTTG ATCCATCAAC AGGAAAGCCA    3180

ATTAACAATT CTACTGCTGG TATTGTTAGT GGAAAACCTG GCTTACCACC TATTGAAGAT    3240

GAAAATGGTA ATTTGTTTGA TCCATCAACT AACTTGCCAA TAGATGGTAA TAACCAATTA    3300

GTTAACCCAG AAACCAACAG CACTGTCTCA GGATCAACTT CAGGTACTAC AAAACCAAAA    3360

CCAGGAATTC CAGTCAATGG TGGAGGTGTT GTACCTGATG AAGAAGCTAA AGATCAAGCC    3420

GATAAGGGTA AGGATGGATT AATTGTTCCA CCAACTAATT CTATCAATAA AGATCCAGTA    3480

ACAAATACTC AGTACAGTAA TACTACTGGT AACATTATTA ACCCAGAAAC AGGAAAAGTT    3540

ATTCCAGGTT CACTTCCAGG CTCTCTCAAC TATCCATCAT TCAATACTCC ACAACAAACT    3600

GATGAGATTA CAGGAAAGCC AGTTGATACT GTTACTGGTT TGCCATATGA TCCATCTACA    3660

GGTGAAATTA TCGATCCTGC AACTAAATTA CCAATTCCAG GATCAGTTGC AGGTGATGAA    3720

ATCCTCACTG AAGTATTGAA CATTACAACA GATGAAGTAA CAGGTTTGCC AATTGATCTT    3780

GAAACTGGTC TTCCAAGAGA TCCAGTATCA GGACTCCCAC AACTTCCAAA TGGTACCTTG    3840

GTTGATCCAT CAAATAAAAA ACCAATTCCA GGTTCACATT CCGGATTTAT TAATGGTACA    3900

TCTGGAGAAC AATCACATGA GAAAGATCCA AGTACTGGTA AGCCACTTGA TCCAAATACA    3960

GGTTTGCACC CATTCGATGA AGATTCAGGT AGTTTAATTA ACCCAGAGAC TGGAGATAAA    4020

CTTCAAGGAT CACATTCTGG TACATTTATG CCAGTACCAG GTAAACCACA AGGTGAAAAT    4080

GGAGGTATCA TGACACCTGA GCAGATATTG GAAGCATTAA ATAAATTGCC AACAAGTAAT    4140

GAAGTAAATA TTTCACCAAG ACCAAGTTCA GATGCTGTTC CAGATAGACC AACAAATACT    4200
```

-continued

```
TGGTGGAATA AGATTTCTGG TCAAACCTAC CAGGTTGATG GAAAGAAGAC TATTCCAGGT    4260

TCTGCAGCTT CAGTAATTCA CACTGCTCTT GGAACACCAA CTCAAACTGA TCCAACAACA    4320

GGACTTCCAT CTGATCCATC AACAGGTTTA CCATTCATTC CAGGATTTAA CGTGCTTGTA    4380

GATCCTCAGA CTGGAGAGCA AATCAAGGGT TCTGTTCCTT ATGTTTCATT GTACGTTAAG    4440

GAAAAGAATA TTGTAACAGA AGCTGCTTAT GGTCTACCAG TTGATCCAAA GACTGGTTTC    4500

CCAATTGATC CAATTAGTTA CCTCCCGTTT GCTAAGAATG GCGAACTAAT TGATCCTATC    4560

TCTGGTAAAT ATTTCAGTGG TTCAATTGCT GGATTCATTT CTGGTAAAGC TGGTTCACAA    4620

TCTAAATCAT CTGATGAATC AGGTAATCCA ATTGATCCAT CAACAAATAT GCCTTACGAT    4680

CCAAAAGGCG GCAAATTAAT TGATCCAGAA TCTGGCATTG CTATTGATAA TTCTGTTTCA    4740

GGTGTGTTTG CAACTGTACC TGGTACTGCT GCACCGAAAA AGGGTGGTGT CATTCCGGAG    4800

TCAGTTGCAG CTGAGGCAGC AAAGAAATAC TTTGCAGCCA ATGTTGAGGG AGAGGGAGAA    4860

GGAGAAGAAG TTCCACCACC GCCAGAATCA TCTAGTAACA TTGCAATCCA AGCTGCTGGT    4920

GGTGCTTCTG CTGCTGTAGG TCTCGTAGCT GCTGTTGGTG CATGGTATGC AAGCAGAAAC    4980

AGACAGGAAG GAGAAGATGA TGATGACTAT CAGATGGATT TGAAGCAGAA TATGAAGAAG    5040

AAGAGGAAGA AGAGGGTGAT GAAGCAGCAA ATGAAACTGT TGTTACAATT GAGCGTGATT    5100

CATCATTCTG GAACGAATCT TAAACGTAGA AAAGATTTTT CCAATTCAAA AAAATTTCGA    5160

ATA                                                                  5163
```

(2) INFORMATION FOR SEQ ID NO:5:

(i) SEQUENCE CHARACTERISTICS:
        (A) LENGTH: 1837 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

```
Val Lys Ser Lys Ile Met Val Asn Ile Lys Val Ser Ser Ala Ile
1               5                   10                  15

Ala Leu Val Ala Val Ile Met Asn Pro Leu Phe Ser Leu Ala Phe Lys
            20                  25                  30

Ser Ser Asn Arg Leu Glu Met Arg Ile Glu Ser Ser Gly Ala Val Ser
        35                  40                  45

Asn Glu Lys Phe Val Ile Pro Ser Leu Pro Ser Asp Leu Asp Pro Thr
    50                  55                  60

Thr Phe Leu Leu Ile Asp Ser Thr Gly Lys Lys Phe Ser Pro Tyr Thr
65                  70                  75                  80

Gly Lys His Ala Asp Ala Ser Thr Thr Ser Ser Ala Tyr Ser Ala Pro
                85                  90                  95

Phe Glu Leu Asp Val Ser Gly Val Pro Ile Glu Pro Asn Thr Arg Arg
            100                 105                 110

Met Val Asp Pro Val Ser Leu Met Leu Phe Asp Asn Ser Thr Gly Val
        115                 120                 125

Met Tyr Asp Pro Asn Thr Asn Ser Ile Leu Glu Gly Ser Ile Ala Gly
    130                 135                 140

Ile Arg Ser Glu Ser Cys Ile Val Ser Glu Leu Asn Phe Thr Ser Thr
145                 150                 155                 160

Thr Gly Phe Thr Thr Asp Thr Ser Met Asn Trp Pro Val Ser Ile Thr
```

-continued

```
                165                 170                 175
Ser Gly Glu Leu Lys Asp Pro Asn Lys Gln Ala Thr Ile Ser Gly Ser
                180                 185                 190

Arg Ser Cys Gly Trp Lys Gln Gly Tyr Ser Ile Asp Ser Ser Thr Gly
        195                 200                 205

Phe Arg Val Asp Ser Ile Thr Gly Leu Pro Thr Asp Pro Tyr Pro Asn
210                 215                 220

Cys Pro Phe Asn Pro Val Thr Gly Asn Leu Val Ser Arg Ser Thr Gly
225                 230                 235                 240

Lys Thr Ile Pro Asn Thr Tyr Ala Gly Val Tyr Arg Ser Asn Glu Thr
                245                 250                 255

Lys Thr Thr Glu Pro Ser Ala Asn Thr Asn Phe Leu Leu Val Asp Pro
            260                 265                 270

Lys Ile Asn Ala Pro Cys Asn Ser Glu Asn Ser Phe Glu Gln Val Gln
            275                 280                 285

Ile Phe Asp Met Gly Ser Lys Val Tyr Ile Pro Tyr Thr Lys Cys Val
            290                 295                 300

Gly Val Lys His Thr Thr Thr Thr Thr Thr Thr Thr Thr Thr Thr Thr
305                 310                 315                 320

Thr Thr Thr Thr Thr Thr Thr Thr Thr Thr Thr Thr Thr Thr Thr Thr
                325                 330                 335

Thr Thr Thr Thr Thr Thr Thr Thr Thr Thr Thr Thr Thr Thr Thr Thr
            340                 345                 350

Thr Thr Thr Thr Thr Thr Thr Thr Thr Thr Thr Thr Thr Thr Thr Thr
            355                 360                 365

Thr Thr Thr Thr Thr Thr Lys Lys Pro Thr Thr Thr Thr Thr Thr Thr
            370                 375                 380

Thr Thr Thr Thr Thr Thr Thr Thr Thr Thr Thr Thr Thr Thr Thr Thr
385                 390                 395                 400

Thr Thr Thr Thr Thr Thr Thr Thr Thr Thr Thr Thr Thr Thr Thr Thr
                405                 410                 415

Thr Thr Thr Thr Thr Lys Lys Pro Thr Thr Thr Thr Thr Thr Thr Thr
            420                 425                 430

Thr Thr Thr Thr Thr Thr Thr Thr Thr Thr Thr Thr Thr Thr Thr Thr
            435                 440                 445

Thr Thr Thr Thr Thr Lys Lys Pro Thr Thr Thr Thr Thr Thr Thr Thr
450                 455                 460

Thr Thr Thr Thr Thr Thr Thr Thr Thr Thr Thr Thr Thr Thr Thr Thr
465                 470                 475                 480

Thr Thr Thr Thr Thr Thr Thr Thr Thr Ala Thr Thr Thr Thr Lys Lys
                485                 490                 495

Pro Thr Thr Thr Thr Thr Thr Thr Thr Thr Thr Thr Lys Lys Pro
            500                 505                 510

Thr Thr Thr Thr Thr Ala Thr Thr Thr Thr Thr Thr Ser Glu Thr Glu
            515                 520                 525

Ser Val Ile Lys Pro Asp Glu Trp Cys Trp Leu Glu Lys Asn Gly Glu
            530                 535                 540

Cys Glu Ala Lys Gly Ala Thr Tyr Val Gly Val Ile Gly Lys Asp Gly
545                 550                 555                 560

Arg Ile Glu Asn Gly Met Ala Phe Thr Met Ile Pro Asn Asp Asp Thr
                565                 570                 575

His Val Arg Phe Arg Phe Lys Val Lys Asp Val Gly Asn Thr Ile Ser
            580                 585                 590
```

```
Val Arg Cys Gly Lys Gly Ala Gly Lys Leu Glu Phe Pro Asp Arg Ser
        595                 600                 605
Leu Asp Phe Thr Ile Pro Pro Val Ala Gly His Asn Ser Cys Ser Ile
610                 615                 620
Ile Val Gly Val Ser Gly Gly Lys Ile His Val Ser Pro Tyr Gly
625                 630                 635                 640
Ser Lys Asp Val Ser Leu Ile Ser Ala Pro Ile Gln Pro Cys Glu Leu
                645                 650                 655
Phe Asn Glu Val Tyr Cys Asp Thr Cys Thr Ala Lys Tyr Gly Ala Ile
                660                 665                 670
His Ser Gly Tyr Gln Thr Ser Ala Asp Phe Val Thr Thr Thr Ala
        675                 680                 685
Lys Pro Thr Thr Thr Thr Gly Ala Pro Gly Gln Pro Thr Thr Thr
        690                 695                 700
Thr Thr Gly Ser Pro Ser Lys Pro Thr Thr Thr Thr Thr Lys Ala
705                 710                 715                 720
Thr Thr Thr Thr Thr Ile Leu Asn Pro Ile Ile Thr Thr Thr Gln
                725                 730                 735
Lys Pro Thr Thr Thr Thr Thr Lys Val Pro Gly Lys Pro Pro Ile
        740                 745                 750
Ala Thr Thr Thr Thr Leu Lys Pro Ile Val Thr Thr Thr Thr
        755                 760                 765
Lys Ala Thr Thr Thr Thr Thr Thr Val Pro Thr Thr Thr Thr Thr
770                 775                 780
Thr Lys Arg Asp Glu Met Thr Thr Thr Thr Pro Leu Pro Asp Ile
785                 790                 795                 800
Gly Asp Ile Glu Ile Thr Pro Ile Pro Ile Glu Lys Met Leu Asp Lys
                805                 810                 815
Tyr Thr Arg Met Ile Tyr Asp Tyr Asn Ser Gly Leu Leu Leu Asp Ser
                820                 825                 830
Asn Asp Glu Pro Ile Pro Gly Ser Gln Ala Gly Gln Ile Ala Asp Thr
        835                 840                 845
Ser Asn Leu Phe Pro Val Gln Thr His Lys Ser Thr Gly Leu Pro Ile
850                 855                 860
Asp Pro Met Val Gly Leu Pro Phe Asp Pro Lys Ser Gly Asn Leu Val
865                 870                 875                 880
His Pro Tyr Thr Asn Gln Thr Met Ser Gly Leu Ser Val Ser Tyr Leu
                885                 890                 895
Ala Ala Lys Asn Leu Thr Val Asp Thr Asp Glu Thr Tyr Gly Leu Pro
        900                 905                 910
Ile Asp Thr Leu Thr Gly Tyr Pro Leu Asp Pro Val Ser Leu Ile Pro
        915                 920                 925
Phe Asn Pro Glu Thr Gly Glu Leu Phe Asp Pro Ile Ser Asp Glu Ile
        930                 935                 940
Met Asn Gly Thr Ile Ala Gly Ile Val Ser Gly Ile Ser Ala Ser Glu
945                 950                 955                 960
Ser Leu Leu Ser Gln Lys Ser Ala Pro Ile Asp Pro Ala Thr Asn Met
                965                 970                 975
Val Val Gly Glu Phe Gly Gly Leu Leu Asn Pro Ala Thr Gly Val Met
                980                 985                 990
Ile Pro Gly Ser Leu Gly Pro Ser Glu Gln Thr Pro Phe Ser Pro Glu
        995                 1000                1005
```

```
Ile Glu Asp Gly Gly Ile Ile Pro Glu Val Ala Ala Asn Ala
    1010            1015                1020

Asp Lys Phe Lys Leu Ser Ile Pro Pro Ser Val Pro Glu Ser Ile Pro
1025            1030            1035                1040

Glu Lys Asp Gln Lys Ile Asp Ser Ile Ser Glu Leu Met Tyr Asp Ile
                1045            1050                1055

Glu Ser Gly Arg Leu Ile Gly Gln Val Ser Lys Arg Pro Ile Pro Gly
            1060            1065            1070

Ser Ile Ala Gly Asp Leu Asn Pro Ile Met Lys Thr Pro Thr Gln Thr
        1075            1080            1085

Asp Ser Val Thr Gly Lys Pro Ile Asp Pro Thr Thr Gly Leu Pro Phe
    1090            1095            1100

Asn Pro Pro Thr Gly His Leu Ile Asn Pro Thr Asn Asn Thr Met
1105            1110            1115            1120

Asp Ser Ser Phe Ala Gly Ala Tyr Lys Tyr Ala Val Ser Asn Gly Ile
            1125            1130            1135

Lys Thr Asp Asn Val Tyr Gly Leu Pro Val Asp Glu Ile Thr Gly Leu
        1140            1145            1150

Pro Lys Asp Pro Val Ser Asp Ile Pro Phe Asn Ser Thr Thr Gly Glu
    1155            1160            1165

Leu Val Asp Pro Ser Thr Gly Lys Pro Ile Asn Asn Tyr Thr Ala Gly
        1170            1175            1180

Ile Val Ser Gly Lys Arg Gly Leu Pro Pro Ile Glu Asp Glu Asn Gly
1185            1190            1195            1200

Asn Leu Phe Asp Pro Ser Thr Lys Leu Pro Ile Asp Gly Asn Asn Gln
            1205            1210            1215

Leu Val Asn Pro Glu Thr Asn Ser Thr Val Ser Gly Ser Thr Ser Gly
        1220            1225            1230

Ser Thr Lys Pro Lys Pro Gly Ile Pro Val Asn Gly Gly Val Val
        1235            1240            1245

Pro Asp Glu Glu Ala Lys Asp Gln Ala Asp Lys Gly Lys Asp Gly Leu
    1250            1255            1260

Ile Val Pro Pro Thr Asn Ser Ile Asn Lys Asp Pro Val Thr Asn Thr
1265            1270            1275            1280

Gln Tyr Ser Asn Thr Thr Gly Asn Ile Ile Asn Pro Glu Thr Gly Lys
            1285            1290            1295

Val Ile Pro Gly Ser Leu Pro Gly Ser Leu Asn Tyr Pro Ser Phe Asn
        1300            1305            1310

Thr Pro Gln Gln Thr Asp Glu Ile Thr Gly Lys Pro Val Asp Thr Val
    1315            1320            1325

Thr Gly Leu Pro Tyr Asp Pro Ser Thr Gly Glu Ile Ile Asp Pro Ala
    1330            1335            1340

Thr Lys Leu Pro Ile Pro Gly Ser Val Ala Gly Asp Glu Ile Leu Thr
1345            1350            1355            1360

Glu Val Leu Asn Ile Thr Thr Asp Glu Val Thr Gly Leu Pro Ile Asp
            1365            1370            1375

Leu Glu Thr Gly Leu Pro Arg Asp Pro Val Ser Gly Leu Pro Gln Leu
        1380            1385            1390

Pro Asn Gly Thr Leu Val Asp Pro Ser Asn Lys Pro Ile Pro Gly
        1395            1400            1405

Ser His Ser Gly Phe Ile Asn Gly Thr Ser Gly Glu Gln Ser His Glu
    1410            1415            1420

Lys Asp Pro Ser Thr Gly Lys Pro Leu Asp Pro Asn Thr Gly Leu Pro
```

```
                1425                1430                1435                1440
         Phe Asp Glu Asp Ser Gly Ser Leu Ile Asn Pro Glu Thr Gly Asp Lys
                             1445                1450                1455

Leu Gln Gly Ser His Ser Gly Thr Phe Met Pro Val Pro Gly Lys Pro
                        1460                1465                1470

Gln Gly Glu Asn Gly Gly Ile Met Thr Pro Glu Gln Ile Leu Glu Ala
                        1475                1480                1485

Leu Asn Lys Leu Pro Thr Ser Asn Glu Val Asn Ile Ser Pro Arg Pro
                        1490                1495                1500

Ser Ser Asp Ala Val Pro Asp Arg Pro Thr Asn Thr Trp Trp Asn Lys
         1505                1510                1515                1520

Ile Ser Gly Gln Thr Phe Gln Val Asp Gly Lys Lys Thr Ile Pro Gly
                        1525                1530                1535

Ser Ala Ala Ser Val Ile His Thr Ala Leu Gly Thr Pro Thr Gln Thr
                        1540                1545                1550

Asp Pro Thr Thr Gly Leu Pro Ser Asp Pro Ser Thr Gly Leu Pro Phe
                        1555                1560                1565

Ile Pro Gly Phe Asn Val Leu Val Asp Pro Gln Thr Gly Glu Gln Ile
                   1570                1575                1580

Lys Gly Ser Val Pro Tyr Val Ser Leu Tyr Val Lys Glu Lys Asn Ile
         1585                1590                1595                1600

Val Thr Glu Ala Ala Tyr Gly Leu Pro Val Asp Pro Lys Thr Gly Phe
                        1605                1610                1615

Pro Ile Asp Pro Ile Ser Tyr Leu Pro Phe Ala Lys Asn Gly Glu Leu
                   1620                1625                1630

Ile Asp Pro Ile Ser Gly Lys Tyr Phe Ser Gly Ser Ile Ala Gly Phe
                   1635                1640                1645

Ile Ser Gly Lys Ala Gly Ser Gln Ser Lys Ser Ser Asp Glu Ser Gly
                   1650                1655                1660

Asn Pro Ile Asp Pro Ser Thr Asn Met Pro Tyr Asp Pro Lys Thr Gly
         1665                1670                1675                1680

Lys Leu Ile Asp Pro Glu Ser Gly Ile Ala Ile Asp Asn Ser Val Ser
                        1685                1690                1695

Gly Val Phe Ala Thr Val Pro Gly Thr Ala Ala Pro Lys Lys Gly Gly
                        1700                1705                1710

Val Ile Pro Glu Ser Val Ala Ala Glu Ala Ala Lys Lys Tyr Phe Ala
                        1715                1720                1725

Ala Asn Val Glu Gly Glu Gly Glu Gly Glu Glu Val Pro Pro Pro Pro
                   1730                1735                1740

Glu Ser Ser Ser Asn Ile Ala Ile Gln Ala Ala Gly Gly Ala Ser Ala
         1745                1750                1755                1760

Ala Val Gly Leu Val Ala Ala Val Gly Ala Trp Tyr Ala Ser Arg Asn
                        1765                1770                1775

Arg Gln Glu Gly Glu Asp Asp Asp Tyr Gln Met Asp Leu Lys Gln
                   1780                1785                1790

Asn Met Lys Lys Lys Arg Lys Arg Val Met Lys Gln Gln Met Lys
                   1795                1800                1805

Leu Leu Leu Gln Leu Ser Val Ile His His Ser Gly Thr Asn Leu Lys
                   1810                1815                1820

Arg Arg Lys Asp Phe Ser Asn Ser Lys Lys Phe Arg Ile
         1825                1830                1835

(2) INFORMATION FOR SEQ ID NO:6:
```

(i) SEQUENCE CHARACTERISTICS:
    (A) LENGTH: 1721 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO:6:

```
Ile Leu Glu Gly Ser Ile Ala Gly Ile Arg Ser Glu Ser Cys Ile Val
1               5                   10                  15

Ser Glu Leu Asn Phe Thr Ser Thr Thr Gly Phe Thr Asp Thr Ser
            20                  25                  30

Met Asn Trp Pro Val Ser Ile Thr Ser Gly Glu Leu Lys Asp Pro Asn
            35                  40                  45

Lys Gln Ala Thr Ile Ser Gly Ser Arg Ser Cys Gly Trp Lys Gln Gly
            50                  55                  60

Tyr Ser Ile Asp Ser Ser Thr Gly Phe Arg Val Asp Ser Ile Thr Gly
65                  70                  75                  80

Leu Pro Thr Asp Pro Tyr Ser Asn Cys Pro Phe Asn Pro Val Thr Gly
                85                  90                  95

Asn Leu Val Ser Arg Ser Thr Gly Lys Thr Ile Pro Asn Thr Tyr Ala
                100                 105                 110

Gly Val Tyr Arg Ser Asn Glu Thr Lys Thr Thr Glu Pro Ser Ala Asn
                115                 120                 125

Thr Tyr Ala Gly Val Tyr Arg Ser Asn Glu Thr Lys Thr Thr Glu Pro
130                 135                 140

Ser Ala Asn Thr Asn Phe Leu Leu Val Asp Pro Lys Ile Asn Ala Pro
145                 150                 155                 160

Cys Asn Ser Glu Asn Ser Phe Glu Gln Gly Gln Ile Phe Asp Met Gly
                165                 170                 175

Ser Lys Val Tyr Ile Pro Tyr Thr Lys Cys Val Gly Val Lys His Thr
                180                 185                 190

Thr Thr Thr Thr Thr Thr Thr Thr Thr Thr Thr Thr Thr Thr Thr
                195                 200                 205

Thr Thr Thr Thr Thr Thr Thr Thr Thr Thr Thr Thr Thr Thr Thr
                210                 215                 220

Thr Thr Thr Thr Thr Thr Thr Thr Thr Thr Thr Thr Thr Thr Thr Thr
225                 230                 235                 240

Thr Thr Thr Thr Thr Thr Thr Thr Thr Thr Thr Thr Thr Thr Thr
                245                 250                 255

Thr Thr Thr Thr Thr Thr Thr Thr Thr Thr Thr Thr Thr Thr Thr
                260                 265                 270

Thr Thr Thr Thr Thr Thr Thr Thr Thr Thr Thr Thr Thr Thr Thr
                275                 280                 285

Thr Thr Thr Thr Thr Thr Thr Thr Thr Thr Thr Thr Thr Thr Thr
                290                 295                 300

Lys Lys Pro Thr Thr Thr Thr Thr Thr Thr Thr Thr Thr Thr Thr Thr
305                 310                 315                 320

Thr Thr Thr Thr Thr Thr Thr Thr Thr Thr Thr Thr Thr Thr Thr
                325                 330                 335

Lys Lys Pro Thr Thr Thr Thr Thr Thr Thr Thr Thr Thr Thr Thr
                340                 345                 350

Thr Thr Thr Thr Thr Thr Thr Thr Thr Thr Thr Thr Thr Thr Thr
                355                 360                 365
```

```
-continued

Thr Thr Thr Thr Thr Thr Thr Thr Thr Lys Pro Thr Thr Thr Thr
370                 375                 380

Thr Thr Thr Thr Thr Thr Thr Thr Lys Lys Pro Thr Thr Thr Thr
385                 390                 395                 400

Ala Thr Thr Thr Thr Thr Thr Ser Glu Thr Glu Ser Val Ile Lys Pro
                    405                 410                 415

Asp Glu Trp Cys Trp Leu Glu Lys Asn Gly Glu Cys Glu Ala Lys Gly
            420                 425                 430

Ala Thr Tyr Val Gly Val Ile Gly Lys Asp Gly Arg Ile Glu Asn Gly
        435                 440                 445

Met Ala Phe Thr Met Ile Pro Asn Asp Asp Thr His Val Arg Phe Arg
450                 455                 460

Phe Lys Val Lys Asp Val Gly Asn Thr Ile Ser Val Arg Cys Arg Lys
465                 470                 475                 480

Gly Ala Gly Lys Leu Glu Phe Pro Asp Arg Ser Leu Asp Phe Thr Ile
                485                 490                 495

Pro Pro Val Ala Gly His Asn Ser Cys Ser Ile Ile Val Gly Val Ser
            500                 505                 510

Gly Asp Gly Lys Ile His Val Ser Pro Tyr Gly Ser Lys Asp Val Ser
        515                 520                 525

Leu Ile Ser Ala Pro Ile Gln Pro Ser Glu Leu Phe Asn Glu Val Tyr
530                 535                 540

Cys Asp Thr Cys Thr Ala Lys Tyr Gly Ala Ile His Ser Gly Tyr Gln
545                 550                 555                 560

Thr Ser Ala Asp Phe Val Thr Thr Thr Ala Lys Pro Thr Thr Thr
                565                 570                 575

Thr Thr Gly Ala Pro Gly Gln Pro Thr Thr Thr Thr Gly Ser Pro
            580                 585                 590

Ser Lys Pro Thr Thr Thr Thr Thr Lys Ala Thr Thr Thr Thr
        595                 600                 605

Thr Leu Asn Pro Ile Ile Thr Thr Thr Thr Gln Lys Pro Thr Thr Thr
610                 615                 620

Thr Thr Thr Lys Val Pro Gly Lys Pro Pro Ile Ala Thr Thr Thr Thr
625                 630                 635                 640

Thr Leu Lys Pro Ile Val Thr Thr Thr Thr Thr Lys Ala Thr Thr Thr
                645                 650                 655

Thr Thr Thr Thr Val Pro Thr Thr Thr Thr Thr Thr Lys Arg Asp Glu
            660                 665                 670

Met Thr Thr Thr Thr Thr Pro Leu Pro Asp Ile Gly Asp Ile Glu Ile
        675                 680                 685

Thr Pro Ile Pro Ile Glu Lys Met Leu Asp Lys Tyr Thr Arg Met Ile
690                 695                 700

Tyr Asp Tyr Asn Ser Gly Leu Leu Leu Asp Ser Asn Asp Glu Pro Ile
705                 710                 715                 720

Pro Gly Ser Gln Ala Gly Gln Ile Ala Asp Thr Ser Asn Leu Phe Pro
                725                 730                 735

Val Gln Thr His Lys Ser Thr Gly Leu Pro Ile Asp Pro Met Val Gly
            740                 745                 750

Leu Pro Phe Asp Pro Lys Ser Gly Asn Leu Val His Pro Tyr Thr Asn
        755                 760                 765

Gln Thr Met Ser Gly Leu Ser Val Ser Tyr Leu Ala Ala Lys Asn Leu
770                 775                 780
```

-continued

Thr Val Asp Thr Asp Glu Thr Tyr Gly Leu Pro Ile Asp Thr Leu Thr
785                 790                 795                 800

Gly Tyr Pro Leu Asp Pro Val Ser Leu Ile Pro Phe Asn Pro Glu Thr
            805                 810                 815

Gly Glu Leu Phe Asp Pro Ile Ser Asp Glu Ile Met Asn Gly Thr Ile
            820                 825                 830

Ala Gly Ile Val Ser Gly Ile Ser Ala Ser Glu Ser Leu Leu Ser Gln
            835                 840                 845

Lys Ser Ala Leu Ile Asp Pro Ala Thr Asn Met Val Val Gly Glu Phe
850                 855                 860

Gly Gly Leu Leu Asn Pro Ala Thr Gly Val Met Ile Pro Gly Phe Leu
865                 870                 875                 880

Gly Pro Ser Glu Gln Thr Gln Phe Ser Pro Glu Ile Glu Asp Gly Gly
            885                 890                 895

Ile Ile Pro Pro Glu Val Ala Ala Ala Asn Ala Asp Lys Phe Lys Leu
            900                 905                 910

Ser Ile Pro Pro Ser Val Pro Glu Ser Ile Pro Glu Lys Asp Gln Lys
            915                 920                 925

Ile Asp Ser Ile Ser Glu Leu Met Tyr Asp Ile Glu Ser Gly Arg Leu
930                 935                 940

Ile Gly Gln Val Ser Lys Arg Pro Ile Pro Gly Ser Ile Ala Gly Asp
945                 950                 955                 960

Leu Asn Pro Ile Met Lys Thr Pro Thr Gln Thr Asp Ser Val Thr Gly
            965                 970                 975

Lys Pro Ile Asp Pro Thr Thr Gly Leu Pro Phe Asn Pro Pro Thr Gly
            980                 985                 990

His Leu Ile Asn Pro Thr Asn Asn Thr Met Asp Ser Ser Phe Ala
            995                 1000                1005

Gly Ala Tyr Lys Tyr Ala Val Ser Asn Gly Ile Lys Thr Asp Asn Val
    1010                1015                1020

Tyr Gly Leu Pro Val Gly Glu Ile Thr Gly Leu Pro Lys Asp Pro Gly
1025                1030                1035                1040

Ser Asp Ile Pro Phe Asn Ser Thr Thr Gly Glu Leu Val Asp Pro Ser
            1045                1050                1055

Thr Gly Lys Pro Ile Asn Asn Ser Thr Ala Gly Ile Val Ser Gly Lys
            1060                1065                1070

Pro Gly Leu Pro Pro Ile Glu Asp Glu Asn Gly Asn Leu Phe Asp Pro
    1075                1080                1085

Ser Thr Asn Leu Pro Ile Asp Gly Asn Asn Gln Leu Val Asn Pro Glu
    1090                1095                1100

Thr Asn Ser Thr Val Ser Gly Ser Thr Ser Gly Thr Thr Lys Pro Lys
1105                1110                1115                1120

Pro Gly Ile Pro Val Asn Gly Gly Val Val Pro Asp Glu Glu Ala
    1125                1130                1135

Lys Asp Gln Ala Asp Lys Gly Lys Asp Gly Leu Ile Val Pro Pro Thr
            1140                1145                1150

Asn Ser Ile Asn Lys Asp Pro Val Thr Asn Thr Gln Tyr Ser Asn Thr
        1155                1160                1165

Thr Gly Asn Ile Ile Asn Pro Glu Thr Gly Lys Val Ile Pro Gly Ser
    1170                1175                1180

Leu Pro Gly Ser Leu Asn Tyr Pro Ser Phe Asn Thr Pro Gln Gln Thr
1185                1190                1195                1200

Asp Glu Ile Thr Gly Lys Pro Val Asp Thr Val Thr Gly Leu Pro Tyr

-continued

```
                  1205                1210                1215
Asp Pro Ser Thr Gly Glu Ile Ile Asp Pro Ala Thr Lys Leu Pro Ile
                  1220                1225                1230

Pro Gly Ser Val Ala Gly Asp Glu Ile Leu Thr Glu Val Leu Asn Ile
                  1235                1240                1245

Thr Thr Asp Glu Val Thr Gly Leu Pro Ile Asp Leu Glu Thr Gly Leu
                  1250                1255                1260

Pro Arg Asp Pro Val Ser Gly Leu Pro Gln Leu Pro Asn Gly Thr Leu
1265                1270                1275                1280

Val Asp Pro Ser Asn Lys Lys Pro Ile Pro Gly Ser His Ser Gly Phe
                  1285                1290                1295

Ile Asn Gly Thr Ser Gly Glu Gln Ser His Glu Lys Asp Pro Ser Thr
                  1300                1305                1310

Gly Lys Pro Leu Asp Pro Asn Thr Gly Leu His Pro Phe Asp Glu Asp
                  1315                1320                1325

Ser Gly Ser Leu Ile Asn Pro Glu Thr Gly Asp Lys Leu Gln Gly Ser
                  1330                1335                1340

His Ser Gly Thr Phe Met Pro Val Pro Gly Lys Pro Gln Gly Glu Asn
1345                1350                1355                1360

Gly Gly Ile Met Thr Pro Glu Gln Ile Leu Glu Ala Leu Asn Lys Leu
                  1365                1370                1375

Pro Thr Ser Asn Glu Val Asn Ile Ser Pro Arg Pro Ser Ser Asp Ala
                  1380                1385                1390

Val Pro Asp Arg Pro Thr Asn Thr Trp Trp Asn Lys Ile Ser Gly Gln
                  1395                1400                1405

Thr Tyr Gln Val Asp Gly Lys Lys Thr Ile Pro Gly Ser Ala Ala Ser
                  1410                1415                1420

Val Ile His Thr Ala Leu Gly Thr Pro Thr Gln Thr Asp Pro Thr Thr
1425                1430                1435                1440

Gly Leu Pro Ser Asp Pro Ser Thr Gly Leu Pro Phe Ile Pro Gly Phe
                  1445                1450                1455

Asn Val Leu Val Asp Pro Gln Thr Gly Glu Gln Ile Lys Gly Ser Val
                  1460                1465                1470

Pro Tyr Val Ser Leu Tyr Val Lys Glu Lys Asn Ile Val Thr Glu Ala
                  1475                1480                1485

Ala Tyr Gly Leu Pro Val Asp Pro Lys Thr Gly Phe Pro Ile Asp Pro
                  1490                1495                1500

Ile Ser Tyr Leu Pro Phe Ala Lys Asn Gly Glu Leu Ile Asp Pro Ile
1505                1510                1515                1520

Ser Gly Lys Tyr Phe Ser Gly Ser Ile Ala Gly Phe Ile Ser Gly Lys
                  1525                1530                1535

Ala Gly Ser Gln Ser Lys Ser Ser Asp Glu Ser Gly Asn Pro Ile Asp
                  1540                1545                1550

Pro Ser Thr Asn Met Pro Tyr Asp Pro Lys Gly Gly Lys Leu Ile Asp
                  1555                1560                1565

Pro Glu Ser Gly Ile Ala Ile Asp Asn Ser Val Ser Gly Val Phe Ala
                  1570                1575                1580

Thr Val Pro Gly Thr Ala Ala Pro Lys Lys Gly Val Ile Pro Glu
1585                1590                1595                1600

Ser Val Ala Ala Glu Ala Ala Lys Lys Tyr Phe Ala Ala Asn Val Glu
                  1605                1610                1615

Gly Glu Gly Glu Gly Glu Glu Val Pro Pro Pro Glu Ser Ser Ser
                  1620                1625                1630
```

```
Asn Ile Ala Ile Gln Ala Ala Gly Gly Ala Ser Ala Ala Val Gly Leu
            1635                1640                1645

Val Ala Ala Val Gly Ala Trp Tyr Ala Ser Arg Asn Arg Gln Glu Gly
1650                1655                1660

Glu Asp Asp Asp Tyr Gln Met Asp Leu Lys Gln Asn Met Lys Lys
1665                1670                1675                1680

Lys Arg Lys Lys Arg Val Met Lys Gln Gln Met Lys Leu Leu Leu Gln
                1685                1690                1695

Leu Ser Val Ile His His Ser Gly Thr Asn Leu Lys Arg Arg Lys Asp
            1700                1705                1710

Phe Ser Asn Ser Lys Lys Phe Arg Ile
            1715                1720

(2) INFORMATION FOR SEQ ID NO:7:

(i) SEQUENCE CHARACTERISTICS:
        (A) LENGTH: 303 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

Met Val Asn Ile Lys Val Ser Ser Ala Ile Ala Leu Val Ala Val
1               5                   10                  15

Ile Met Asn Pro Leu Phe Ser Leu Ala Phe Lys Ser Ser Asn Arg Leu
            20                  25                  30

Glu Met Arg Ile Glu Ser Ser Gly Ala Val Ser Asn Glu Lys Phe Val
            35                  40                  45

Ile Pro Ser Leu Pro Ser Asp Leu Asp Pro Thr Thr Phe Leu Leu Ile
50                  55                  60

Asp Ser Thr Gly Lys Lys Phe Ser Pro Tyr Thr Gly Lys His Ala Asp
65                  70                  75                  80

Ala Ser Thr Thr Ser Ser Ala Tyr Ser Ala Pro Phe Glu Leu Asp Val
                85                  90                  95

Ser Gly Val Pro Ile Glu Pro Asn Thr Arg Arg Met Val Asp Pro Val
                100                 105                 110

Ser Leu Met Leu Phe Asp Asn Ser Thr Gly Val Met Tyr Asp Pro Asn
            115                 120                 125

Thr Asn Ser Ile Leu Glu Gly Ser Ile Ala Gly Ile Arg Ser Glu Ser
130                 135                 140

Cys Ile Val Ser Glu Leu Asn Phe Thr Ser Thr Thr Gly Phe Thr Thr
145                 150                 155                 160

Asp Thr Ser Met Asn Trp Pro Val Ser Ile Thr Ser Gly Glu Leu Lys
                165                 170                 175

Asp Pro Asn Lys Gln Ala Thr Ile Ser Gly Ser Arg Ser Cys Gly Trp
            180                 185                 190

Lys Gln Gly Tyr Ser Ile Asp Ser Ser Thr Gly Phe Arg Val Asp Ser
            195                 200                 205

Ile Thr Gly Leu Pro Thr Asp Pro Tyr Pro Asn Cys Pro Phe Asn Pro
        210                 215                 220

Val Thr Gly Asn Leu Val Ser Arg Ser Thr Gly Lys Thr Ile Pro Asn
225                 230                 235                 240

Thr Tyr Ala Gly Val Tyr Arg Ser Asn Glu Thr Lys Thr Thr Glu Pro
                245                 250                 255
```

```
Ser Ala Asn Thr Asn Phe Leu Leu Val Asp Pro Lys Ile Asn Ala Pro
        260                 265                 270

Cys Asn Ser Glu Asn Ser Phe Glu Gln Val Gln Ile Phe Asp Met Gly
        275                 280                 285

Ser Lys Val Tyr Ile Pro Tyr Thr Lys Cys Val Gly Val Lys His
        290                 295                 300
```

(2) INFORMATION FOR SEQ ID NO:8:

(i) SEQUENCE CHARACTERISTICS:
        (A) LENGTH: 216 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

```
Thr Thr Thr Thr Thr Thr Thr Thr Thr Thr Thr Thr Thr Thr Thr Thr
1               5                   10                  15

Thr Thr Thr Thr Thr Thr Thr Thr Thr Thr Thr Thr Thr Thr Thr Thr
        20                  25                  30

Thr Thr Thr Thr Thr Thr Thr Thr Thr Thr Thr Thr Thr Thr Thr Thr
        35                  40                  45

Thr Thr Thr Thr Thr Thr Thr Thr Thr Thr Thr Thr Thr Thr Thr Thr
        50                  55                  60

Thr Thr Thr Lys Lys Pro Thr Thr Thr Thr Thr Thr Thr Thr Thr Thr
65                  70                  75                  80

Thr Thr Thr Thr Thr Thr Thr Thr Thr Thr Thr Thr Thr Thr Thr Thr
        85                  90                  95

Thr Thr Thr Thr Thr Thr Thr Thr Thr Thr Thr Thr Thr Thr Thr Thr
        100                 105                 110

Thr Lys Lys Pro Thr Thr Thr Thr Thr Thr Thr Thr Thr Thr Thr Thr
        115                 120                 125

Thr Thr Thr Thr Thr Thr Thr Thr Thr Thr Thr Thr Thr Thr Thr Thr
        130                 135                 140

Thr Lys Lys Pro Thr Thr Thr Thr Thr Thr Thr Thr Thr Thr Thr Thr
145                 150                 155                 160

Thr Thr Thr Thr Thr Thr Thr Thr Thr Thr Thr Thr Thr Thr Thr Thr
        165                 170                 175

Thr Thr Thr Thr Thr Ala Thr Thr Thr Thr Lys Lys Pro Thr Thr Thr
        180                 185                 190

Thr Thr Thr Thr Thr Thr Thr Thr Thr Lys Lys Pro Thr Thr Thr Thr
        195                 200                 205

Thr Ala Thr Thr Thr Thr Thr Thr
        210                 215
```

(2) INFORMATION FOR SEQ ID NO:9:

(i) SEQUENCE CHARACTERISTICS:
        (A) LENGTH: 159 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:9:

Ser Glu Thr Glu Ser Val Ile Lys Pro Asp Glu Trp Cys Trp Leu Glu

```
                1               5                  10                 15
Lys Asn Gly Glu Cys Glu Ala Lys Gly Ala Thr Tyr Val Gly Val Ile
                    20              25              30

Gly Lys Asp Gly Arg Ile Glu Asn Gly Met Ala Phe Thr Met Ile Pro
            35                  40                  45

Asn Asp Asp Thr His Val Arg Phe Arg Phe Lys Val Lys Asp Val Gly
        50                  55                  60

Asn Thr Ile Ser Val Arg Cys Gly Lys Gly Ala Gly Lys Leu Glu Phe
65                      70              75                      80

Pro Asp Arg Ser Leu Asp Phe Thr Ile Pro Pro Val Ala Gly His Asn
                    85                  90                  95

Ser Cys Ser Ile Ile Val Gly Val Ser Gly Gly Lys Ile His Val
                100                 105                 110

Ser Pro Tyr Gly Ser Lys Asp Val Ser Leu Ile Ser Ala Pro Ile Gln
                    115                 120                 125

Pro Cys Glu Leu Phe Asn Glu Val Tyr Cys Asp Thr Cys Thr Ala Lys
            130                 135                 140

Tyr Gly Ala Ile His Ser Gly Tyr Gln Thr Ser Ala Asp Phe Val
145                     150                 155

(2) INFORMATION FOR SEQ ID NO:10:

(i) SEQUENCE CHARACTERISTICS:
        (A) LENGTH: 112 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:10:

Thr Thr Thr Thr Ala Lys Pro Thr Thr Thr Thr Thr Gly Ala Pro Gly
1               5                   10                  15

Gln Pro Thr Thr Thr Thr Thr Gly Ser Pro Ser Lys Pro Thr Thr Thr
                20                  25                  30

Thr Thr Thr Lys Ala Thr Thr Thr Thr Ile Leu Asn Pro Ile Ile
            35                  40                  45

Thr Thr Thr Thr Gln Lys Pro Thr Thr Thr Thr Thr Lys Val Pro
        50                  55                  60

Gly Lys Pro Pro Ile Ala Thr Thr Thr Thr Leu Lys Pro Ile Val
65                  70                  75                      80

Thr Thr Thr Thr Thr Lys Ala Thr Thr Thr Thr Thr Thr Val Pro
                85                  90                  95

Thr Thr Thr Thr Thr Thr Lys Arg Asp Glu Met Thr Thr Thr Thr
                100                 105                 110

(2) INFORMATION FOR SEQ ID NO:11:

(i) SEQUENCE CHARACTERISTICS:
        (A) LENGTH: 1042 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:11:

Pro Leu Pro Asp Ile Gly Asp Ile Glu Ile Thr Pro Ile Pro Ile Glu
1               5                   10                  15
```

-continued

```
Lys Met Leu Asp Lys Tyr Thr Arg Met Ile Tyr Asp Tyr Asn Ser Gly
             20                  25                  30

Leu Leu Leu Asp Ser Asn Asp Glu Pro Ile Pro Gly Ser Gln Ala Gly
             35                  40                  45

Gln Ile Ala Asp Thr Ser Asn Leu Phe Pro Val Gln Thr His Lys Ser
             50                  55                  60

Thr Gly Leu Pro Ile Asp Pro Met Val Gly Leu Pro Phe Asp Pro Lys
 65                  70                  75                  80

Ser Gly Asn Leu Val His Pro Tyr Thr Asn Gln Thr Met Ser Gly Leu
                     85                  90                  95

Ser Val Ser Tyr Leu Ala Ala Lys Asn Leu Thr Val Asp Thr Asp Glu
            100                 105                 110

Thr Tyr Gly Leu Pro Ile Asp Thr Leu Thr Gly Tyr Pro Leu Asp Pro
            115                 120                 125

Val Ser Leu Ile Pro Phe Asn Pro Glu Thr Gly Glu Leu Phe Asp Pro
            130                 135                 140

Ile Ser Asp Glu Ile Met Asn Gly Thr Ile Ala Gly Ile Val Ser Gly
145                 150                 155                 160

Ile Ser Ala Ser Glu Ser Leu Leu Ser Gln Lys Ser Ala Pro Ile Asp
                165                 170                 175

Pro Ala Thr Asn Met Val Val Gly Glu Phe Gly Gly Leu Leu Asn Pro
            180                 185                 190

Ala Thr Gly Val Met Ile Pro Gly Ser Leu Gly Pro Ser Glu Gln Thr
            195                 200                 205

Pro Phe Ser Pro Glu Ile Glu Asp Gly Gly Ile Ile Pro Pro Glu Val
            210                 215                 220

Ala Ala Ala Asn Ala Asp Lys Phe Lys Leu Ser Ile Pro Pro Ser Val
225                 230                 235                 240

Pro Glu Ser Ile Pro Glu Lys Asp Gln Lys Ile Asp Ser Ile Ser Glu
                245                 250                 255

Leu Met Tyr Asp Ile Glu Ser Gly Arg Leu Ile Gly Gln Val Ser Lys
            260                 265                 270

Arg Pro Ile Pro Gly Ser Ile Ala Gly Asp Leu Asn Pro Ile Met Lys
            275                 280                 285

Thr Pro Thr Gln Thr Asp Ser Val Thr Gly Lys Pro Ile Asp Pro Thr
            290                 295                 300

Thr Gly Leu Pro Phe Asn Pro Pro Thr Gly His Leu Ile Asn Pro Thr
305                 310                 315                 320

Asn Asn Asn Thr Met Asp Ser Ser Phe Ala Gly Ala Tyr Lys Tyr Ala
                325                 330                 335

Val Ser Asn Gly Ile Lys Thr Asp Asn Val Tyr Gly Leu Pro Val Asp
            340                 345                 350

Glu Ile Thr Gly Leu Pro Lys Asp Pro Val Ser Asp Ile Pro Phe Asn
            355                 360                 365

Ser Thr Thr Gly Glu Leu Val Asp Pro Ser Thr Gly Lys Pro Ile Asn
            370                 375                 380

Asn Tyr Thr Ala Gly Ile Val Ser Gly Lys Arg Gly Leu Pro Pro Ile
385                 390                 395                 400

Glu Asp Glu Asn Gly Asn Leu Phe Asp Pro Ser Thr Lys Leu Pro Ile
                405                 410                 415

Asp Gly Asn Asn Gln Leu Val Asn Pro Glu Thr Asn Ser Thr Val Ser
            420                 425                 430

Gly Ser Thr Ser Gly Ser Thr Lys Pro Lys Pro Gly Ile Pro Val Asn
```

-continued

```
            435                 440                 445
Gly Gly Gly Val Pro Asp Glu Ala Lys Asp Gln Ala Asp Lys
        450                 455                 460

Gly Lys Asp Gly Leu Ile Val Pro Pro Thr Asn Ser Ile Asn Lys Asp
465                 470                 475                 480

Pro Val Thr Asn Thr Gln Tyr Ser Asn Thr Gly Asn Ile Ile Asn
                485                 490                 495

Pro Glu Thr Gly Lys Val Ile Pro Gly Ser Leu Pro Gly Ser Leu Asn
            500                 505                 510

Tyr Pro Ser Phe Asn Thr Pro Gln Gln Thr Asp Glu Ile Thr Gly Lys
            515                 520                 525

Pro Val Asp Thr Val Thr Gly Leu Pro Tyr Asp Pro Ser Thr Gly Glu
    530                 535                 540

Ile Ile Asp Pro Ala Thr Lys Leu Pro Ile Pro Gly Ser Val Ala Gly
545                 550                 555                 560

Asp Glu Ile Leu Thr Glu Val Leu Asn Ile Thr Thr Asp Glu Val Thr
                565                 570                 575

Gly Leu Pro Ile Asp Leu Glu Thr Gly Leu Pro Arg Asp Pro Val Ser
            580                 585                 590

Gly Leu Pro Gln Leu Pro Asn Gly Thr Leu Val Asp Pro Ser Asn Lys
    595                 600                 605

Lys Pro Ile Pro Gly Ser His Ser Gly Phe Ile Asn Gly Thr Ser Gly
610                 615                 620

Glu Gln Ser His Glu Lys Asp Pro Ser Thr Gly Lys Pro Leu Asp Pro
625                 630                 635                 640

Asn Thr Gly Leu Pro Phe Asp Glu Asp Ser Gly Ser Leu Ile Asn Pro
                645                 650                 655

Glu Thr Gly Asp Lys Leu Gln Gly Ser His Ser Gly Thr Phe Met Pro
            660                 665                 670

Val Pro Gly Lys Pro Gln Gly Glu Asn Gly Gly Ile Met Thr Pro Glu
    675                 680                 685

Gln Ile Leu Glu Ala Leu Asn Lys Leu Pro Thr Ser Asn Glu Val Asn
690                 695                 700

Ile Ser Pro Arg Pro Ser Ser Asp Ala Val Pro Asp Arg Pro Thr Asn
705                 710                 715                 720

Thr Trp Trp Asn Lys Ile Ser Gly Gln Thr Phe Gln Val Asp Gly Lys
                725                 730                 735

Lys Thr Ile Pro Gly Ser Ala Ala Ser Val Ile His Thr Ala Leu Gly
            740                 745                 750

Thr Pro Thr Gln Thr Asp Pro Thr Thr Gly Leu Pro Ser Asp Pro Ser
    755                 760                 765

Thr Gly Leu Pro Phe Ile Pro Gly Phe Asn Val Leu Val Asp Pro Gln
770                 775                 780

Thr Gly Glu Gln Ile Lys Gly Ser Val Pro Tyr Val Ser Leu Tyr Val
785                 790                 795                 800

Lys Glu Lys Asn Ile Val Thr Glu Ala Ala Tyr Gly Leu Pro Val Asp
                805                 810                 815

Pro Lys Thr Gly Phe Pro Ile Asp Pro Ile Ser Tyr Leu Pro Phe Ala
            820                 825                 830

Lys Asn Gly Glu Leu Ile Asp Pro Ile Ser Gly Lys Tyr Phe Ser Gly
    835                 840                 845

Ser Ile Ala Gly Phe Ile Ser Gly Lys Ala Gly Ser Gln Ser Lys Ser
850                 855                 860
```

```
Ser Asp Glu Ser Gly Asn Pro Ile Asp Pro Ser Thr Asn Met Pro Tyr
865                 870                 875                 880

Asp Pro Lys Thr Gly Lys Leu Ile Asp Pro Glu Ser Gly Ile Ala Ile
                885                 890                 895

Asp Asn Ser Val Ser Gly Val Phe Ala Thr Val Pro Gly Thr Ala Ala
            900                 905                 910

Pro Lys Lys Gly Gly Val Ile Pro Glu Ser Val Ala Ala Glu Ala Ala
            915                 920                 925

Lys Lys Tyr Phe Ala Ala Asn Val Glu Gly Gly Glu Gly Glu Glu
930                 935                 940

Val Pro Pro Pro Glu Ser Ser Ser Asn Ile Ala Ile Gln Ala Ala
945                 950                 955                 960

Gly Gly Ala Ser Ala Ala Val Gly Leu Val Ala Ala Val Gly Ala Trp
                965                 970                 975

Tyr Ala Ser Arg Asn Arg Gln Glu Gly Glu Asp Asp Asp Tyr Gln
                980                 985                 990

Met Asp Leu Lys Gln Asn Met Lys Lys Lys Arg Lys Lys Arg Val Met
            995                 1000                1005

Lys Gln Gln Met Lys Leu Leu Leu Gln Leu Ser Val Ile His His Ser
    1010                1015                1020

Gly Thr Asn Leu Lys Arg Arg Lys Asp Phe Ser Asn Ser Lys Lys Phe
1025                1030                1035                1040

Arg Ile (2) INFORMATION FOR SEQ ID NO:12:

(i) SEQUENCE CHARACTERISTICS:
        (A) LENGTH: 128 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:12:

Met Gly Ser Lys Val Tyr Ile Pro Tyr Thr Lys Cys Val Gly Val Lys
1               5                   10                  15

His Thr Thr Thr Thr Thr Thr Thr Thr Thr Thr Thr Thr Thr Thr
            20                  25                  30

Thr Thr Thr Thr Thr Thr Thr Thr Thr Thr Thr Thr Thr Thr Thr Thr
        35                  40                  45

Thr Thr Thr Thr Thr Thr Thr Thr Thr Thr Thr Thr Thr Thr Thr Thr
50                  55                  60

Thr Thr Thr Thr Thr Thr Thr Thr Thr Thr Thr Thr Thr Thr Thr Thr
65                  70                  75                  80

Thr Thr Lys Lys Pro Thr Thr Thr Thr Thr Thr Thr Thr Thr Thr Thr
                85                  90                  95

Thr Lys Lys Pro Thr Thr Thr Thr Thr Ala Thr Thr Thr Thr Thr Thr
            100                 105                 110

Ser Glu Thr Glu Ser Val Ile Lys Pro Asp Glu Trp Cys Trp Leu Glu
            115                 120                 125

(2) INFORMATION FOR SEQ ID NO:13:

(i) SEQUENCE CHARACTERISTICS:
        (A) LENGTH: 130 amino acids
        (B) TYPE: amino acid
```

(C) STRANDEDNESS:
        (D) TOPOLOGY: linear (ii) MOLECULE TYPE: protein (xi) SEQUENCE DESCRIPTION: SEQ ID NO:13:

Met Gly Ser Lys Val Tyr Ile Pro Tyr Thr Lys Cys Val Gly Val Lys
1               5                   10                  15

His Thr Thr Thr Thr Thr Thr Thr Thr Thr Thr Thr Thr Thr Thr Thr
                20                  25                  30

Thr Thr Thr Thr Thr Thr Thr Thr Thr Thr Thr Thr Thr Thr Thr Thr
            35                  40                  45

Thr Thr Thr Thr Thr Thr Thr Thr Thr Thr Thr Thr Thr Thr Thr Thr
        50                  55                  60

Thr Thr Thr Thr Thr Thr Thr Thr Thr Thr Thr Thr Thr Thr Thr Thr
65                  70                  75                  80

Thr Thr Thr Thr Lys Lys Pro Thr Thr Thr Thr Thr Thr Thr Thr Thr
                85                  90                  95

Thr Thr Thr Lys Lys Pro Thr Thr Thr Thr Ala Thr Thr Thr Thr
            100                 105                 110

Thr Thr Ser Glu Thr Glu Ser Val Ile Lys Pro Asp Glu Trp Cys Trp
        115                 120                 125

Leu Glu
    130

(2) INFORMATION FOR SEQ ID NO:14:

(i) SEQUENCE CHARACTERISTICS:
        (A) LENGTH: 130 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:14:

Met Gly Ser Lys Val Tyr Ile Pro Tyr Thr Lys Cys Val Gly Val Lys
1               5                   10                  15

His Thr Thr Thr Thr Thr Thr Thr Thr Thr Thr Thr Thr Thr Thr Thr
                20                  25                  30

Thr Thr Thr Thr Thr Thr Thr Thr Thr Thr Thr Thr Thr Thr Lys Pro
            35                  40                  45

Thr Thr Thr Thr Thr Thr Thr Thr Thr Thr Thr Thr Thr Thr Thr Thr
        50                  55                  60

Thr Thr Thr Thr Thr Thr Thr Thr Thr Thr Thr Thr Thr Thr Thr Thr
65                  70                  75                  80

Thr Thr Thr Thr Lys Lys Pro Thr Thr Thr Thr Thr Thr Thr Thr Thr
                85                  90                  95

Thr Thr Thr Lys Lys Pro Thr Thr Thr Thr Ala Thr Thr Thr Thr
            100                 105                 110

Thr Thr Ser Glu Thr Glu Ser Val Ile Lys Pro Asp Glu Trp Cys Trp
        115                 120                 125

Leu Glu
    130

(2) INFORMATION FOR SEQ ID NO:15:

(i) SEQUENCE CHARACTERISTICS:
        (A) LENGTH: 138 amino acids (B) TYPE: amino acid
            (C) STRANDEDNESS:
            (D) TOPOLOGY: linear (ii) MOLECULE TYPE: protein (xi) SEQUENCE DESCRIPTION: SEQ ID NO:15:

Met Gly Ser Lys Val Tyr Ile Pro Tyr Thr Lys Cys Val Gly Val Lys
1               5                   10                  15

His Thr Thr Thr Thr Thr Thr Thr Thr Thr Thr Thr Thr Thr Thr Thr
                20                  25                  30

Thr Thr Thr Thr Thr Thr Thr Thr Thr Thr Thr Thr Thr Thr Thr Thr
            35                  40                  45

Thr Thr Thr Thr Thr Thr Thr Thr Thr Thr Thr Thr Thr Thr Thr Thr
        50                  55                  60

Thr Thr Thr Thr Thr Thr Thr Thr Thr Thr Thr Thr Thr Thr Thr Thr
65                  70                  75                  80

Thr Thr Thr Thr Thr Thr Thr Thr Thr Thr Thr Lys Lys Pro Thr
                85                  90                  95

Thr Thr Thr Thr Thr Thr Thr Thr Thr Thr Thr Lys Lys Pro Thr Thr
                100                 105                 110

Thr Thr Thr Ala Thr Thr Thr Thr Thr Thr Ser Glu Thr Glu Ser Val
            115                 120                 125

Ile Lys Pro Asp Glu Trp Cys Trp Leu Glu
        130                 135

(2) INFORMATION FOR SEQ ID NO:16:

(i) SEQUENCE CHARACTERISTICS:
        (A) LENGTH: 124 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:16:

Met Gly Ser Lys Val Tyr Ile Pro Tyr Thr Lys Cys Val Gly Val Lys
1               5                   10                  15

His Thr Thr Thr Thr Thr Thr Thr Thr Thr Thr Thr Thr Thr Thr Thr
                20                  25                  30

Thr Thr Thr Thr Thr Thr Thr Thr Thr Thr Thr Thr Thr Thr Thr Thr
            35                  40                  45

Thr Thr Thr Thr Thr Thr Thr Thr Thr Thr Thr Thr Thr Thr Thr Thr
        50                  55                  60

Thr Thr Thr Thr Thr Thr Thr Thr Thr Thr Thr Thr Thr Thr Lys Glu
65                  70                  75                  80

Pro Thr Thr Thr Thr Thr Thr Thr Thr Thr Thr Thr Thr Lys Lys Pro
                85                  90                  95

Thr Thr Thr Thr Thr Ala Thr Thr Thr Thr Thr Thr Ser Glu Thr Glu
                100                 105                 110

Ser Val Ile Lys Pro Asp Glu Trp Cys Trp Leu Glu
            115                 120

(2) INFORMATION FOR SEQ ID NO:17:

(i) SEQUENCE CHARACTERISTICS:
        (A) LENGTH: 175 amino acids
        (B) TYPE: amino acid
        (C) STRANDEDNESS:

(D) TOPOLOGY: linear (ii) MOLECULE TYPE: protein (xi) SEQUENCE DESCRIPTION: SEQ ID NO:17:

```
Met Gly Ser Lys Val Tyr Ile Pro Tyr Thr Lys Cys Val Gly Val Lys
1               5                   10                  15
His Thr Thr Thr Thr Thr Thr Thr Thr Thr Thr Thr Thr Thr Thr Thr
            20                  25                  30
Thr Thr Thr Thr Thr Thr Thr Thr Thr Thr Thr Thr Thr Thr Thr Thr
            35                  40                  45
Thr Thr Thr Thr Thr Thr Thr Thr Thr Thr Thr Thr Thr Thr Thr Thr
        50                  55                  60
Thr Thr Thr Thr Thr Thr Thr Thr Thr Thr Thr Thr Thr Thr Thr Thr
65              70                  75                      80
Thr Thr Thr Thr Lys Lys Pro Thr Thr Thr Thr Thr Thr Thr Thr Thr
                85                  90                  95
Thr Thr Thr Thr Thr Thr Thr Thr Thr Thr Thr Thr Thr Thr Thr Thr
            100                 105                 110
Thr Thr Thr Thr Thr Thr Thr Thr Thr Thr Thr Thr Thr Thr Thr Thr
            115                 120                 125
Thr Lys Lys Pro Thr Thr Thr Thr Thr Thr Thr Thr Thr Thr Thr Thr
    130                 135                 140
Lys Lys Pro Thr Thr Thr Thr Thr Ala Thr Thr Thr Thr Thr Thr Ser
145             150                 155                     160
Glu Thr Glu Ser Val Ile Lys Pro Asp Glu Trp Cys Trp Leu Glu
                165                 170                 175
```

(2) INFORMATION FOR SEQ ID NO:18:

(i) SEQUENCE CHARACTERISTICS:
        (A) LENGTH: 150 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:18:

```
Met Gly Ser Lys Val Tyr Ile Pro Tyr Thr Lys Cys Val Gly Val Lys
1               5                   10                  15
His Thr Thr Thr Thr Thr Thr Thr Thr Thr Thr Thr Thr Thr Thr Thr
            20                  25                  30
Thr Thr Thr Thr Thr Thr Thr Thr Thr Thr Thr Thr Thr Thr Thr Thr
            35                  40                  45
Thr Thr Thr Thr Thr Thr Thr Thr Thr Thr Thr Ala Thr Thr Thr
        50                  55                  60
Thr Thr Thr Thr Thr Thr Thr Thr Thr Thr Thr Thr Thr Thr Thr Thr
65              70                  75                      80
Thr Thr Thr Thr Thr Thr Thr Thr Thr Thr Thr Thr Thr Thr Thr Thr
                85                  90                  95
Thr Thr Thr Thr Thr Thr Thr Lys Lys Pro Thr Thr Thr Thr Thr
            100                 105                 110
Thr Thr Thr Thr Thr Thr Thr Lys Lys Pro Thr Thr Thr Thr Ala
            115                 120                 125
Thr Thr Thr Thr Thr Thr Ser Glu Thr Glu Ser Val Ile Lys Pro Asp
    130                 135                 140
```

-continued

```
Glu Trp Cys Trp Leu Glu
145             150

(2) INFORMATION FOR SEQ ID NO:19:

(i) SEQUENCE CHARACTERISTICS:
        (A) LENGTH: 91 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:19:

Met Gly Ser Lys Val Tyr Ile Pro Tyr Thr Lys Cys Val Gly Val Lys
1               5                   10                  15

His Thr Thr Thr Thr Thr Thr Thr Thr Thr Thr Thr Thr Thr Thr
                20                  25                  30

Thr Thr Thr Thr Thr Thr Thr Thr Thr Thr Thr Thr Thr Thr Thr
            35                  40                  45

Thr Thr Thr Thr Thr Thr Thr Thr Thr Thr Thr Lys Lys Pro Thr
        50                  55                  60

Thr Thr Thr Thr Ala Thr Thr Thr Thr Thr Ser Glu Thr Glu Ser
65                  70                  75                  80

Val Ile Lys Pro Asp Glu Trp Cys Trp Leu Glu
                85                  90

(2) INFORMATION FOR SEQ ID NO:20:

(i) SEQUENCE CHARACTERISTICS:
        (A) LENGTH: 249 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:20:

Met Gly Ser Lys Val Tyr Ile Pro Tyr Thr Lys Cys Val Gly Val Lys
1               5                   10                  15

His Thr Thr Thr Thr Thr Thr Thr Thr Thr Thr Thr Thr Thr Thr
                20                  25                  30

Thr Thr Thr Thr Thr Thr Thr Thr Thr Thr Thr Thr Thr Thr Thr
            35                  40                  45

Thr Thr Thr Thr Thr Thr Thr Thr Thr Thr Thr Thr Thr Thr Thr
        50                  55                  60

Thr Thr Thr Thr Thr Thr Thr Thr Thr Thr Thr Thr Thr Thr Thr
65                  70                  75                  80

Thr Thr Thr Thr Thr Thr Thr Thr Thr Thr Thr Thr Thr Thr Thr
                85                  90                  95

Thr Thr Thr Thr Thr Thr Thr Thr Thr Thr Thr Thr Thr Thr Thr
                100                 105                 110

Thr Thr Thr Thr Thr Thr Thr Thr Thr Thr Thr Thr Thr Thr Thr
            115                 120                 125

Thr Thr Thr Thr Thr Thr Thr Thr Thr Thr Thr Thr Thr Thr Thr
        130                 135                 140

Thr Thr Thr Thr Thr Thr Thr Thr Thr Thr Thr Thr Thr Thr Thr
145                 150                 155                 160

Thr Thr Lys Lys Pro Thr Thr Thr Thr Thr Thr Thr Thr Thr Thr
                165                 170                 175
```

```
Thr Thr Thr Thr Thr Thr Thr Thr Thr Thr Thr Thr Thr Thr Thr
            180                 185                 190

Thr Thr Thr Thr Thr Thr Thr Thr Thr Thr Thr Lys Pro Thr Thr
            195                 200                 205

Thr Thr Thr Thr Thr Thr Thr Thr Thr Lys Lys Pro Thr Thr Thr
            210                 215                 220

Thr Thr Ala Thr Thr Thr Thr Thr Thr Ser Glu Thr Glu Ser Val Ile
225             230                 235                 240

Lys Pro Asp Glu Trp Cys Trp Leu Glu
            245
```

(2) INFORMATION FOR SEQ ID NO:21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

CAGGTACCCA TGAATTGGCC GGTAAGTATC                                      30

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

CAGGTACCCT CTGAAACTGA GAGTGTAATT                                      30

(2) INFORMATION FOR SEQ ID NO:23:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

CCTCAGATTA GTGTTTCACT CCAACACA                                        28

(2) INFORMATION FOR SEQ ID NO:24:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

CCTCTAGATT ATACGAAATC AGCTGAAGT                                       29

(2) INFORMATION FOR SEQ ID NO:25:

```
        (i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:25:

Thr Thr Thr Thr Thr Thr Thr Lys Lys Pro Thr Thr Thr Thr Thr
1               5                   10                  15

(2) INFORMATION FOR SEQ ID NO:26:

(i) SEQUENCE CHARACTERISTICS:
            (A) LENGTH: 191 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:26:

Ile Leu Glu Gly Ser Ile Ala Gly Ile Arg Ser Glu Ser Cys Ile Val
1               5                   10                  15

Ser Glu Leu Asn Phe Thr Ser Thr Thr Gly Phe Thr Thr Asp Thr Ser
                20                  25                  30

Met Asn Trp Pro Val Ser Ile Thr Ser Gly Glu Leu Lys Asp Pro Asn
                35                  40                  45

Lys Gln Ala Thr Ile Ser Gly Ser Arg Ser Cys Gly Trp Lys Gln Gly
            50                  55                  60

Tyr Ser Ile Asp Ser Ser Thr Gly Phe Arg Val Asp Ser Ile Thr Gly
65                  70                  75                  80

Leu Pro Thr Asp Pro Tyr Ser Asn Cys Pro Phe Asn Pro Val Thr Gly
                    85                  90                  95

Asn Leu Val Ser Arg Ser Thr Gly Lys Thr Ile Pro Asn Thr Tyr Ala
                100                 105                 110

Gly Val Tyr Arg Ser Asn Glu Thr Lys Thr Thr Glu Pro Ser Ala Asn
                115                 120                 125

Thr Tyr Ala Gly Val Tyr Arg Ser Asn Glu Thr Lys Thr Thr Glu Pro
            130                 135                 140

Ser Ala Asn Thr Asn Phe Leu Leu Val Asp Pro Lys Ile Asn Ala Pro
145                 150                 155                 160

Cys Asn Ser Glu Asn Ser Phe Glu Gln Gly Gln Ile Phe Asp Met Gly
                    165                 170                 175

Ser Lys Val Tyr Ile Pro Tyr Thr Lys Cys Val Gly Val Lys His
                180                 185                 190

(2) INFORMATION FOR SEQ ID NO:27:

(i) SEQUENCE CHARACTERISTICS:
            (A) LENGTH: 216 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:27:

Thr Thr Thr Thr Thr Thr Thr Thr Thr Thr Thr Thr Thr Thr Thr Thr
1               5                   10                  15

Thr Thr Thr Thr Thr Thr Thr Thr Thr Thr Thr Thr Thr Thr Thr Thr
```

-continued

```
            20                  25                  30
Thr Thr Thr Thr Thr Thr Thr Thr Thr Thr Thr Thr Thr Thr Thr
        35                  40                  45
Thr Thr Thr Thr Thr Thr Thr Thr Thr Thr Thr Thr Thr Thr Thr
 50                  55                  60
Thr Thr Thr Thr Thr Thr Thr Thr Thr Thr Thr Thr Thr Thr Thr
65                  70                  75                  80
Thr Thr Thr Thr Thr Thr Thr Thr Thr Thr Thr Thr Thr Thr Thr
            85                  90                  95
Thr Thr Thr Thr Thr Thr Thr Thr Thr Thr Thr Thr Thr Thr Thr
           100                 105                 110
Thr Lys Lys Pro Thr Thr Thr Thr Thr Thr Thr Thr Thr Thr Thr
           115                 120                 125
Thr Thr Thr Thr Thr Thr Thr Thr Thr Thr Thr Thr Thr Thr Thr
       130                 135                 140
Thr Lys Lys Pro Thr Thr Thr Thr Thr Thr Thr Thr Thr Thr Thr
145                 150                 155                 160
Thr Thr Thr Thr Thr Thr Thr Thr Thr Thr Thr Thr Thr Thr Thr
            165                 170                 175
Thr Thr Thr Thr Thr Thr Thr Thr Thr Thr Thr Lys Pro Thr Thr Thr
        180                 185                 190
Thr Thr Thr Thr Thr Thr Thr Thr Lys Lys Pro Thr Thr Thr Thr
        195                 200                 205
Thr Ala Thr Thr Thr Thr Thr Thr
       210                 215
```

(2) INFORMATION FOR SEQ ID NO:28:

(i) SEQUENCE CHARACTERISTICS:
        (A) LENGTH: 159 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:28:

```
Ser Glu Thr Glu Ser Val Ile Lys Pro Asp Glu Trp Cys Trp Leu Glu
 1               5                  10                  15
Lys Asn Gly Glu Cys Glu Ala Lys Gly Ala Thr Tyr Val Gly Val Ile
                20                  25                  30
Gly Lys Asp Gly Arg Ile Glu Asn Gly Met Ala Phe Thr Met Ile Pro
            35                  40                  45
Asn Asp Asp Thr His Val Arg Phe Arg Phe Lys Val Lys Asp Val Gly
        50                  55                  60
Asn Thr Ile Ser Val Arg Cys Arg Lys Gly Ala Gly Lys Leu Glu Phe
65                  70                  75                  80
Pro Asp Arg Ser Leu Asp Phe Thr Ile Pro Pro Val Ala Gly His Asn
                85                  90                  95
Ser Cys Ser Ile Ile Val Gly Val Ser Gly Asp Gly Lys Ile His Val
               100                 105                 110
Ser Pro Tyr Gly Ser Lys Asp Val Ser Leu Ile Ser Ala Pro Ile Gln
           115                 120                 125
Pro Ser Glu Leu Phe Asn Glu Val Tyr Cys Asp Thr Cys Thr Ala Lys
       130                 135                 140
Tyr Gly Ala Ile His Ser Gly Tyr Gln Thr Ser Ala Asp Phe Val
```

(2) INFORMATION FOR SEQ ID NO:29:

(i) SEQUENCE CHARACTERISTICS:
        (A) LENGTH: 112 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:29:

```
Thr Thr Thr Thr Ala Lys Pro Thr Thr Thr Thr Gly Ala Pro Gly
  1               5                  10                  15

Gln Pro Thr Thr Thr Thr Thr Gly Ser Pro Ser Lys Pro Thr Thr Thr
             20                  25                  30

Thr Thr Thr Lys Ala Thr Thr Thr Thr Thr Leu Asn Pro Ile Ile
             35                  40                  45

Thr Thr Thr Thr Gln Lys Pro Thr Thr Thr Thr Thr Lys Val Pro
 50                  55                  60

Gly Lys Pro Pro Ile Ala Thr Thr Thr Thr Leu Lys Pro Ile Val
 65                  70                  75                  80

Thr Thr Thr Thr Thr Lys Ala Thr Thr Thr Thr Thr Thr Val Pro
             85                  90                  95

Thr Thr Thr Thr Thr Thr Lys Arg Asp Glu Met Thr Thr Thr Thr
            100                 105                 110
```

(2) INFORMATION FOR SEQ ID NO:30:

(i) SEQUENCE CHARACTERISTICS:
        (A) LENGTH: 1043 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:30:

```
Pro Leu Pro Asp Ile Gly Asp Ile Glu Ile Thr Pro Ile Pro Ile Glu
  1               5                  10                  15

Lys Met Leu Asp Lys Tyr Thr Arg Met Ile Tyr Asp Tyr Asn Ser Gly
             20                  25                  30

Leu Leu Leu Asp Ser Asn Asp Glu Pro Ile Pro Gly Ser Gln Ala Gly
             35                  40                  45

Gln Ile Ala Asp Thr Ser Asn Leu Phe Pro Val Gln Thr His Lys Ser
 50                  55                  60

Thr Gly Leu Pro Ile Asp Pro Met Val Gly Leu Pro Phe Asp Pro Lys
 65                  70                  75                  80

Ser Gly Asn Leu Val His Pro Tyr Thr Asn Gln Thr Met Ser Gly Leu
             85                  90                  95

Ser Val Ser Tyr Leu Ala Ala Lys Asn Leu Thr Val Asp Thr Asp Glu
            100                 105                 110

Thr Tyr Gly Leu Pro Ile Asp Thr Leu Thr Gly Tyr Pro Leu Asp Pro
            115                 120                 125

Val Ser Leu Ile Pro Phe Asn Pro Glu Thr Gly Glu Leu Phe Asp Pro
            130                 135                 140

Ile Ser Asp Glu Ile Met Asn Gly Thr Ile Ala Gly Ile Val Ser Gly
145                 150                 155                 160
```

```
Ile Ser Ala Ser Glu Ser Leu Leu Ser Gln Lys Ser Ala Leu Ile Asp
                165                 170                 175

Pro Ala Thr Asn Met Val Val Gly Glu Phe Gly Gly Leu Leu Asn Pro
            180                 185                 190

Ala Thr Gly Val Met Ile Pro Gly Phe Leu Gly Pro Ser Glu Gln Thr
        195                 200                 205

Gln Phe Ser Pro Glu Ile Glu Asp Gly Gly Ile Ile Pro Pro Glu Val
    210                 215                 220

Ala Ala Ala Asn Ala Asp Lys Phe Lys Leu Ser Ile Pro Pro Ser Val
225                 230                 235                 240

Pro Glu Ser Ile Pro Glu Lys Asp Gln Lys Ile Asp Ser Ile Ser Glu
                245                 250                 255

Leu Met Tyr Asp Ile Glu Ser Gly Arg Leu Ile Gly Gln Val Ser Lys
            260                 265                 270

Arg Pro Ile Pro Gly Ser Ile Ala Gly Asp Leu Asn Pro Ile Met Lys
        275                 280                 285

Thr Pro Thr Gln Thr Asp Ser Val Thr Gly Lys Pro Ile Asp Pro Thr
    290                 295                 300

Thr Gly Leu Pro Phe Asn Pro Pro Thr Gly His Leu Ile Asn Pro Thr
305                 310                 315                 320

Asn Asn Asn Thr Met Asp Ser Ser Phe Ala Gly Ala Tyr Lys Tyr Ala
                325                 330                 335

Val Ser Asn Gly Ile Lys Thr Asp Asn Val Tyr Gly Leu Pro Val Gly
            340                 345                 350

Glu Ile Thr Gly Leu Pro Lys Asp Pro Gly Ser Asp Ile Pro Phe Asn
        355                 360                 365

Ser Thr Thr Gly Glu Leu Val Asp Pro Ser Thr Gly Lys Pro Ile Asn
    370                 375                 380

Asn Ser Thr Ala Gly Ile Val Ser Gly Lys Pro Gly Leu Pro Pro Ile
385                 390                 395                 400

Glu Asp Glu Asn Gly Asn Leu Phe Asp Pro Ser Thr Asn Leu Pro Ile
                405                 410                 415

Asp Gly Asn Asn Gln Leu Val Asn Pro Glu Thr Asn Ser Thr Val Ser
            420                 425                 430

Gly Ser Thr Ser Gly Thr Thr Lys Pro Lys Pro Gly Ile Pro Val Asn
        435                 440                 445

Gly Gly Gly Val Val Pro Asp Glu Glu Ala Lys Asp Gln Ala Asp Lys
    450                 455                 460

Gly Lys Asp Gly Leu Ile Val Pro Pro Thr Asn Ser Ile Asn Lys Asp
465                 470                 475                 480

Pro Val Thr Asn Thr Gln Tyr Ser Asn Thr Thr Gly Asn Ile Ile Asn
                485                 490                 495

Pro Glu Thr Gly Lys Val Ile Pro Gly Ser Leu Pro Gly Ser Leu Asn
            500                 505                 510

Tyr Pro Ser Phe Asn Thr Pro Gln Gln Thr Asp Glu Ile Thr Gly Lys
        515                 520                 525

Pro Val Asp Thr Val Thr Gly Leu Pro Tyr Asp Pro Ser Thr Gly Glu
    530                 535                 540

Ile Ile Asp Pro Ala Thr Lys Leu Pro Ile Pro Gly Ser Val Ala Gly
545                 550                 555                 560

Asp Glu Ile Leu Thr Glu Val Leu Asn Ile Thr Thr Asp Glu Val Thr
                565                 570                 575

Gly Leu Pro Ile Asp Leu Glu Thr Gly Leu Pro Arg Asp Pro Val Ser
```

```
                      580                 585                 590
Gly Leu Pro Gln Leu Pro Asn Gly Thr Leu Val Asp Pro Ser Asn Lys
            595                 600                 605
Lys Pro Ile Pro Gly Ser His Ser Gly Phe Ile Asn Gly Thr Ser Gly
            610                 615                 620
Glu Gln Ser His Glu Lys Asp Pro Ser Thr Gly Lys Pro Leu Asp Pro
625                 630                 635                 640
Asn Thr Gly Leu His Pro Phe Asp Glu Asp Ser Gly Ser Leu Ile Asn
            645                 650                 655
Pro Glu Thr Gly Asp Lys Leu Gln Gly Ser His Ser Gly Thr Phe Met
            660                 665                 670
Pro Val Pro Gly Lys Pro Gln Gly Glu Asn Gly Gly Ile Met Thr Pro
            675                 680                 685
Glu Gln Ile Leu Glu Ala Leu Asn Lys Leu Pro Thr Ser Asn Glu Val
            690                 695                 700
Asn Ile Ser Pro Arg Pro Ser Ser Asp Ala Val Pro Asp Arg Pro Thr
705                 710                 715                 720
Asn Thr Trp Trp Asn Lys Ile Ser Gly Gln Thr Tyr Gln Val Asp Gly
            725                 730                 735
Lys Lys Thr Ile Pro Gly Ser Ala Ala Ser Val Ile His Thr Ala Leu
            740                 745                 750
Gly Thr Pro Thr Gln Thr Asp Pro Thr Thr Gly Leu Pro Ser Asp Pro
            755                 760                 765
Ser Thr Gly Leu Pro Phe Ile Pro Gly Phe Asn Val Leu Val Asp Pro
            770                 775                 780
Gln Thr Gly Glu Gln Ile Lys Gly Ser Val Pro Tyr Val Ser Leu Tyr
785                 790                 795                 800
Val Lys Glu Lys Asn Ile Val Thr Glu Ala Ala Tyr Gly Leu Pro Val
            805                 810                 815
Asp Pro Lys Thr Gly Phe Pro Ile Asp Pro Ile Ser Tyr Leu Pro Phe
            820                 825                 830
Ala Lys Asn Gly Glu Leu Ile Asp Pro Ile Ser Gly Lys Tyr Phe Ser
            835                 840                 845
Gly Ser Ile Ala Gly Phe Ile Ser Gly Lys Ala Gly Ser Gln Ser Lys
            850                 855                 860
Ser Ser Asp Glu Ser Gly Asn Pro Ile Asp Pro Ser Thr Asn Met Pro
865                 870                 875                 880
Tyr Asp Pro Lys Gly Gly Lys Leu Ile Asp Pro Glu Ser Gly Ile Ala
                        885                 890                 895
Ile Asp Asn Ser Val Ser Gly Val Phe Ala Thr Val Pro Gly Thr Ala
            900                 905                 910
Ala Pro Lys Lys Gly Gly Val Ile Pro Glu Ser Val Ala Ala Glu Ala
            915                 920                 925
Ala Lys Lys Tyr Phe Ala Ala Asn Val Glu Gly Glu Gly Glu Gly Glu
            930                 935                 940
Glu Val Pro Pro Pro Glu Ser Ser Asn Ile Ala Ile Gln Ala
945                 950                 955                 960
Ala Gly Gly Ala Ser Ala Ala Val Gly Leu Val Ala Ala Val Gly Ala
                        965                 970                 975
Trp Tyr Ala Ser Arg Asn Arg Gln Glu Gly Glu Asp Asp Asp Tyr
            980                 985                 990
Gln Met Asp Leu Lys Gln Asn Met Lys Lys Arg Lys Lys Arg Val
            995                 1000                1005
```

```
Met Lys Gln Gln Met Lys Leu Leu Leu Gln Leu Ser Val Ile His His
    1010            1015            1020

Ser Gly Thr Asn Leu Lys Arg Arg Lys Asp Phe Ser Asn Ser Lys Lys
1025            1030            1035            1040

Phe Arg Ile
```